US012678461B2

(12) United States Patent
Long et al.

(10) Patent No.: US 12,678,461 B2
(45) Date of Patent: Jul. 14, 2026

(54) CD28H DOMAIN-CONTAINING CHIMERIC ANTIGEN RECEPTORS AND METHODS OF USE

(71) Applicant: The United States of America, as represented by the Secretary, Dept. of Health and Human Services, Bethesda, MD (US)

(72) Inventors: Eric O. Long, Rockville, MD (US); Xiaoxuan Zhuang, Rockville, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 847 days.

(21) Appl. No.: 17/914,027

(22) PCT Filed: Mar. 26, 2020

(86) PCT No.: PCT/US2020/024985
§ 371 (c)(1),
(2) Date: Sep. 23, 2022

(87) PCT Pub. No.: WO2021/194495
PCT Pub. Date: Sep. 30, 2021

(65) Prior Publication Data
US 2023/0190800 A1 Jun. 22, 2023

(51) Int. Cl.
| | |
|---|---|
| *A61K 35/17* | (2025.01) |
| *A61K 38/00* | (2006.01) |
| *A61K 40/31* | (2025.01) |
| *A61P 35/00* | (2006.01) |
| *C07K 14/705* | (2006.01) |

(52) U.S. Cl.
CPC .............. *A61K 35/17* (2013.01); *A61P 35/00* (2018.01); *C07K 14/70521* (2013.01); *A61K 38/00* (2013.01)

(58) Field of Classification Search
CPC .................................................... A61K 40/31
See application file for complete search history.

(56) References Cited

U.S. PATENT DOCUMENTS

2022/0054545 A1* 2/2022 McGinness ............ A61K 40/31

OTHER PUBLICATIONS

Zhuang et al., Cancer Immunology Research, vol. 7, No. 6, pp. 939-951, Apr. 24, 2019.*
Bridgeman et al. (J. Immunol. Jun. 15, 2010; 184 (12): 6938-49).*
Altvater et al., "2B4 (CD244) Signaling by Recombinant Antigen-specific Chimeric Receptors Costimulates Natural Killer Cell Activation to Leukemia and Neuroblastoma Cells," *Clinical Cancer Research,* vol. 15, No. 15, pp. 4857-4866, 2009.
Li et al., "Human iPSC-Derived Natural Killer Cells Engineered with Chimeric Antigen Receptors Enhance Antitumor Activity," *Cell Stem Cell,* vol. 23, pp. 181-192, 2018.
Pfefferle et al., "You Have Got a Fast CAR: Chimeric Antigen Receptor NK Cells in Cancer Therapy," *Cancers,* 12:706, 2020 (23 pages).
Zhuang et al., "CD28 Homolog Is a Strong Activator of Natural Killer Cells for Lysis of B7H7+ Tumor Cells," *Cancer Immunology Research,* vol. 7, No. 6, pp. 939-951, Apr. 24, 2019.
Zhuang et al., "CD28 homolog is a strong activator of natural killer cells for lysis of B7H7-positive tumor cells," *J. Immunol.* vol. 202 (1 Supplement) 134.5, May 1, 2019.
Zhuang et al., "Inhibition-Resistant CARs for NK Cell Cancer Immunotherapy," *Trends in Immunology,* vol. 40, No. 12, pp. 1078-1081, Nov. 12, 2019.

* cited by examiner

*Primary Examiner* — Gary B Nickol
(74) *Attorney, Agent, or Firm* — Klarquist Sparkman, LLP

(57) ABSTRACT

Chimeric antigen receptors including (a) an antigen binding domain; (b) a transmembrane domain; and (c) an intracellular domain comprising a first intracellular signaling domain from CD28 homolog (CD28H) and a second intracellular signaling domain are provided. In some examples, the second intracellular domain is from 2B4, TCRζ, FcεR1γ, or DAP12. Chimeric antigen receptors including (a) an antigen binding domain; (b) a transmembrane domain; and (c) an intracellular domain comprising a first intracellular signaling domain from CD28H, a second intracellular signaling domain from 2B4, and a third intracellular signaling domain are also provided. In some examples, the third intracellular domain is from TCRζ, FcεR1γ, or DAP12. Nucleic acid molecules encoding the CARs and expression vectors including the nucleic acids are also provided. Isolated cells (such as T cells or natural killer cells) expressing the CARs and methods of treating a subject with cancer with the isolated cells are provided.

14 Claims, 40 Drawing Sheets
Specification includes a Sequence Listing.

FIG. 1D
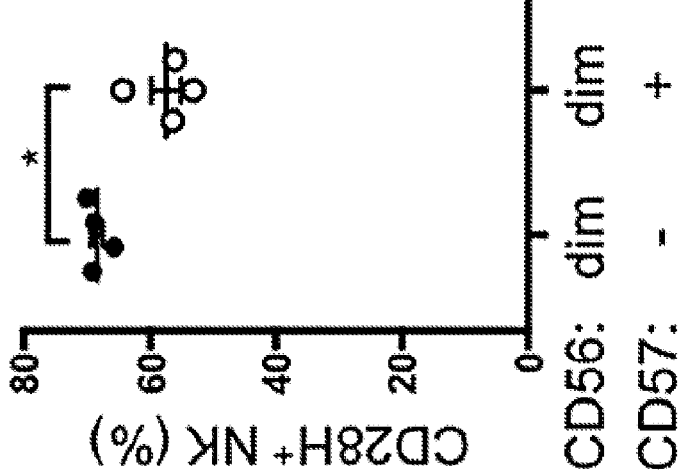
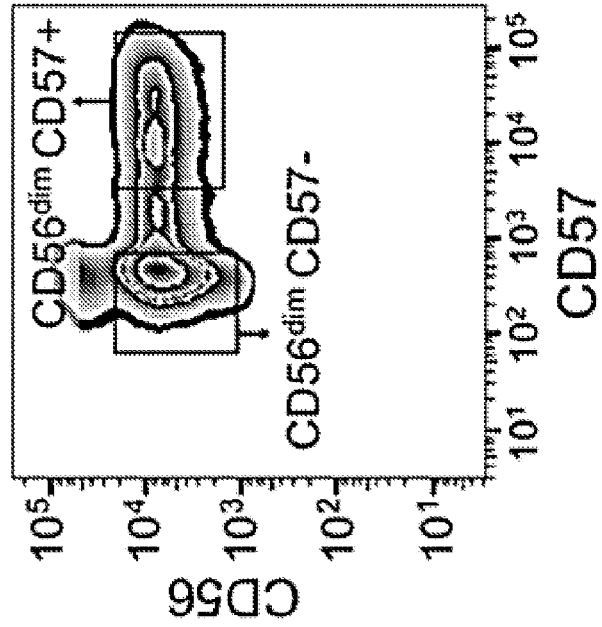

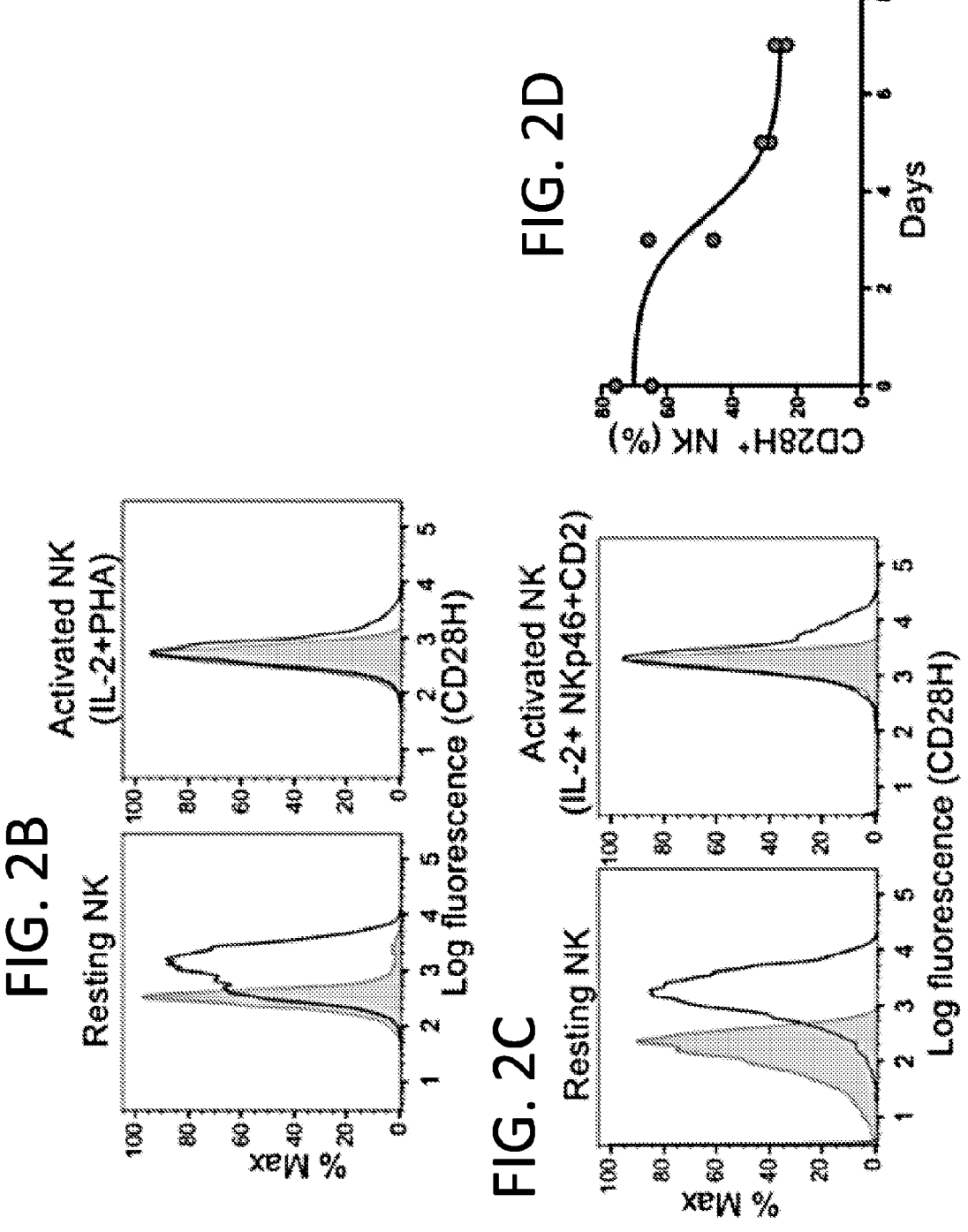

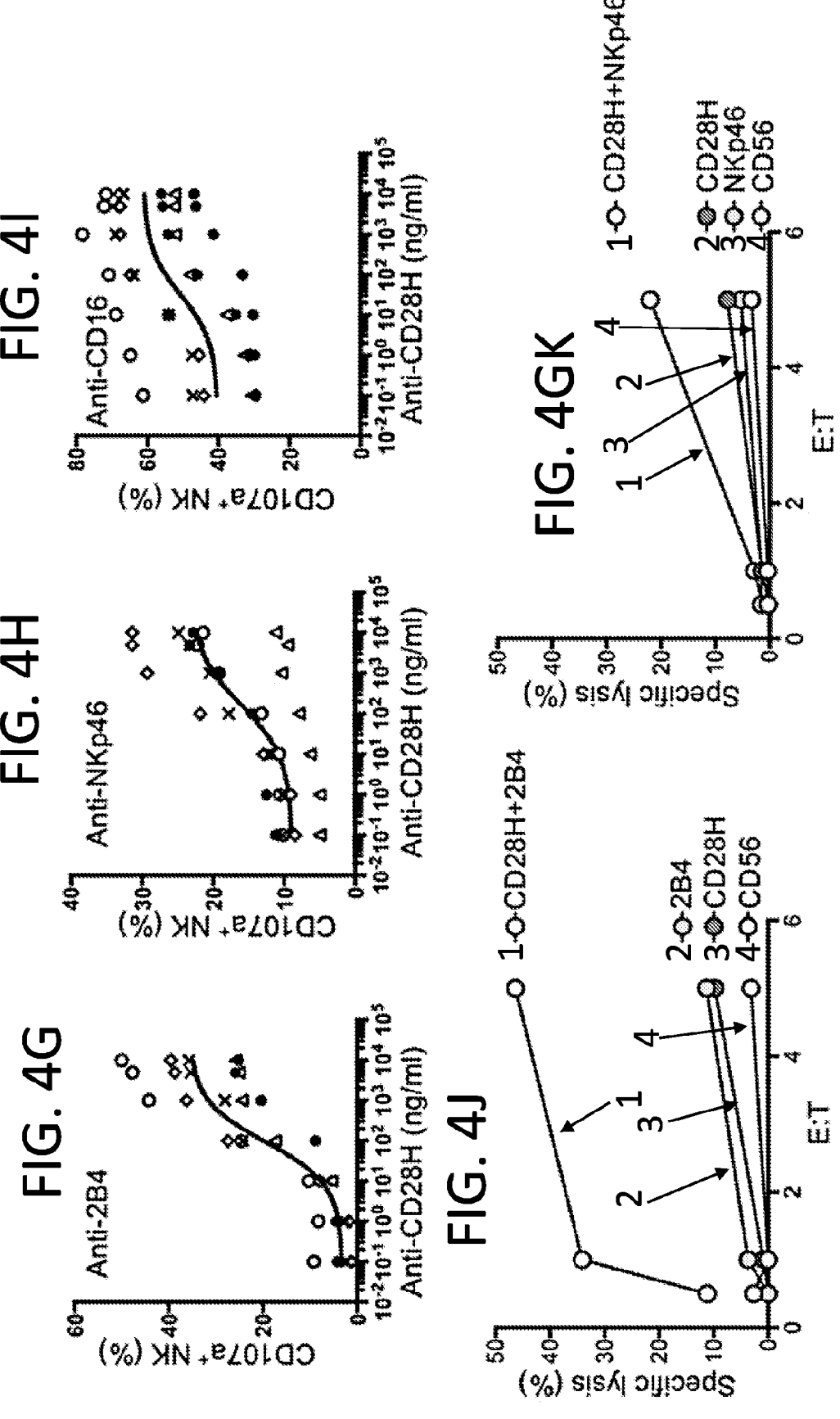

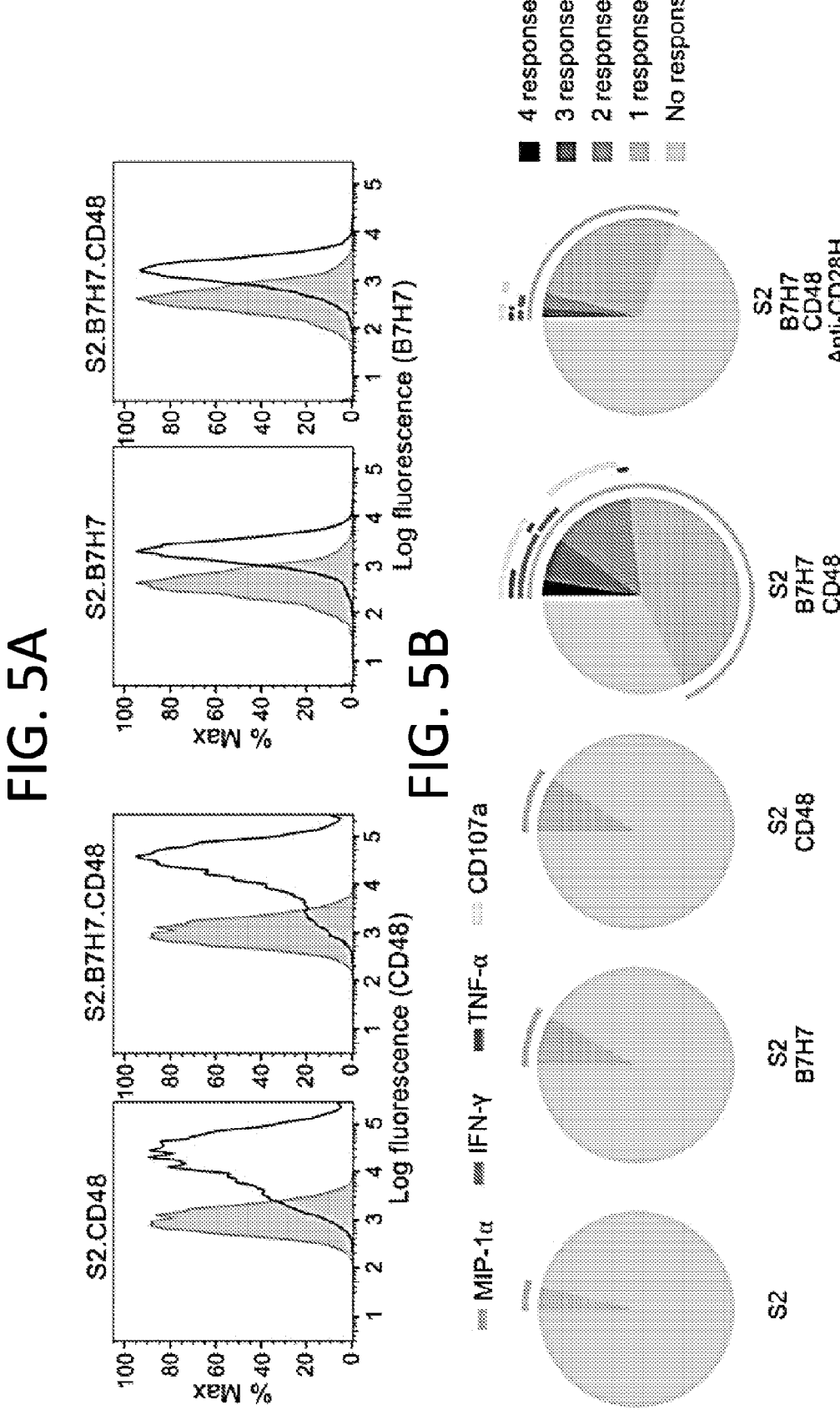

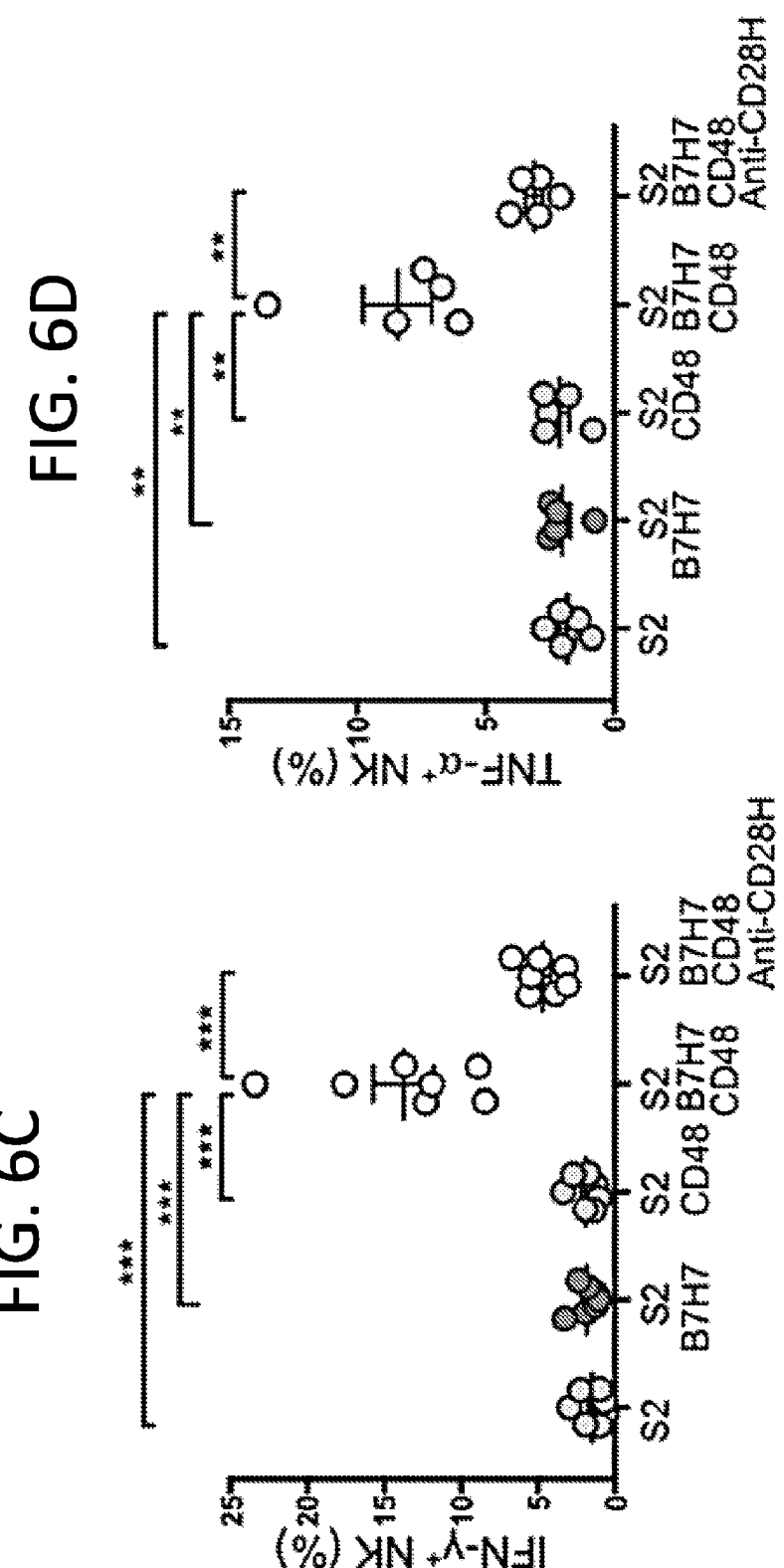

1 -o- Y197F
2 -o- Y197F-Y222F
3 -o- Y222F
4 -●- WT

5 -o- Y192F-Y197F
6 -●- Y192F-Y197F-Y222F
7 -●- Y192F-Y222F
8 -o- Y192F
9 -o- Ctrl (221)

1 -o- Y197F
2 -o- Y197F-Y222F
3 -●- WT
4 -●- Y222F

5 -o- Ctrl (221)
6 -●- Y192F-Y222F
7 -●- Y192F-Y197F-Y222F
8 -o- Y192F-Y197F
9 -●- Y192F

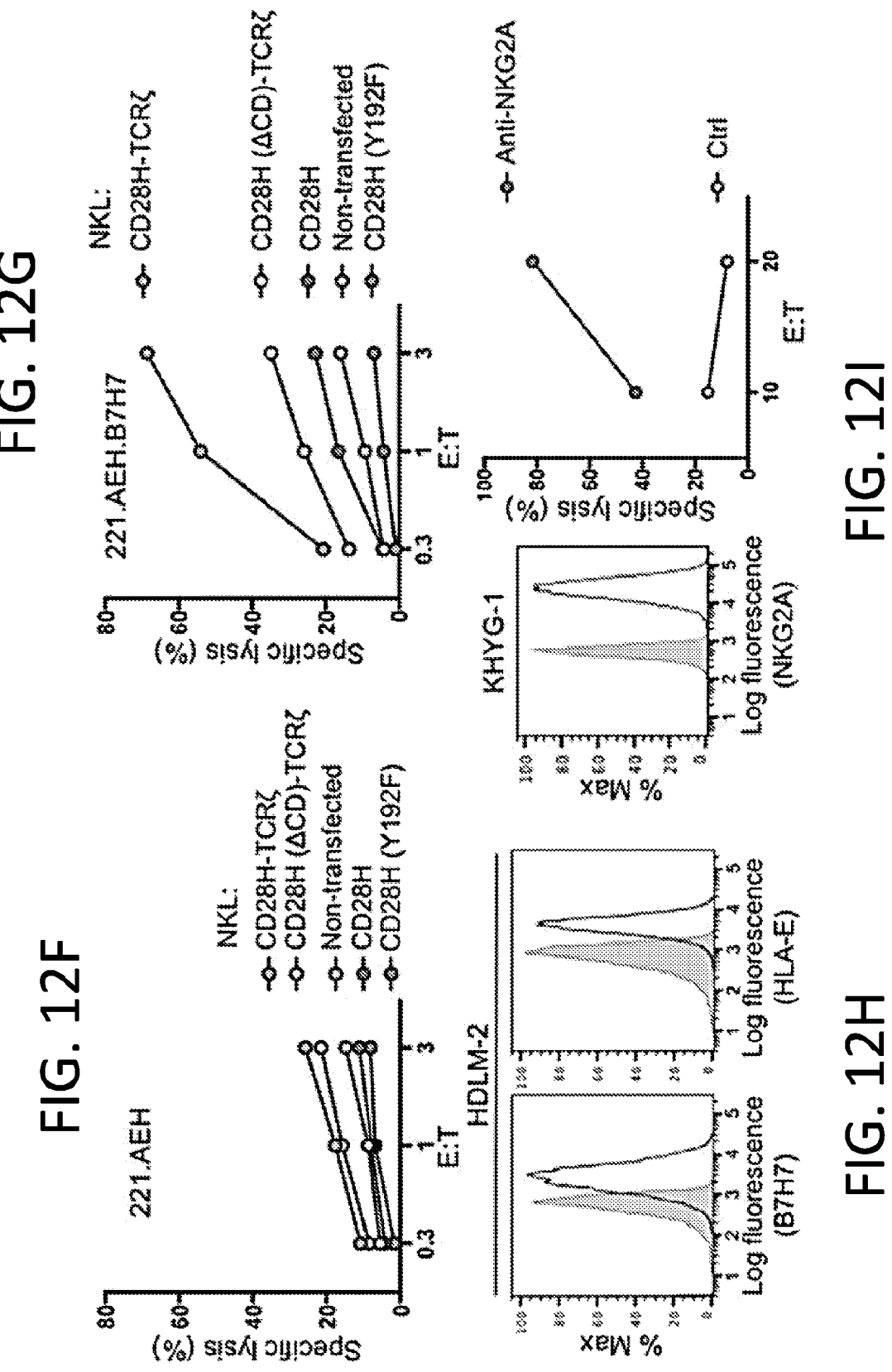

FIG. 13C

CD28H DOMAIN-CONTAINING CHIMERIC ANTIGEN RECEPTORS AND METHODS OF USE

CROSS REFERENCE TO RELATED APPLICATION

This is the U.S. National Stage of International Application No. PCT/US2020/024985, filed Mar. 26, 2020, which was published in English under PCT Article 21(2), which is incorporated herein in its entirety.

FIELD

This disclosure relates to chimeric antigen receptors containing a CD28H signaling domain and methods of their use, particularly for treating cancer.

BACKGROUND

Immunotherapy with CAR-T cells has been successful in clinical treatment of hematologic cancers, and substantial progress has been made in targeting solid tumors. However, unique adverse side-effects associated with infusion of CAR-T cells, such as severe cytokine-release-syndrome (CRS) and neurotoxicity, could be life-threatening and need to be carefully managed. Natural killer cells have great potential as effector cells in adoptive cell therapy due to their safer cytokine profile and low graft-versus-host-disease (GVHD) activity, as observed in hematopoietic stem cell transplantation. To reduce the cost of CAR-T cell therapy and simplify the process of CAR-T cell production, "off-the-shelf" CAR-T cell strategies have been proposed. T cell receptors (TCRs) on allogeneic CAR-T cells derived from healthy donors have to be silenced in order to minimize GVHD and produce universal cryopreserved CAR-T cell products that are ready for use when needed. Notably, unlike T cells, "off-the-shelf" CAR-NK strategies can be developed without the need for genetically silencing TCR. Safety and persistence of donor-derived NK cells have been demonstrated by the decades-long clinical practice of hematopoietic stem cell transplantation. Moreover, additional beneficial effects can be provided by germline encoded NK-cell activation receptors for ligands on tumor cells.

Activation of NK cells requires a synergistic combination of signals from activation receptors, the ligands of which are usually upregulated on transformed or infected cells. However, activation signals are counteracted by inhibitory receptors for MHC-I, including receptor CD94-NKG2A for the non-classical MHC-I HLA-E and inhibitory killer-cell Ig-like receptors (KIRs) for classical MHC-I molecules. Specifically, KIR2DL1 is a receptor for HLA-C group 1 (C1), KIR2DL2/3 for HLA-C group 2 (C2), and KIR3DL1 for certain alleles of HLA-B. Signaling by these inhibitory receptors is typically dominant over signaling by co-activation receptors. Inhibitory receptors have also the important function of maintaining NK cells in a state of high-responsiveness, a property which has been called licensing or education.

SUMMARY

In order for adoptive cell therapy with NK cells to succeed in elimination of tumor cells, signaling by inhibitory receptors needs to be reduced or overridden. Disclosed herein are CARs that include a CD28 homolog (CD28H) activation domain (also referred to as a CD28H intracellular signaling domain), which endows CARs with the ability to overcome inhibition, for example, by CD94-NKG2A and by KIR2DL1.

Disclosed are chimeric antigen receptors (CARs) including (a) an antigen binding domain; (b) a transmembrane domain; and (c) an intracellular domain, comprising a first intracellular signaling domain from CD28H and a second intracellular signaling domain. Domains (a)-(c) are in N-terminal to C-terminal order; however, the first and second intracellular signaling domains of the intracellular domain can be either order. In some examples, the second intracellular signaling domain is from 2B4, TCRζ, FcεR1γ, or DAP12. In one particular example, the second intracellular signaling domain is from TCRζ. In another particular example, the second intracellular signaling domain is from 2B4. In some embodiments, the CAR further includes a hinge domain (such as a CD8 hinge domain) that is C-terminal to the antigen binding domain and N-terminal to the transmembrane domain.

Also provided are chimeric antigen receptors (CARs) including (a) an antigen binding domain; (b) a transmembrane domain; and (c) an intracellular domain, comprising a first intracellular signaling domain from CD28H, a second intracellular signaling domain from 2B4, and a third intracellular signaling domain. In some examples, the third intracellular signaling domain is from TCRζ, FcεR1γ, or DAP12. Domains (a)-(c) are in N-terminal to C-terminal order; however, the first, second, and third intracellular signaling domains can be any order. In some embodiments, the CAR further includes a hinge domain (such as a CD8 hinge domain) that is C-terminal to the antigen binding domain and N-terminal to the transmembrane domain.

In some embodiments, the CARs disclosed herein include an amino acid sequence with at least 90% sequence identity to the amino acid sequence of any one of SEQ ID NOs: 2, 6, 12, 16, and 20. In particular examples, CARs include or consist of the amino acid sequence of any one of SEQ ID NOs: 2, 6, 12, 16, and 20.

Also disclosed are nucleic acid molecules encoding the CARs provided herein. In some embodiments, the nucleic acid molecule is included in an expression vector (such as a lentiviral or retroviral vector). In embodiments, the CARs include a nucleic acid sequence with at least 90% sequence identity to the nucleic acid sequence of any one of SEQ ID NOs: 1, 5, 11, 15, and 19 or include or consist of the nucleic acid sequence of any one of SEQ ID NOs: 1, 5, 11, 15, and 19. Isolated cells (such as T cells or natural killer cells) expressing the CARs are provided, as are compositions including the cells and a pharmaceutically acceptable carrier.

Further provided are methods of treating a subject with cancer (such as a hematological malignancy or solid tumor). Such methods include administering to the subject an isolated cell or composition disclosed herein. In some examples, the cells are NK cells expressing a CAR, such as autologous NK cells.

The foregoing and other features of the disclosure will become more apparent from the following detailed description, which proceeds with reference to the accompanying figures.

BRIEF DESCRIPTION OF THE DRAWINGS

FIGS. 1A-1D show CD28H expression on human NK cells. FIG. 1A: Freshly isolated NK cells were stained for CD56 and CD28H with fluorophore-conjugated mAbs. An isotype control (IgG) for CD28H is shown in the left panel.

FIG. 1B: Expression of CD28H was compared between CD56$^{bright}$ and CD56$^{dim}$ NK cells. Each symbol represents an independent donor (n=4). FIG. 1C: Expression of CD28H in different CD56$^{dim}$ subsets defined by KIR and NKG2A expression. Receptors of the KIR family were stained using a cocktail of PE-conjugated antibodies (EB6, GL183 and DX9). Each symbol represents an independent donor (n=4) FIG. 1D: CD28H expression on CD56$^{dim}$CD57$^-$ and CD56$^{dim}$CD57$^+$ NK cells. Each symbol represents an independent donor (n=4). All data are presented as the mean±SEM. *P<0.05, n.s., not-significant (Mann-Whitney test, two-tailed). All experiments were repeated at least twice.

FIGS. 2A-2F. FIG. 2A: Gating strategy of different CD56$^{dim}$ NK cell populations based on NKG2A and KIR expression. KIR expression was determined by a cocktail of PE-conjugated antibodies (EB6, GL183 and DX9). FIG. 2B: Representative histogram of immunostaining for CD28H in resting NK cells and NK cells expanded in IL-2 and PHA for 14 days. Freshly isolated or IL-2 cultured NK cells were stained with isotype control (shaded) or CD28H mAb (solid line), followed by incubation with PE-conjugated goat anti-mouse secondary antibody. FIG. 2C: Representative histogram of immunostaining for CD28H in resting NK cells (left) or NK cells activated by IL-2 and crosslinking of CD2 and NKp46 (right). NK cells were activated by plate-bound mAbs to CD2 and NKp46 plus 100 U/ml IL-2 for 7 days. FIG. 2D: Expression of CD28H at different time points after activation of NK cells from 2 donors as in FIG. 2C. The percentage of NK cells that were CD28H$^+$ was determined by staining for CD56 and CD28H. FIG. 2E: CD25 expression on NK cells at different time points after IL-2 stimulation. FIG. 2F: Resting NK cells were activated in IL-2 for 24 hours, followed by staining for CD56, CD25 and CD28H. Expression of CD28H in CD25$^-$ and CD25$^+$ NK cells shown in histogram (right) and presented as data from 3 independent donors (left). Mean±SEM. n.s., not-significant (Mann-Whitney test, two-tailed).

FIG. 3A: Schematics of redirected cytotoxicity assay. In the assay, the F(ab') 2 portions of the mAbs specifically recognize NK cell receptors, while the Fc fragments bind to Fc receptor on mouse P815 cells. NK cells are synergistically activated by the crosslinked NK cell activation receptors. FIG. 3B: Surface expression of 2B4, NKp46, and CD28H in the NKL, YTS, KHYG-1, and NK-92 cell lines determined by immunostaining with fluorophore-conjugated mAbs. Shaded histograms represent staining with isotype controls. FIG. 3C: Lysis of P815 cells by KHYG-1 cells in redirected cytotoxicity assays. KHYG-1 cells were rested without IL-2 for 24 hours before incubation with P815 cells and the indicated mAbs for 6 hours at E to T ratios of 1 and 5.

FIGS. 4A-4K show that CD28H synergizes with 2B4 and NKp46 for NK-cell activation and enhances activation through CD16. FIG. 4A: Representative contour plots of NK-cell degranulation induced by CD28H, 2B4, and NKp46, either alone or in combination, in redirected cytotoxicity assays. Freshly isolated NK cells were incubated with P815 cells and 5 μg/ml the indicated mAbs at 37° C. for 2 hours. The E to T ratio was 1:2. NK-cell degranulation was determined by staining for CD107a. A mAb to CD56 was a negative control for degranulation, whereas NKp46 and 2B4 co-engagement was a positive control for synergy of NK activating receptors. FIG. 4B: NK-degranulation as in FIG. 4A from several donors. Each symbol represents an independent donor (n=5). FIGS. 4C-4F: NK-cell degranulation upon co-engagement of CD28H with CD2 (FIG. 4C), DNAM-1 (FIG. 4D), NKG2D (FIG. 4E), and CD16 (FIG. 4F) in redirected cytotoxicity assays performed as in FIG. 4A. Each symbol represents an independent donor, n=4 in FIG. 4C, n=3 in FIG. 4D, n=4 in FIG. 4E, and n=5 in FIG. 4F. FIGS. 4G-4I: NK-cell degranulation as in FIG. 4A in redirected cytotoxicity assays. A fixed concentration (5 μg/ml) of mAbs to 2B4 (FIG. 4G), NKp46 (FIG. 4H) and CD16 (FIG. 4I) was used, and CD28H antibody was added at increasing concentrations. Each symbol represents an independent donor, n=5 in FIG. 4G, n=5 in FIG. 4H, n=6 in FIG. 4I. FIGS. 4J-4K: NK cells incubated with P815 cells and the indicated mAbs for 6 hours at various E to T ratios. Lysis of P815 cells induced by co-engagement of CD28H with 2B4 (FIG. 4J) or NKp46 (FIG. 4K); each graph represents one of two independent experiments. All data are presented as the mean±SEM. *P<0.05, **P<0.01, n.s., not-significant (Mann-Whitney test, two-tailed). All experiments were repeated at least twice.

FIGS. 5A and 5B show NK cell degranulation and cytokine production induced by B7H7 and CD48 on *Drosophila* S2 cells. FIG. 5A: Expression of CD48 and B7H7 on S2 cells transfected with CD48, B7H7, or both. Shaded histogram indicates staining of untransfected S2 cells. FIG. 5B: Pie charts represent the frequency of NK cells positive for the indicated number of responses. Arcs represent the proportion of NK cells positive for MIP-1α, IFN-γ, TNF-α and CD107a. Values represent mean of 3 donors.

FIGS. 6A-6F show NK-cell degranulation and cytokine production induced by B7H7 and CD48 on *Drosophila* S2 cells. FIG. 6A: Representative contour plots of NK-cell degranulation induced by S2 cells and S2 cells expressing B7H7, CD48, or both, after incubation for 2 hours at an E:T ratio of 1:2. Degranulation was determined by staining for CD56 and CD107a. FIG. 6B: NK-cell degranulation as in FIG. 6A from several donors. Each symbol represents an independent donor, n=5. FIGS. 6C-6F: Cytokine production by NK cells after incubation with the indicated S2 cells at 37° C. for 6 hours at an E:T ratio of 1:2. A mAb to CD28H (anti-CD28H) was included at 10 μg/ml to block the B7H7-CD28H interaction. Cells were stained for CD56 and CD107a, fixed and permeabilized, and stained for intracellular cytokines. Expression of IFNγ (FIG. 6C), TNFα (FIG. 6D), MIP-1α (FIG. 6E) and MIP-1β (FIG. 6F) in NK cells from multiple donors. Each symbol represents an independent donor, n=7 in FIG. 6C, n=5 in FIG. 6D, n=6 in FIG. 6E, and n=6 in FIG. 6 F. All data are presented as the mean±SEM. *P<0.05, P<0.01, *P<0.001 (Mann-Whitney test, two-tailed). All experiments have been repeated at least twice.

FIG. 7A: Representative contour plots of NK-cell degranulation induced by the indicated S2 cells in the presence of anti-S2 serum for 2 hours and measured by staining with fluorophore-conjugated CD56 and CD107a mAbs. FIG. 7B: Degranulation by NK cells as in FIG. 7A from multiple donors. Each symbol represents an independent donor, n=7. FIG. 7C: Staining for CD20 on 221 and Daudi cells. Shaded histograms indicate staining with isotype control. FIGS. 7D and 7E: Specific lysis of target cells by NK cells at effector to target cell ratio of 5:1 in the presence of 10 μg/ml Rituximab. Each symbol represents an independent donor, n=5 in both FIG. 7D and FIG. 7E. Target cells were 221 (FIG. 7D) and Daudi (FIG. 7E) cell lines, either untransfected or transfected with B7H7. A mAb to CD28H (anti-CD28H) was included at 10 g/ml to block the B7H7-CD28H interaction. All data are presented as the mean±SEM. *P<0.05 (Wilcoxon signed-rank test, paired, two-tailed). All experiments were repeated at least twice.

FIG. 8A: Staining for B7H7 and CD48 on Daudi, K562, and 221 cells. Shaded histograms represent staining with isotype controls. FIG. 8B: Expression of B7H7 on transfected 221 and Daudi cells. Shaded histograms represent staining of untransfected cells. FIG. 8C: Lysis of 221 and 221.B7H7 cells by resting NK cells at the indicated E to T ratios after 6 hours. A mAb to CD28H was added at 10 μg/ml to block the CD28H-B7H7 interaction (square symbols).

FIG. 9A: Tyrosine-phosphorylation of CD28H wild type and the indicated Tyr mutants upon pervanadate treatment. Transfected 293T cells were treated with pervanadate for 10 minutes. Cell lysates were immunoprecipitated with CD28H mAb. Phospho-tyrosine (4G10) and total CD28H (anti-2A) were detected by immunoblots. FIG. 9B: Lysis of P815 cells by NKL.CD28H cells at various E:T ratios in presence of the indicated mAbs after 6 hours. FIG. 9C: Lysis of P815 cells by NKL cell transfectants in presence of mAbs to 2B4 and CD28H at the indicated E:T ratios. NKL.CD28H-WT with mAb to 2B4 served as negative control (Ctrl). The graph represents one of two independent experiments. FIG. 9D: Lysis of 221.B7H7 cells by NKL cell transfectants at the indicated E:T ratios after 6 hours. Untransfected 221 cells served as negative control. The graph represents one of two independent experiments. FIG. 9E: Immunofluorescence staining with CD28H antibody of Daudi or Daudi-B7H7 cells incubated with NKL cells expressing CD28H wild-type or Y192F mutant. FIG. 9F: Fold change in fluorescence intensity of CD28H at the immunological synapse (IS), as compared to cell surface regions away from the synapse (non-IS), as in FIG. 9E. Each dot represents a single cell. Sample size (n) is shown in the figure. Data were obtained and combined from two independent experiments and presented as the mean±SEM. ****P<0.0001 (Mann-Whitney test, two-tailed). All experiments were repeated at least twice.

FIG. 11A: Either untreated or LPS- and poly(I:C)-stimulated human PBMC were gated on the CD14+ population and tested for B7H7 expression with fluorophore-conjugated B7H7 mAb. FIG. 11B: Expression of B7H7 in circulating myeloid dendritic cells. Human PBMC treated as in FIG. 11A were gated on lineage-negative (CD3−CD19−CD14−NKp46−) CD11c+ cells, and tested for expression of B7H7 by staining with B7H7 mAb. Shaded histograms represent staining with isotype control.

FIGS. 12A-12J show lysis of B7H7+ HLA-E+ HDLM-2 tumor cells by NKG2A+ NK cells expressing a CD28H-TCRζ chimeric antigen receptor. FIG. 12A: Design and expression of CD28H chimeric antigen receptors in NKL cells. Full-length or cytoplasmic-domain-deleted (ACD) CD28H was fused to the cytoplasmic domain of TCRζ and transfected into NKL cells. Cells were stained with fluorophore-conjugated CD28H mAb. Shaded histograms represent staining of untransfected NKL cells. FIGS. 12B-12C: Lysis of 221 cells (FIG. 12B) and 221.B7H7 cells (FIG. 12C) by transfected NKL cells at the indicated E:T ratio after 5 hours. FIG. 12D: Staining for HLA-E and B7H7 in 221.AEH and 221.AEH.B7H7 cells. Shaded histograms represent staining of untransfected 221 cells. FIG. 12E: Expression of NKG2A on NKL cells determined by immunostaining. Shaded histograms represent staining with IgG control. FIGS. 12F-12G: Lysis of 221.AEH cells (FIG. 12F) and 221.AEH.B7H7 cells (FIG. 12G) by transfected NKL cells at the indicated E:T ratios after 5 hours. The graph represents one of two independent experiments. FIG. 12H: Staining of B7H7 and HLA-E on HDLM-2 tumor cells. Shaded histograms represent staining with isotype controls. FIG. 12I: Expression of NKG2A on KHYG-1 cells determined by immunostaining (left). Lysis of HDLM-2 tumor cells by KHYG-1 cells after 5 hours, in the presence or absence of a blocking antibody to NKG2A (right). The graph represents one of two independent experiments. FIG. 12J: Lysis of HHLA-2+ HLA-E+ HDLM-2 tumor cells by transfected NKL cells at the indicated E:T ratio after 5 hours. All experiments have been repeated at least twice.

FIGS. 13A-13E show synergistic activation of NK cell degranulation by combinations of activating receptors, the design and expression of CD19.CARs, and lysis of CD19+ MHC-I+ tumor cells by NK cells expressing designed CD19.CARs. FIG. 13A: Degranulation of resting human NK cells induced by crosslinking combinations of NK-cell activating receptors. Crosslinking was performed in a redirected cytotoxicity assay using P815 cells in the presence of antibodies for the indicated activating receptors (n=2). FIG. 13B: Schematic diagram of CAR constructs using anti-CD19 scFv with a N-terminal myc-tag and a CD8α hinge as extracellular domain and the indicated combinations of transmembrane and signaling domains. FIG. 13C: Histograms showing expression of CAR constructs in NKL.2DL1 cells. FIG. 13D: Killing assays comparing lysis of target cells by the indicated CAR-expressing NKL.2DL1 cells. Either the mutated MHC-I negative lymphoblastoid cell line 221, or MHC-I (HLA-E or HLA-C/Cw15) transfected 221 cells were used as target (n=3). FIG. 13E: Comparing target-cell lysis by NKL.2DL1 cells expressing CAR2 or T-CAR (n=3). Same target cells were used as in FIG. 13D.

FIG. 15A: Schematic diagram of CAR constructs consisting of the extracellular domain of CD28H and the indicated combinations of signaling domains. FIG. 15B: Flow cytometry determination of expression of CD28H.T-CAR, CD28H.CAR2 and CD28H.CAR3 in NKL.2DL1 cells. FIG. 15C: Killing assays using CAR-transduced NKL.2DL1 cells as effector and 221.HLA-E cells or B7H7-transfected 221.HLA-E cells as targets (n=2). FIG. 15D: Lysis of 221.HLA-C(Cw15) cells or B7H7-transfected 221.HLA-C(Cw15) cells by NKL.2DL1 cells expressing CD28H.CARs (n=2).

FIG. 16A: Diagram of CAR stimulation by antibodies immobilized on beads. FIG. 16B: Western blot detection of activation signals in lysates of CARs-expressing NKL cells after stimulation by beads. The indicated antibodies were pre-bound to beads, and then incubated with CAR-NK cells for 10 min. Cell lysates were probed for the indicated signaling molecules. FIG. 16C: Western blot quantification of pErk/total-Erk and pPLCg1/total-PLCg1 ratios (n=2). FIG. 16D: Bead stimulation of NKL cells expressing T-CAR or CAR2. Co-incubation of beads and NK cells were performed for 10 minutes and 45 minutes, as indicated. Cell lysates were Western blotted with the indicated antibodies. FIG. 16E: Calcium mobilization induced in NKL cells expressing T-CAR or CAR2 after CAR-crosslinking with antibodies. NKL cells were preincubated with Myc-tag antibody on ice for 30 min and incubated at 37° C. for 5 min before the assay. Baseline calcium was measured for 30 s before addition of secondary goat-anti-mouse IgG antibodies for crosslinking.

Figure 13A:
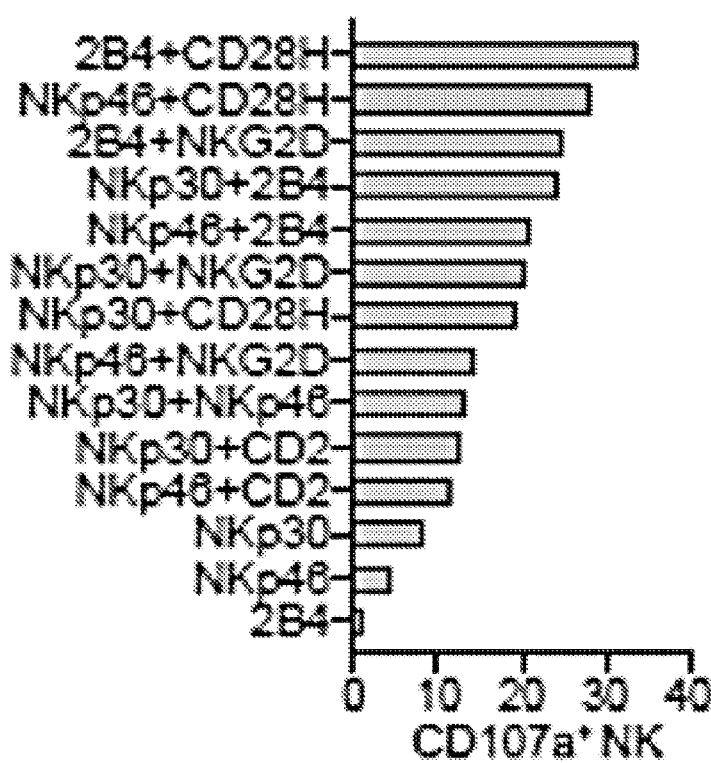
Figure 13B:
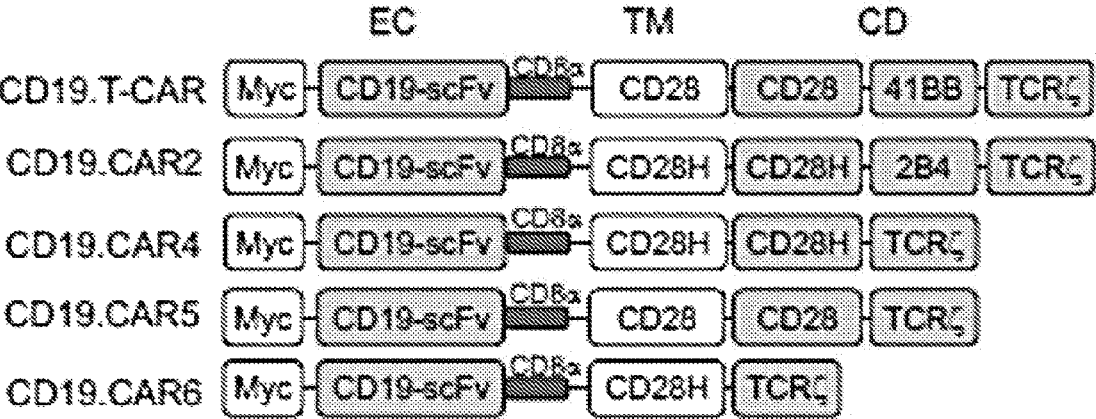
Figure 16C:
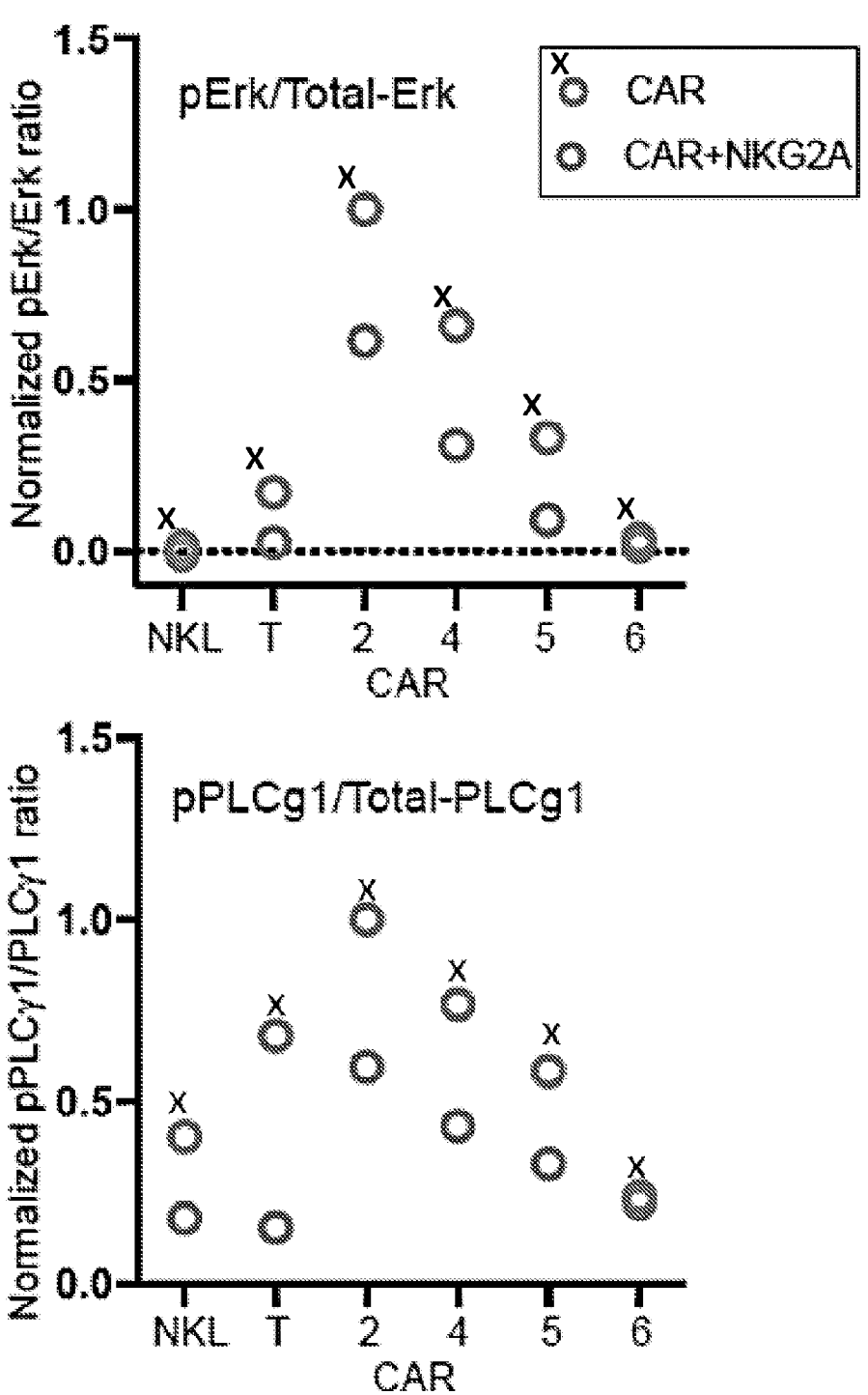
Figure 17:
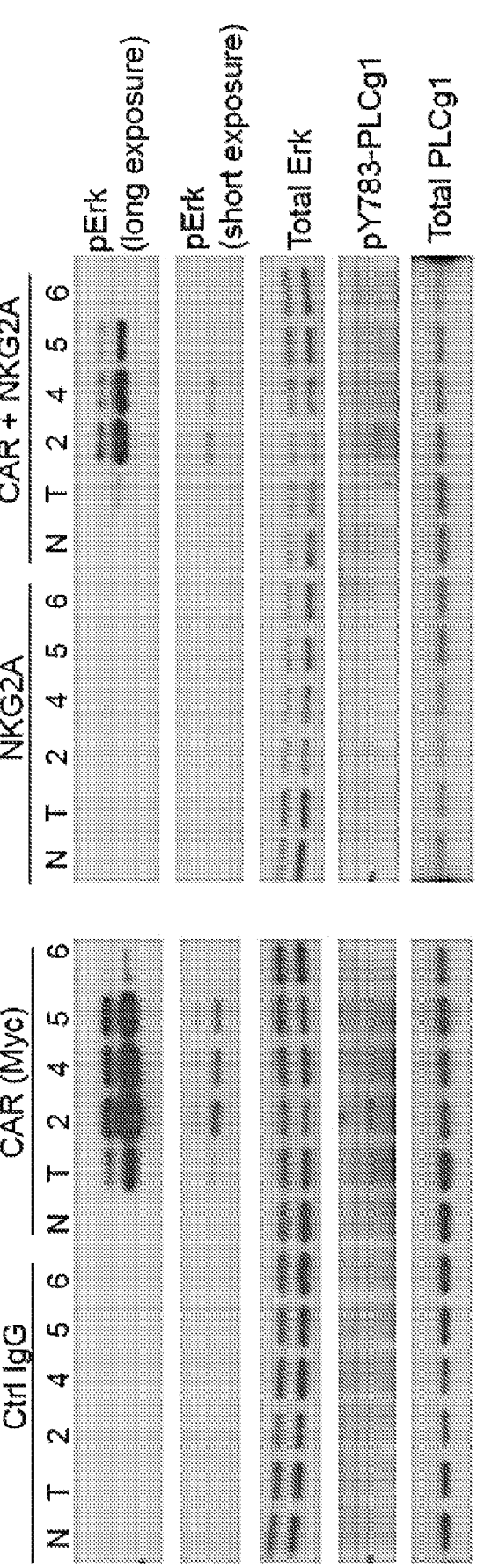

FIG. 17 shows stimulation of NKL cells expressing T-CAR and the CAR2 to CAR6 shown in FIG. 13B (N: no CAR). Beads coupled with the indicated antibodies were incubated with CAR-NK cells for 10 min at 37° C. Cell lysates were Western-blotted with antibodies for phosphorylated or total Erk and PLCγ1, as indicated. Quantification of band intensity is shown in FIG. 16C.

SEQUENCE LISTING

Any nucleic acid and amino acid sequences listed herein or in the accompanying sequence listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on Sep. 23, 2022, and is 73,149 bytes, which is incorporated by reference herein.

SEQ ID NO: 1 is the nucleic acid sequence of full-length CD28H fused with the cytoplasmic domain of TCRζ. CD28H: nucleotides 1-846; TCRζ: nucleotides 847-1185.

```
ATGGGGTCCCCGGGCATGGTGCTGGGCCTCCTGGTGCAGATCTGGGCCCT

GCAAGAAGCCTCAAGCCTGAGCGTGCAGCAGGGGCCCAACTTGCTGCAGG

TGAGGCAGGGCAGTCAGGCGACCCTGGTCTGCCAGGTGGACCAGGCCACA

GCCTGGGAACGGCTCCGTGTTAAGTGGACAAAGGATGGGGCCATCCTGTG

TCAACCGTACATCACCAACGGCAGCCTCAGCCTGGGGGTCTGCGGGCCCC

AGGGACGGCTCTCCTGGCAGGCACCCAGCCATCTCACCCTGCAGCTGGAC

CCTGTGAGCCTCAACCACAGCGGGGCGTACGTGTGCTGGGCGGCCGTAGA

GATTCCTGAGTTGGAGGAGGCTGAGGGCAACATAACAAGGCTCTTTGTGG

ACCCAGATGACCCCACACAGAACAGAAACCGGATCGCAAGCTTCCCAGGA

TTCCTCTTCGTGCTGCTGGGGGTGGGAAGCATGGGTGTGGCTGCGATCGT

GTGGGGTGCCTGGTTCTGGGGCCGCCGCAGCTGCCAGCAAAGGGACTCAG

GTAACAGCCCAGGAAATGCATTCTACAGCAACGTCCTATACCGGCCCCGG

GGGGCCCCAAAGAAGAGTGAGGACTGCTCTGGAGAGGGGAAGGACCAGAG

GGGCCAGAGCATTTATTCAACCTCCTTCCCGCAACCGGCCCCCGCCAGC

CGCACCTGGCGTCAAGACCCTGCCCCAGCCCGAGACCCTGCCCCAGCCCC

AGGCCCGGCCACCCCGTCTCTATGGTCAGGGTCTCTCCTAGACCAAGCCC

CACCCAGCAGCCGAGGCCAAAAGGGTTCCCCAAAGTGGGAGAGGAGagag tgaagttcagcaggagcgcagacgcccccgcgtaccagcagggccagaac
```

8

```
cagctctataacgagctcaatctaggacgaagagaggagtacgatgtttt ggacaagagacgtggccgggaccctgagatgggggggaaagccgcagagaa ggaagaaccctcaggaaggcctgtacaatgaactgcagaaagataagatg gcggaggcctacagtgagattgggatgaaaggcgagcgccggaggggcaa ggggcacgatggcctttaccagggtctcagtacagccaccaaggacacct acgacgcccttcacatgcaggccctgccccctcgc
```

SEQ ID NO: 2 is the amino acid sequence of full-length CD28H fused with the cytoplasmic domain of TCRζ. CD28H: amino acids 1-282; TCRζ: amino acids 283-395.

```
MGSPGMVLGLLVQIWALQEASSLSVQQGPNLLQVRQGSQATLVCQVDQAT

AWERLRVKWTKDGAILCOPYITNGSLSLGVCGPQGRLSWQAPSHLTLQLD

PVSLNHSGAYVCWAAVEIPELEEAEGNITRLFVDPDDPTQNRNRIASFPG

FLFVLLGVGSMGVAAIVWGAWFWGRRSCQQRDSGNSPGNAFYSNVLYRPR

GAPKKSEDCSGEGKDQRGQSIYSTSFPQPAPRQPHLASRPCPSPRPCPSP

RPGHPVSMVRVSPRPSPTQQPRPKGFPKVGEERVKFSRSADAPAYQQGQN

QLYNELNLGRREEYDVLDKRRGRDPEMGGKPQRRKNPQEGLYNELQKDKM

AEAYSEIGMKGERRRGKGHDGLYQGLSTATKDTYDALHMQALPPR
```

SEQ ID NO: 3 is the nucleic acid sequence of extracellular and transmembrane domains of CD28H fused with the cytoplasmic domain of TCRζ. CD28H: nucleotides 1-513; TCRζ: nucleotides 514-852.

```
ATGGGGTCCCCGGGCATGGTGCTGGGCCTCCTGGTGCAGATCTGGGCCCT

GCAAGAAGCCTCAAGCCTGAGCGTGCAGCAGGGGCCCAACTTGCTGCAGG

TGAGGCAGGGCAGTCAGGCGACCCTGGTCTGCCAGGTGGACCAGGCCACA

GCCTGGGAACGGCTCCGTGTTAAGTGGACAAAGGATGGGGCCATCCTGTG

TCAACCGTACATCACCAACGGCAGCCTCAGCCTGGGGGTCTGCGGGCCCC

AGGGACGGCTCTCCTGGCAGGCACCCAGCCATCTCACCCTGCAGCTGGAC

CCTGTGAGCCTCAACCACAGCGGGGCGTACGTGTGCTGGGCGGCCGTAGA

GATTCCTGAGTTGGAGGAGGCTGAGGGCAACATAACAAGGCTCTTTGTGG

ACCCAGATGACCCCACACAGAACAGAAACCGGATCGCAAGCTTCCCAGGA

TTCCTCTTCGTGCTGCTGGGGGTGGGAAGCATGGGTGTGGCTGCGATCGT

GTGGGGTGCCTGGagagtgaagttcagcaggagcgcagacgcccccgcgt accagcagggccagaaccagctctataacgagctcaatctaggacgaaga gaggagtacgatgttttggacaagagacgtggccgggaccctgagatggg gggaaagccgcagagaaggaagaaccctcaggaaggcctgtacaatgaac tgcagaaagataagatggcggaggcctacagtgagattgggatgaaaggc gagcgccggaggggcaaggggcacgatggcctttaccagggtctcagtac agccaccaaggacacctacgacgcccttcacatgcaggccctgccccctc gc
```

SEQ ID NO: 4 is the amino acid sequence of extracellular and transmembrane domains of CD28H fused with the cytoplasmic domain of TCRζ. CD28H: amino acids 1-171; TCRζ: amino acids 172-284.

MGSPGMVLGLLVQIWALQEASSLSVQQGPNLLQVRQGSQATLVCQVDQAT

AWERLRVKWTKDGAILCQPYINGSLSLGVCGPQGRLSWQAPSHLTLQLDP

VSLNHSGAYVCWAAVEIPELEEAEGNITRLFVDPDDPTQNRNRIASFPGF

LFVLLGVGSMGVAAIVWGAWRVKFSRSADAPAYQQGQNQLYNELNLGRRE

EYDVLDKRRGRDPEMGGKPQRRKNPQEGLYNELQKDKMAEAYSEIGMKGE

RRRGKGHDGLYQGLSTATKDTYDALHMQALPPR

SEQ ID NO: 5 is the nucleic acid sequence of full-length CD28H fused with the intracellular domains of 2B4 and TCRζ. The DNA sequence of CD28H was codon-optimized for synthesis as a gBlock fragment. CD28H: nucleotides 1-846; 2B4: nucleotides 847-1206; TCRζ: nucleotides 1207-1545.

ATGGGGTCCCCGGGCATGGTGCTGGGCCTCCTGGTGCAGATCTGGGCCCT

GCAAGAAGCCTCAAGCCTGAGCGTGCAGCAGGGGCCCAACTTGCTGCAGG

TGAGGCAGGGCAGTCAGGCGACCCTGGTCTGCCAGGTGGACCAGGCCACA

GCCTGGGAACGGCTCCGTGTTAAGTGGACAAAGGATGGGGCCATCCTGTG

TCAACCGTACATCACCAACGGCAGCCTCAGCCTGGGGGTCTGCGGGCCCC

AGGGACGGCTCTCCTGGCAGGCACCCAGCCATCTCACCCTGCAGCTGGAC

CCTGTGAGCCTCAACCACAGCGGGGCGTACGTGTGCTGGGCGGCCGTAGA

GATTCCTGAGTTGGAGGAGGCTGAGGGCAACATAACAAGGCTCTTTGTGG

ACCCAGATGACCCCACACAGAACAGAAACCGGATCGCAAGCTTCCCAGGA

TTCCTCTTCGTGCTGCTGGGGGTGGGAAGCATGGGTGTGGCTGCGATCGT

GTGGGGTGCCTGGTTCTGGGGCCGCCGCAGCTGCCAGCAAAGGGACTCAG

GTAACAGCCCAGGAAATGCATTCTACAGCAACGTCCTATACCGGCCCCGG

GGGGCCCCAAAGAAGAGTGAGGACTGCTCTGGAGAGGGGAAGGACCAGAG

GGGCCAGAGCATTTATTCAACCAGTTTCCCTCAACCGGCTCCAAGACAAC

CACATCTCGCCAGTCGGCCTTGTCCGTCCCCTAGACCCTGCCCCAGTCCC

AGGCCCGGCCACCCCGTCTCTATGGTCAGGGTCTCTCCTAGACCAAGCCC

CACCCAGCAGCCGAGGCCAAAAGGGTTCCCCAAAGTGGGAGAGGAGTGGA

GGAGAAAGAGGAAGGAGAAGCAGTCAGAGACCAGTCCCAAGGAATTTTTG

ACAATTTACGAAGATGTCAAGGATCTGAAAACCAGGAGAAATCACGAGCA

GGAGCAGACTTTTCCTGGAGGGGGGAGCACCATCTACTCTATGATCCAGT

CCCAGTCTTCTGCTCCCACGTCACAAGAACCTGCATATACATTATATTCA

TTAATTCAGCCTTCCAGGAAGTCTGGATCCAGGAAGAGGAACCACAGCCC

TTCCTTCAATAGCACTATCTATGAAGTGATTGGAAAGAGTCAACCTAAAG

CCCAGAACCCTGCTCGATTGAGCCGCAAAGAGCTGGAGAACTTTGATGTT

TATTCCagagtgaagttcagcaggagcgcagacgcccccgcgtaccagca gggccagaaccagctctataacgagctcaatctaggacgaagagaggagt acgatgtttttggacaagagacgtggccgggaccctgagatggggggaaag ccgcagagaaggaagaaccctcaggaaggcctgtacaatgaactgcagaa agataagatggcggaggcctacagtgagattgggatgaaaggcgagcgcc ggaggggcaaggggcacgatggcctttaccagggtctcagtacagccacc aaggacacctacgacgcccttcacatgcaggccctgccccctcgc SEQ ID NO: 6 is the amino acid sequence of full-length CD28H fused with the intracellular domains of 2B4 and TCRζ. CD28H: amino acids 1-282; 2B4: amino acids 283-402; TCRζ: amino acids 403-515.

MGSPGMVLGLLVQIWALQEASSLSVQQGPNLLQVRQGSQATLVCQVDQAT

AWERLRVKWTKDGAILCQPYITNGSLSLGVCGPQGRLSWQAPSHLTLQLD

PVSLNHSGAYVCWAAVEIPELEEAEGNITRLFVDPDDPTQNRNRIASFPG

FLFVLLGVGSMGVAAIVWGAWFWGRRSCQQRDSGNSPGNAFYSNVLYRPR

GAPKKSEDCSGEGKDQRGQSIYSTSFPQPAPRQPHLASRPCPSPRPCPSP

RPGHPVSMVRVSPRPSPTQQPRPKGFPKVGEEWRRKRKEKQSETSPKEFL

TIYEDVKDLKTRRNHEQEQTFPGGGSTIYSMIQSQSSAPTSQEPAYTLYS

LIQPSRKSGSRKRNHSPSFNSTIYEVIGKSQPKAQNPARLSRKELENFDV

YSRVKFSRSADAPAYQQGQNQLYNELNLGRREEYDVLDKRRGRDPEMGGK

PQRRKNPQEGLYNELQKDKMAEAYSEIGMKGERRRGKGHDGLYQGLSTAT

KDTYDALHMQALPPR

SEQ ID NO: 7 is the nucleic acid sequence of extracellular domain of CD28H fused with the transmembrane domain of CD28 and intracellular domains of CD28, 41BB, and TCRζ. CD28H: nucleotides 1-450; CD28: nucleotides 451-654; 4-1BB: nucleotides 655-780; TCRζ: nucleotides 781-1119.

ATGGGGTCCCCGGGCATGGTGCTGGGCCTCCTGGTGCAGATCTGGGCCCT

GCAAGAAGCCTCAAGCCTGAGCGTGCAGCAGGGGCCCAACTTGCTGCAGG

TGAGGCAGGGCAGTCAGGCGACCCTGGTCTGCCAGGTGGACCAGGCCACA

GCCTGGGAACGGCTCCGTGTTAAGTGGACAAAGGATGGGGCCATCCTGTG

TCAACCGTACATCACCAACGGCAGCCTCAGCCTGGGGGTCTGCGGGCCCC

AGGGACGGCTCTCCTGGCAGGCACCCAGCCATCTCACCCTGCAGCTGGAC

CCTGTGAGCCTCAACCACAGCGGGGCGTACGTGTGCTGGGCGGCCGTAGA

GATTCCTGAGTTGGAGGAGGCTGAGGGCAACATAACAAGGCTCTTTGTGG

ACCCAGATGACCCCACACAGAACAGAAACCGGATCGCAAGCTTCCCAGGA

TTTTGGGTGCTGGTGGTGGTTGGTGGAGTCCTGGCTTGCTATAGCTTGCT

AGTAACAGTGGCCTTTATTATTTTCTGGGTGAGGAGTAAGAGGAGCAGGC

TCCTGCACAGTGACTACATGAACATGACTCCCCGCCGCCCCGGGCCCACC

CGCAAGCATTACCAGCCCTATGCCCCACCACGCGACTTCGCAGCCTATCG

CTCCAAACGGGGCAGAAAGAAACTCCTGTATATATTCAAACAACCATTTA

TGAGACCAGTACAAACTACTCAAGAGGAAGATGGCTGTAGCTGCCGATTT

CCAGAAGAAGAAGAAGGAGGATGTGAACTGagagtgaagttcagcaggag cgcagacgcccccgcgtaccagcagggccagaaccagctctataacgagc tcaatctaggacgaagagaggagtacgatgtttttggacaagagacgtggc cgggaccctgagatggggggaaagccgcagagaaggaagaaccctcagga -continued aggcctgtacaatgaactgcagaaagataagatggcggaggcctacagtg agattgggatgaaaggcgagcgccggaggggcaaggggcacgatggcctt taccagggtctcagtacagccaccaaggacacctacgacgcccttcacat gcaggccctgccccctcgc SEQ ID NO: 8 is the amino acid sequence of extracellular domain of CD28H fused with the transmembrane domain of CD28 and intracellular domains of CD28, 4-1BB, and TCRζ. CD28H: amino acids 1-150; CD28: amino acids 151-218; 4-1BB: amino acids 219-260; TCRζ: nucleotides 261-373.

MGSPGMVLGLLVQIWALQEASSLSVQQGPNLLQVRQGSQATLVCQVDQAT

AWERLRVKWTKDGAILCQPYITNGSLSLGVCGPQGRLSWQAPSHLTLQLD

PVSLNHSGAYVCWAAVEIPELEEAEGNITRLFVDPDDPTQNRNRIASFPG

FWVLVVVGGVLACYSLLVTVAFIIFWVRSKRSRLLHSDYMNMTPRRPGPT

RKHYQPYAPPRDFAAYRSKRGRKKLLYIFKQPFMRPVQTTQEEDGCSCRF

PEEEEGGCELRVKFSRSADAPAYQQGQNQLYNELNLGRREEYDVLDKRRG

RDPEMGGKPQRRKNPQEGLYNELQKDKMAEAYSEIGMKGERRRGKGHDGL

YQGLSTATKDTYDALHMQALPPR

SEQ ID NO: 9 is the nucleic acid sequence of extracellular domain of CD28H fused with the transmembrane domain of NKG2D and intracellular domains of 2B4 and TCRζ. CD28H: nucleotides 1-450; NKG2D: nucleotides 451-513; 2B4: nucleotides 514-873; TCRζ: nucleotides 874-1212.

ATGGGGTCCCCGGGCATGGTGCTGGGCCTCCTGGTGCAGATCTGGGCCCT

GCAAGAAGCCTCAAGCCTGAGCGTGCAGCAGGGGCCCAACTTGCTGCAGG

TGAGGCAGGGCAGTCAGGCGACCCTGGTCTGCCAGGTGGACCAGGCCACA

GCCTGGGAACGGCTCCGTGTTAAGTGGACAAAGGATGGGGCCATCCTGTG

TCAACCGTACATCACCAACGGCAGCCTCAGCCTGGGGGTCTGCGGGCCCC

AGGGACGGCTCTCCTGGCAGGCACCCAGCCATCTCACCCTGCAGCTGGAC

CCTGTGAGCCTCAACCACAGCGGGGCGTACGTGTGCTGGGCGGCCGTAGA

GATTCCTGAGTTGGAGGAGGCTGAGGGCAACATAACAAGGCTCTTTGTGG

ACCCAGATGACCCCACACAGAACAGAAACCGGATCGCAAGCTTCCCAGGA

CCATTTTTTTTCTGCTGCTTCATCGCTGTAGCCATGGGAATCCGTTTCAT

TATTATGGTAACATGGAGGAGAAAGAGGAAGGAGAAGCAGTCAGAGACCA

GTCCCAAGGAATTTTTGACAATTTACGAAGATGTCAAGGATCTGAAAACC

AGGAGAAATCACGAGCAGGAGCAGACTTTTCCTGGAGGGGGGGAGCACCAT

CTACTCTATGATCCAGTCCCAGTCTTCTGCTCCCACGTCACAAGAACCTG

CATATACATTATATTCATTAATTCAGCCTTCCAGGAAGTCTGGATCCAGG

AAGAGGAACCACAGCCCTTCCTTCAATAGCACTATCTATGAAGTGATTGG

AAAGAGTCAACCTAAAGCCCAGAACCCTGCTCGATTGAGCCGCAAAGAGC

TGGAGAACTTTGATGTTTATTCCagagtgaagttcagcaggagcgcagac

-continued gcccccgcgtaccagcagggccagaaccagctctataacgagctcaatct aggacgaagagaggagtacgatgttttggacaagagacgtggccgggacc ctgagatggggggaaagccgcagagaaggaagaaccctcaggaaggcctg tacaatgaactgcagaaagataagatggcggaggcctacagtgagattgg gatgaaaggcgagcgccggaggggcaaggggcacgatggcctttaccagg gtctcagtacagccaccaaggacacctacgacgcccttcacatgcaggcc ctgccccctcgc SEQ ID NO: 10 is the amino acid sequence of extracellular domain of CD28H fused with the transmembrane domain of NKG2D and intracellular domains of 2B4 and TCRζ. CD28H: amino acids 1-150; NKG2D: amino acids 151-171; 2B4: amino acids 172-291; TCRζ: nucleotides 292-404.

MGSPGMVLGLLVQIWALQEASSLSVQQGPNLLQVRQGSQATLVCQVDQAT

AWERLRVKWTKDGAILCQPYITNGSLSLGVCGPQGRLSWQAPSHLTLQLD

PVSLNHSGAYVCWAAVEIPELEEAEGNITRLFVDPDDPTQNRNRIASFPG

PFFFCCFIAVAMGIRFIIMVTWRRKRKEKQSETSPKEFLTIYEDVKDLKT

RRNHEQEQTFPGGGSTIYSMIQSQSSAPTSQEPAYTLYSLIQPSRKSGSR

KRNHSPSENSTIYEVIGKSQPKAQNPARLSRKELENFDVYSRVKFSRSAD

APAYQQGQNQLYNELNLGRREEYDVLDKRRGRDPEMGGKPQRRKNPQEGL

YNELQKDKMAEAYSEIGMKGERRRGKGHDGLYQGLSTATKDTYDALHMQA

LPPR

SEQ ID NO: 11 is the nucleic acid sequence of CD19 scFv, followed by a CD8α hinge domain fused to the transmembrane domain of CD28H and signaling domains of CD28H, 2B4, and TCRζ. This construct includes an N-terminal Myc tag. DNA sequence of CD8α and CD28H portions were codon-optimized for synthesis as a gBlock fragment. Signal peptide: nucleotides 1-63; Myc tag: nucleotides 64-93; CD19 scFv: nucleotides 94-819; CD8α hinge: 820-954; CD28H transmembrane and signaling domains: nucleotides 955-1350; 2B4: nucleotides 1351-1710; TCRζ: nucleotides 1711-2049.

atggcgctccctgtcaccgcactgcttcttccgctggcactgctgctgc acgctgcacggcctgagcaaaaacttatctctgaagaggacctcgatat acagatgacgcagacaacgtcaagtctttccgccagcttgggagaccga gtgactatatcttgtagagcaagccaggatatttctaagtatcttaact ggtaccaacaaaagcccgatggaacggttaagctgcttatataccatac cagtagactccactccggcgtaccatcacggttttctggcagtggctcc gggaccgactattctttgacgatctctaatctcgaacaagaggatattg caacatactttgtcagcaaggcaataccttgccatatacgtttggggg gggacaaaacttgagataaccggcggcggtggttcaggcggtggcggtt ccggtggtgggggatcagaggttaagcttcaggaatccggaccaggttt ggttgcccccagccaatctctcagcgttacatgcacggtttcaggcgtc agtctccccgattacggtgtaagttggattcggcaacctccgcgaaagg -continued gtctggaatggctggggggttatttgggggagtgagacaacttattacaa ctctgcacttaagagtcggcttaccatcatcaaggataattcaaaatca caagtattcctgaagatgaactcattgcaaacagatgatacagctatat actattgtgccaagcattactattatggtggttcttatgcaatggatta ctggggcaaggcacgtcagtgacagtgagttcaACCACCACCCCTGCA

CCAAGACCTCCAACTCCTGCCCCAACTATTGCAAGTCAGCCACTTTCTT

TGCGACCAGAGGCGTGCCGGCCAGCGGCGGGGGGCGCAGTGCACACGAG

GGGGCTGGACTTCGCCTGTGATTTCCTCTTCGTGCTGCTGGGGGTGGGA

AGCATGGGTGTGGCTGCGATCGTGTGGGGTGCCTGGTTCTGGGGCCGCC

GCAGCTGCCAGCAAAGGGACTCAGGTAACAGCCCAGGAAATGCATTCTA

CAGCAACGTCCTATACCGGCCCCGGGGGGCCCCAAAGAAGAGTGAGGAC

TGCTCTGGAGAGGGGAAGGACCAGAGGGGCCAGAGCATTTATTCAACCA

GTTTCCCTCAACCGGCTCCAAGACAACCACATCTCGCCAGTCGGCCTTG

TCCGTCCCCTAGACCCTGCCCCAGTCCCAGGCCCGGCCACCCCGTCTCT

ATGGTCAGGGTCTCTCCTAGACCAAGCCCCACCCAGCAGCCGAGGCCAA

AAGGGTTCCCCAAAGTGGGAGAGGAGTGGAGGAGAAAGAGGAAGGAGAA

GCAGTCAGAGACCAGTCCCAAGGAATTTTTGACAATTTACGAAGATGTC

AAGGATCTGAAAACCAGGAGAAATCACGAGCAGGAGCAGACTTTTCCTG

GAGGGGGGAGCACCATCTACTCTATGATCCAGTCCCAGTCTTCTGCTCC

CACGTCACAAGAACCTGCATATACATTATATTCATTAATTCAGCCTTCC

AGGAAGTCTGGATCCAGGAAGAGGAACCACAGCCCTTCCTTCAATAGCA

CTATCTATGAAGTGATTGGAAAGAGTCAACCTAAAGCCCAGAACCCTGC

TCGATTGAGCCGCAAAGAGCTGGAGAACTTTGATGTTTATTCCagagtg aagttcagcaggagcgcagacgcccccgcgtaccagcagggccagaacc agctctataacgagctcaatctaggacgaagagaggagtacgatgtttt ggacaagagacgtggccgggaccctgagatggggggaaagccgcagaga aggaagaaccctcaggaaggcctgtacaatgaactgcagaaagataaga tggcggaggcctacagtgagattgggatgaaaggcgagcgccggagggg caaggggcacgatgcctttaccaggtctcagtacagccaccaaggac acctacgacgcccttcacatgcaggccctgccccctcgc SEQ ID NO: 12 is the amino acid sequence of CD19 scFv, followed by a CD8α hinge domain fused to the transmembrane domain of CD28H and signaling domains of CD28H, 2B4, and TCRζ. This construct includes an N-terminal Myc tag. Signal peptide: amino acids 1-21; Myc tag: amino acids 22-31; CD19 scFv: amino acids 32-273; CD8α hinge: 274-318; CD28H transmembrane and signaling domains: amino acids 319-450; 2B4: amino acids 451-570; TCRζ: amino acids 571-683.

MALPVTALLLPLALLLHAARPEQKLISEEDLDIQMTQTTSSLSASLGDR

VTISCRASQDISKYLNWYQQKPDGTVKLLIYHTSRLHSGVPSRFSGSGS

GTDYSLTISNLEQEDIATYFCQQGNTLPYTFGGGTKLEITGGGGSGGGG

GGGGSEVKLQESGPGLVAPSQSLSVTCTVSGVSLPDYGVSWIRQPPRKG

-continued

LEWLGVIWGSETTYYNSALKSRLTIIKDNSKSQVFLKMNSLQTDDTAIY

YCAKHYYYGGSYAMDYWGQGTSVTVSSTTTPAPRPPTPAPTIASQPLSL

RPEACRPAAGGAVHTRGLDFACDELFVLLGVGSMGVAAIVWGAWFWGRR

SCQQRDSGNSPGNAFYSNVLYRPRGAPKKSEDCSGEGKDQRGQSIYSTS

FPQPAPRQPHLASRPCPSPRPCPSPRPGHPVSMVRVSPRPSPTQQPRPK

GFPKVGEEWRRKRKEKQSETSPKEFLTIYEDVKDLKTRRNHEQEQTFPG

GGSTIYSMIQSQSSAPTSQEPAYTLYSLIQPSRKSGSRKRNHSPSENST

IYEVIGKSQPKAQNPARLSRKELENFDVYSRVKFSRSADAPAYQQGQNQ

LYNELNLGRREEYDVLDKRRGRDPEMGGKPQRRKNPQEGLYNELQKDKM

AEAYSEIGMKGERRRGKGHDGLYQGLSTATKDTYDALHMQALPPR

SEQ ID NO: 13 is the nucleic acid sequence of CD19 scFv, followed by a CD8α hinge domain fused to the transmembrane domain of CD28 and signaling domains of CD28, 4-1BB, and TCRζ. This construct includes an N-terminal Myc tag. DNA sequence of CD8α was codon-optimized for synthesis as a gBlock fragment. Signal peptide: nucleotides 1-63; Myc tag: nucleotides 64-93; CD19 scFv: nucleotides 94-819; CD8α hinge: nucleotides 820-954; CD28 transmembrane and signaling domains: nucleotides 955-1158; 4-1BB: nucleotides 1159-1284; TCRζ: nucleotides 1285-1623.

atggcgctccctgtcaccgcactgcttcttccgctggcactgctgctgc acgctgcacggcctgagcaaaaacttatctctgaagaggacctcgatat acagatgacgcagacaacgtcaagtctttccgccagcttgggagaccga gtgactatatcttgtagagcaagccaggatatttctaagtatcttaact ggtaccaacaaaagcccgatggaacggttaagctgctttatataccatac cagtagactccactccggcgtaccatcacggttttctggcagtggctcc gggaccgactattctttgacgatctctaatctcgaacaagaggatattg caacatactttgtcagcaaggcaataccttgccatatacgtttggggg gggacaaaacttgagataaccggcggcggtggttcaggcggtggcggtt ccggtggtgggggatcagaggttaagcttcaggaatccggaccaggttt ggttgcccccagccaatctctcagcgttacatgcacggtttcaggcgtc agtctccccgattacggtgtaagttggattcggcaacctccgcgaaagg gtctggaatggctggggggttatttgggggagtgagacaacttattacaa ctctgcacttaagagtcggcttaccatcatcaaggataattcaaaatca caagtattcctgaagatgaactcattgcaaacagatgatacagctatat actattgtgccaagcattactattatggtggttcttatgcaatggatta ctggggcaaggcacgtcagtgacagtgagttcaACCACCACCCCTGCA

CCAAGACCTCCAACTCCTGCCCCAACTATTGCAAGTCAGCCACITTCTT

TGCGACCAGAGGCGTGCCGGCCAGCGGCGGGGGGCGCAGTGCACACGAG

GGGGCTGGACTTCGCCTGTGATTTTTGGGTGCTGGTGGTGGTTGGTGGA

GTCCTGGCTTGCTATAGCTTGCTAGTAACAGTGGCCTTTATTATTTTCT

GGGTGAGGAGTAAGAGGAGCAGGCTCCTGCACAGTGACTACATGAACAT

-continued

GACTCCCCGCCGCCCCGGGCCCACCCGCAAGCATTACCAGCCCTATGCC

CCACCACGCGACTTCGCAGCCTATCGCTCCAAACGGGGCAGAAAGAAAC

TCCTGTATATATTCAAACAACCATTTATGAGACCAGTACAAACTACTCA

AGAGGAAGATGGCTGTAGCTGCCGATTTCCAGAAGAAGAAGAAGGAGGA

TGTGAACTGagagtgaagttcagcaggagcgcagacgcccccgcgtacc agcagggccagaaccagctctataacgagctcaatctaggacgaagaga ggagtacgatgtttggacaagagacgtggccgggaccctgagatgggg ggaaagccgcagagaaggaagaaccctcaggaaggcctgtacaatgaac tgcagaaagataagatggcggaggcctacagtgagattgggatgaaagg cgagcgccggaggggcaaggggcacgatggcctttaccagggtctcagt acagccaccaaggacacctacgacgcccttcacatgcaggccctgcccc ctcgc SEQ ID NO: 14 is the amino acid sequence of CD19 scFv, followed by a CD8α hinge domain fused to the transmembrane domain of CD28 and signaling domains of CD28, 4-1BB, and TCRζ. This construct includes an N-terminal Myc tag. Signal peptide: amino acids 1-21; Myc tag: amino acids 22-31; CD19 scFv: amino acids 32-273; CD8α hinge: amino acids 274-318; CD28 transmembrane and signaling domains: amino acids 319-386; 4-1BB: amino acids 387-428; TCRζ: amino acids 429-541.

MALPVTALLLPLALLLHAARPEQKLISEEDLDIQMTQTTSSLSASLGDR

VTISCRASQDISKYLNWYQQKPDGTVKLLIYHTSRLHSGVPSRFSGSGS

GTDYSLTISNLEQEDIATYFCQQGNTLPYTFGGGTKLEITGGGGSGGGG

SGGGGSEVKLQESGPGLVAPSQSLSVTCTVSGVSLPDYGVSWIRQPPRK

GLEWLGVIWGSETTYYNSALKSRLTIIKDNSKSQVFLKMNSLQTDDTAI

YYCAKHYYYGGSYAMDYWGQGTSVTVSSTTTPAPRPPTPAPTIASQPLS

LRPEACRPAAGGAVHTRGLDFACDEWVLVVVGGVLACYSLLVTVAFIIF

WVRSKRSRLLHSDYMNMTPRRPGPTRKHYQPYAPPRDFAAYRSKRGRKK

LLYIFKQPFMRPVQTTQEEDGCSCRFPEEEEGGCELRVKFSRSADAPAY

QQGQNQLYNELNLGRREEYDVLDKRRGRDPEMGGKPQRRKNPQEGLYNE

LQKDKMAEAYSEIGMKGERRRGKGHDGLYQGLSTATKDTYDALHMQALP
PR

SEQ ID NO: 15 is the nucleic acid sequence of CD19 scFv, followed by a CD8α hinge domain fused to the transmembrane domain of CD28H and signaling domains of CD28H and TCRζ. This construct includes an N-terminal Myc tag. DNA sequence of CD8α and CD28H portions were codon-optimized for synthesis as a gBlock fragment. Signal peptide: nucleotides 1-63; Myc tag: nucleotides 64-93; CD19 scFv: nucleotides 94-819; CD8α hinge: nucleotides 820-954; CD28H transmembrane domain: nucleotides 955-1017; CD28H signaling domain: nucleotides 1018-1350; TCRζ: nucleotides 1351-1689.

atggcgctccctgtcaccgcactgcttcttccgctggcactgctgctgc acgctgcacggcctgagcaaaaacttatctctgaagaggacctcgatat -continued acagatgacgcagacaacgtcaagtctttccgccagcttgggagaccga gtgactatatcttgtagagcaagccaggatatttctaagtatcttaact ggtaccaacaaaagcccgatggaacggttaagctgcttatataccatac cagtagactccactccggcgtaccatcacggttttctggcagtggctcc gggaccgactattctttgacgatctctaatctcgaacaagaggatattg caacatacttttgtcagcaaggcaataccttgccatatacgtttggggg gggacaaaacttgagataaccggcggcggtggttcaggcggtggcggtt ccggtggtgggggatcagaggttaagcttcaggaatccggaccaggttt ggttgcccccagccaatctctcagcgttacatgcacggtttcaggcgtc agtctccccgattacggtgtaagttggattcggcaacctccgcgaaagg gtctggaatggctgggggttatttgggggagtgagacaacttattacaa ctctgcacttaagagtcggcttaccatcatcaaggataattcaaaatca caagtattcctgaagatgaactcattgcaaacgatgatacagctatat actattgtgccaagcattactattatggtggttcttatgcaatggatta ctgggggcaaggcacgtcagtgacagtgagttcaACCACCACCCCTGCA

CCAAGACCTCCAACTCCTGCCCCAACTATTGCAAGTCAGCCACTTTCTT

TGCGACCAGAGGCGTGCCGGCCAGCGGCGGGGGGCGCAGTGCACACGAG

GGGGCTGGACTTCGCCTGTGATTTCCTCTTCGTGCTGCTGGGGGTGGGA

AGCATGGGTGTGGCTGCGATCGTGTGGGGTGCCTGGTTCTGGGGCCGCC

GCAGCTGCCAGCAAAGGGACTCAGGTAACAGCCCAGGAAATGCATTCTA

CAGCAACGTCCTATACCGGCCCCGGGGGGCCCCAAAGAAGAGTGAGGAC

TGCTCTGGAGAGGGGAAGGACCAGAGGGGCCAGAGCATTTATTCAACCA

GTTTCCCTCAACCGGCTCCAAGCAACCACATCTCGCCAGTCGGCCTTG

TCCGTCCCCTAGACCCTGCCCCAGTCCCAGGCCCGGCCACCCCGTCTCT

ATGGTCAGGGTCTCTCCTAGACCAAGCCCCACCCAGCAGCCGAGGCCAA

AAGGGTTCCCCAAAGTGGGAGAGGAGagagtgaagttcagcaggagcgc agacgcccccgcgtaccagcagggccagaaccagctctataacgagctc aatctaggacgaagagaggagtacgatgtttttggacaagagacgtggcc gggaccctgagatggggggaaagccgcagagaaggaagaaccctcagga aggcctgtacaatgaactgcagaaagataagatggcggaggcctacagt gagattgggatgaaaggcgagcgccggaggggcaaggggcacgatggcc tttaccagggtctcagtacagccaccaaggacacctacgacgcccttca catgcaggccctgcccctcgc SEQ ID NO: 16 is the amino acid sequence of CD19 scFv, followed by a CD8α hinge domain fused to the transmembrane domain of CD28H and signaling domains of CD28H and TCRζ. This construct includes an N-terminal Myc tag. Signal peptide: amino acids 1-21; Myc tag: amino acids 22-31; CD19 scFv: amino acids 32-273; CD8α hinge: amino acids 274-318; CD28H transmembrane domain: amino acids 319-339; CD28H signaling domain: amino acids 340-450; TCRζ: amino acids 451-563.

MALPVTALLLPLALLLHAARPEQKLISEEDLDIQMTQTTSSLSASLGDR

VTISCRASQDISKYLNWYQQKPDGTVKLLIYHTSRLHSGVPSRFSGSGS

GTDYSLTISNLEQEDIATYFCQQGNTLPYTFGGGTKLEITGGGGSGGGG

SGGGGSEVKLQESGPGLVAPSQSLSVTCTVSGVSLPDYGVSWIRQPPRK

GLEWLGVIWGSETTYYNSALKSRLTIIKDNSKSQVFLKMNSLQTDDTAI

YYCAKHYYYGGSYAMDYWGQGTSVTVSSTTTPAPRPPTPAPTIASQPLS

LRPEACRPAAGGAVHTRGLDFACDELFVLLGVGSMGVAAIVWGAWFWGR

RSCQQRDSGNSPGNAFYSNVLYRPRGAPKKSEDCSGEGKDQRGQSIYST

SFPQPAPRQPHLASRPCPSPRPCPSPRPGHPVSMVRVSPRPSPTQQPRP

KGFPKVGEERVKFSRSADAPAYQQGQNQLYNELNLGRREEYDVLDKRRG

RDPEMGGKPQRRKNPQEGLYNELQKDKMAEAYSEIGMKGERRRGKGHDG

LYQGLSTATKDTYDALHMQALPPR

SEQ ID NO: 17 is the nucleic acid sequence of CD19 scFv, followed by a CD8α hinge domain fused to the transmembrane domain of CD28 and signaling domains of CD28 and TCRζ. This construct includes an N-terminal Myc tag. DNA sequence of CD8α was codon-optimized for synthesis as a gBlock fragment. Signal peptide: nucleotides 1-63; Myc tag: nucleotides 64-93; CD19 scFv: nucleotides 94-819; CD8α hinge: nucleotides 820-954; CD28 transmembrane domain: nucleotides 955-1035; CD28 signaling domain: nucleotides 1036-1158; TCRζ: nucleotides 1159-1497.

atggcgctccctgtcaccgcactgcttcttccgctggcactgctgctgc acgctgcacggcctgagcaaaaacttatctctgaagaggacctcgatat acagatgacgcagacaacgtcaagtctttccgccagcttgggagaccga gtgactatatcttgtagagcaagccaggatatttctaagtatcttaact ggtaccaacaaaagcccgatggaacggttaagctgcttatataccatac cagtagactccactccggcgtaccatcacggttttctggcagtggctcc gggaccgactattctttgacgatctctaatctcgaacaagaggatattg caacatacttttgtcagcaaggcaataccttgccatatacgtttggggg gggacaaaacttgagataaccggcggcggtggttcaggcggtggcggtt ccggtggtggggggatcagaggttaagcttcaggaatccggaccaggttt ggttgccccagccaatctctcagcgttacatgcacggtttcaggcgtc agtctccccgattacggtgtaagttggattcggcaacctccgcgaaagg gtctggaatggctgggggttatttggggggagtgagacaacttattacaa ctctgcacttaagagtcggcttaccatcatcaaggataattcaaaatca caagtattcctgaagatgaactcattgcaaacagatgatacagctatat actattgtgccaagcattactattatggtggtcttatgcaatggatta ctgggggcaaggcacgtcagtgacagtgagttcaACCACCACCCCTGCA

CCAAGACCTCCAACTCCTGCCCCAACTATTGCAAGTCAGCCACTTTCTT

TGCGACCAGAGGCGTGCCGGCCAGCGGCGGGGGGCGCAGTGCACACGAG

GGGGCTGGACTTCGCCTGTGATTTTTGGGTGCTGGTGGTGGTTGGTGGA

GTCCTGGCTTGCTATAGCTTGCTAGTAACAGTGGCCTTTATTATTTTCT

GGGGTGAGGAGTAAGAGGAGCAGGCTCCTGCACAGTGACTACATGAACAT

GACTCCCCGCCGCCCCGGGCCCACCCGCAAGCATTACCAGCCCTATGCC

CCACCACGCGACTTCGCAGCCTATCGCTCCagagtgaagttcagcagga gcgcagacgcccccgcgtaccagcagggccagaaccagctctataacga gctcaatctaggacgaagagaggagtacgatgtttttggacaagagacgt ggccgggaccctgagatggggggaaagccgcagagaaggaagaaccctc aggaaggcctgtacaatgaactgcagaaagataagatggcggaggccta cagtgagattgggatgaaaggcgagcgccggaggggcaaggggcacgat ggcctttaccagggtctcagtacagccaccaaggacacctacgacgccc ttcacatgcaggccctgccccctcgc SEQ ID NO: 18 is the amino acid sequence of CD19 scFv, followed by a CD8α hinge domain fused to the transmembrane domain of CD28 and signaling domains of CD28 and TCRζ. This construct includes an N-terminal Myc tag. Signal peptide: amino acids 1-21; Myc tag: amino acids 22-31; CD19 scFv: amino acids 32-273; CD8α hinge: amino acids 274-318; CD28 transmembrane domain: amino acids 319-345; CD28 signaling domain: amino acids 346-386; TCRζ: amino acids 387-499.

MALPVTALLLPLALLLHAARPEQKLISEEDLDIQMTQTTSSLSASLGDR

VTISCRASQDISKYLNWYQQKPDGTVKLLIYHTSRLHSGVPSRFSGSGS

GTDYSLIISNLEQEDIATYFCQQGNTLPYTFGGGTKLEITGGGGSGGGG

SGGGGSEVKLQESGPGLVAPSQSLSVTCTVSGVSLPDYGVSWIRQPPRK

GLEWLGVIWGSETTYYNSALKSRLTIIKDNSKSQVFLKMNSLQTDDTAI

YYCAKHYYYGGSYAMDYWGQGTSVTVSSTTTPAPRPPTPAPTIASQPLS

LRPEACRPAAGGAVHTRGLDFACDFWVLVVVGGVLACYSLLVTVAFIIF

WVRSKRSRLLHSDYMNMTPRRPGPTRKHYQPYAPPRDFAAYRSRVKFSR

SADAPAYQQGQNQLYNELNLGRREEYDVLDKRRGRDPEMGGKPQRRKNP

QEGLYNELQKDKMAEAYSEIGMKGERRRGKGHDGLYQGLSTATKDTYDA

LHMQALPPR

SEQ ID NO: 19 is the nucleic acid sequence of CD19 scFv, followed by a CD8α hinge domain fused to the transmembrane domain of CD28H and signaling domain of TCRζ. This construct includes an N-terminal Myc tag. DNA sequence of CD8α was codon-optimized for synthesis as a gBlock fragment. Signal peptide: nucleotides 1-63; Myc tag: nucleotides 64-93; CD19 scFv: nucleotides 94-819; CD8α hinge: nucleotides 820-954; CD28H transmembrane domain: nucleotides 955-1017; TCRζ: nucleotides 1018-1356.

atggcgctccctgtcaccgcactgcttcttccgctggcactgctgctgc acgctgcacggcctgagcaaaaacttatctctgaagaggacctcgatat acagatgacgcagacaacgtcaagtctttccgccagcttgggagaccga gtgactatatcttgtagagcaagccaggatatttctaagtatcttaact ggtaccaacaaaagcccgatggaacggttaagctgcttatataccatac -continued

```
cagtagactccactccggcgtaccatcacggttttctggcagtggctcc gggaccgactattctttgacgatctctaatctcgaacaagaggatattg caacatacttttgtcagcaaggcaataccttgccatatacgtttgggggg gggacaaaacttgagataaccggcggcggtggttcaggcggtggcggtt ccggtggtgggggatcagaggttaagcttcaggaatccggaccaggttt ggttgccccagccaatctctcagcgttacatgcacggtttcaggcgtc agtctccccgattacggtgtaagttggattcggcaacctccgcgaaagg gtctggaatggctgggggttatttgggggagtgagacaacttattacaa ctctgcacttaagagtcggcttaccatcatcaaggataattcaaaatca caagtattcctgaagatgaactcattgcaaacagatgatacagctatat actattgtgccaagcattactattatggtggttcttatgcaatggatta ctgggggcaaggcacgtcagtgacagtgagttcaACCACCACCCCTGCA

CCAAGACCTCCAACTCCTGCCCCAACTATTGCAAGTCAGCCACTTTCTT

TGCGACCAGAGGCGTGCCGGCCAGCGGCGGGGGGCGCAGTGCACACGAG

GGGGCTGGACTTCGCCTGTGATTTCCTCTTCGTGCTGCTGGGGGTGGGA

AGCATGGGTGTGGCTGCGATCGTGTGGGGTGCCTGGagagtgaagttca gcaggagcgcagacgccccgcgtaccagcagggccagaaccagctcta taacgagctcaatctaggacgaagagaggagtacgatgtttttggacaag agacgtggccgggaccctgagatggggggaaagccgcagagaaggaaga accctcaggaaggcctgtacaatgaactgcagaaagataagatggcgga ggcctacagtgagattgggatgaaaggcgagcgccggaggggcaagggg cacgatggcctttaccagggtctcagtacagccaccaaggacacctacg acgcccttcacatgcaggccctgcccctcgc
```

SEQ ID NO: 20 is the amino acid sequence of CD19 scFv, followed by a CD8α hinge domain fused to the transmembrane domain of CD28H and signaling domain of TCRζ. This construct includes an N-terminal Myc tag. Signal peptide: amino acids 1-21; Myc tag: amino acids 22-31; CD19 scFv: amino acids 32-273; CD8α hinge: amino acids 274-318; CD28H transmembrane domain: amino acids 319-339; TCRζ: amino acids 340-452.

```
MALPVTALLLPLALLLHAARPEQKLISEEDLDIQMTQTTSSLSASLGDR

VTISCRASQDISKYLNWYQQKPDGTVKLLIYHTSRLHSGVPSRFSGSGS

GTDYSLIISNLEQEDIATYFCQQGNTLPYTFGGGTKLEITGGGGSGGGG

SGGGGSEVKLQESGPGLVAPSQSLSVTCTVSGVSLPDYGVSWIRQPPRK

GLEWLGVIWGSETTYYNSALKSRLTIIKDNSKSQVFLKMNSLQTDDTAI

YYCAKHYYYGGSYAMDYWGQGTSVTVSSTTTPAPRPPTPAPTIASQPLS

LRPEACRPAAGGAVHTRGLDFACDELFVLLGVGSMGVAAIVWGAWRVKF

SRSADAPAYQQGQNQLYNELNLGRREEYDVLDKRRGRDPEMGGKPQRRK

NPQEGLYNELQKDKMAEAYSEIGMKGERRRGKGHDGLYQGLSTATKDTY

DALHMQALPPR
```

SEQ ID NO: 21 is an exemplary amino acid sequence of CD16 (FCGR3A)

```
MWQLLLLPTALLLLLVSAGMRTEDLPKAVVFLEPQWYRVLEKDSVTLKCQG

AYSPEDNSTQWFHNESLISSQASSYFIDAATVDDSGEYRCQTNLSTLSD

PVQLEVHIGWLLLQAPRWVFKEEDPIHLRCHSWKNTALHKVTYLQNGKG

RKYFHHNSDFYIPKATLKDSGSYFCRGLFGSKNVSSETVNITITQGLAV

STISSFFPPGYQVSFCLVMVLLFAVDIGLYFSVKTNIRSSTRDWKDHKF

KWRKDPQDK
```

SEQ ID NO: 22 is an exemplary amino acid sequence of NKp46

```
MSSTLPALLCVGLCLSQRISAQQQTLPKPFIWAEPHFMVPKEKQVTICC

QGNYGAVEYQLHFEGSLFAVDRPKPPERINKVKFYIPDMNSRMAGQYSC

IYRVGELWSEPSNLLDLVVTEMYDTPTLSVHPGPEVISGEKVTFYCRLD

TATSMELLLKEGRSSHVQRGYGKVQAEFPLGPVTTAHRGTYRCFGSYNN

HAWSFPSEPVKLLVTGDIENTSLAPEDPTFPADTWGTYLLTTETGLQKD

HALWDHTAQNLLRMGLAFLVLVALVWFLVEDWLSRKRTRERASRASTWE

GRRRLNTQTL
```

SEQ ID NO: 23 is an exemplary amino acid sequence of NKp30

```
MAWMLLLILIMVHPGSCALWVSQPPEIRTLEGSSAFLPCSFNASQGRLA

IGSVTWERDEVVPGKEVRNGTPEFRGRLAPLASSRFLHDHQAELHIRDV

RGHDASIYVCRVEVLGLGVGTGNGTRLVVEKEHPQLGAGTVLLLRAGFY

AVSFLSVAVGSTVYYQGKCLTWKGPRRQLPAVVPAPLPPPCGSSAHLLP

PVPGG
```

SEQ ID NO: 24 is an exemplary amino acid sequence of NKp44

```
MAWRALHPLLLLLLLFPGSQAQSKAQVLQSVAGQTLTVRCQYPPTGSLY

EKKGWCKEASALVCIRLVTSSKPRIMAWTSRFTIWDDPDAGFFTVTMTD

LREEDSGHYWCRIYRPSDNSVSKSVRFYLVVSPASASTQTSWTPRDLVS

SQTQTQSCVPPTAGARQAPESPSTIPVPSQPQNSTLRPGPAAPIALVPV

FCGLLVAKSLVLSALLVWWGDIWWKIMMELRSLDTQKATCHLQQVTDLP

WTSVSSPVEREILYHTVARTKISDDDDEHTL
```

SEQ ID NO: 25 is an exemplary amino acid sequence of KIR2DS4

```
MSLMVIIMACVGFFLLQGAWPQEGVHRKPSFLALPGHLVKSEETVILQC

WSDVMFEHFLLHREGKENNTLHLIGEHHDGVSKANFSIGPMMPVLAGTY

RCYGSVPHSPYQLSAPSDPLDMVIIGLYEKPSLSAQPGPTVQAGENVTL

SCSSRSSYDMYHLSREGEAHERRLPAVRSINGTFQADFPLGPATHGGTY

RCFGSFRDAPYEWSNSSDPLLVSVTGNPSNSWPSPTEPSSKTGNPRHLH
```

-continued

VLIGTSVVKIPFTILLFELLHRWCSDKKNAAVMDQEPAGNRTVNSEDSD

EQDHQEVSYA

DETAILED DESCRIPTION

As demonstrated herein, CARs including an intracellular signaling domain from CD28H provide increased anti-tumor activity and ability to overcome inhibition. In particular examples, a combination of intracellular signaling domains from CD28H and 2B4 were used. As described in the Examples, compared to a third-generation T-cell CAR (CD28-41BB-TCRζ), a CAR including domains from co-activation receptors CD28H and 2B4 (CD244) (CD28H-2B4-TCRζ) induced stronger anti-tumor cytotoxicity by NK cells and was more potent in its ability to overcome inhibition by CD94-NKG2A and KIR2DL1. Similarly, a CAR including co-activation receptors CD28H and 2B4 (CD28H-2B4-TCRζ) induced stronger anti-tumor cytotoxicity by NK cells and was more potent in its ability to overcome inhibition by CD94-NKG2A and KIR2DL1 than another CAR composed of the transmembrane domain of NKG2D and the intracellular signaling domains from 2B4 and TCRζ (NKG2D-2B4-TCRζ).

I. Terms

Unless otherwise noted, technical terms are used according to conventional usage. Definitions of common terms in molecular biology may be found in *Lewin's Genes X*, ed. Krebs et al., Jones and Bartlett Publishers, 2009 (ISBN 0763766321); Kendrew et al. (eds.), *The Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 1995 (ISBN 0471186341); and George P. Rédei, *Encyclopedic Dictionary of Genetics, Genomics, Proteomics and Informatics*. $3^{rd}$ Edition, Springer, 2008 (ISBN: 1402067534), and other similar references.

Unless otherwise explained, all technical and scientific terms used herein have the same meaning as commonly understood by one of ordinary skill in the art to which this disclosure belongs. The singular terms "a," "an," and "the" include plural referents unless the context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description.

Although methods and materials similar or equivalent to those described herein can be used in the practice or testing of the present disclosure, suitable methods and materials are described below. All publications, patent applications, patents, and other references mentioned herein are incorporated by reference in their entirety, as are the GenBank Accession numbers (for the sequences present in GenBank on Mar. 26, 2020). In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

Antibody: A polypeptide ligand comprising at least one variable region that recognizes and binds (such as specifically recognizes and specifically binds) an epitope of an antigen. Mammalian immunoglobulin molecules are composed of a heavy (H) chain and a light (L) chain, each of which has a variable region, termed the variable heavy ($V_H$) region and the variable light ($V_L$) region, respectively. Together, the $V_H$ region and the $V_L$ region are responsible for binding the antigen recognized by the antibody. There are five main heavy chain classes (or isotypes) of mammalian immunoglobulin, which determine the functional activity of an antibody molecule: IgM, IgD, IgG, IgA and IgE.

Antibody variable regions contain "framework" regions and hypervariable regions, known as "complementarity determining regions" or "CDRs." The CDRs are primarily responsible for binding to an epitope of an antigen. The framework regions of an antibody serve to position and align the CDRs in three-dimensional space. The amino acid sequence boundaries of a given CDR can be readily determined using any of a number of well-known numbering schemes, including those described by Kabat et al. (*Sequences of Proteins of Immunological Interest*, U.S. Department of Health and Human Services, 1991; the "Kabat" numbering scheme), Chothia et al. (see Chothia and Lesk, *J Mol Biol* 196:901-917, 1987; Chothia et al., *Nature* 342:877, 1989; and Al-Lazikani et al., (JMB 273,927-948, 1997; the "Chothia" numbering scheme), and the ImMunoGeneTics (IMGT) database (see, Lefranc, *Nucleic Acids Res* 29:207-9, 2001; the "IMGT" numbering scheme). The Kabat and IMGT databases are maintained online.

A single-chain antibody (scFv) is a genetically engineered molecule containing the $V_H$ and $V_L$ domains of one or more antibody(ies) linked by a suitable polypeptide linker as a genetically fused single chain molecule (see, for example, Bird et al., *Science*, 242:423-426, 1988; Huston et al., *Proc. Natl. Acad. Sci.*, 85:5879-5883, 1988; Ahmad et al., *Clin. Dev. Immunol.*, 2012, doi:10.1155/2012/980250; Marbry, *IDrugs*, 13:543-549, 2010). The intramolecular orientation of the $V_H$-domain and the $V_L$-domain in a scFv, is typically not decisive for scFvs. Thus, scFvs with both possible arrangements ($V_H$-domain-linker domain-$V_L$-domain; $V_L$-domain-linker domain-$V_H$-domain) may be used. In a dsFv the $V_H$ and $V_L$ have been mutated to introduce a disulfide bond to stabilize the association of the chains. Diabodies also are included, which are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., *Proc. Natl. Acad. Sci.*, 90:6444-6448, 1993; Poljak et al., *Structure*, 2:1121-1123, 1994).

Antibodies also include genetically engineered forms such as chimeric antibodies (such as humanized murine antibodies) and heteroconjugate antibodies (such as bispecific antibodies). See also, *Pierce Catalog and Handbook*, 1994-1995 (Pierce Chemical Co., Rockford, IL); Kuby, J., *Immunology*, $3^{rd}$ Ed., W.H. Freeman & Co., New York, 1997.

2B4 (CD244): An NK cell surface receptor that mediates non-MHC restricted killing. 2B4 is also found on some T cells, dendritic cells, and monocytes. The ligand for 2B4 is CD48, which is expressed on hematopoietic cells. Two human isoforms have been identified. These have identical intracellular domains and differ by the presence or absence of five amino acids in the extracellular domain.

2B4 sequences are publicly available. Exemplary human 2B4 nucleic acid sequences include NM_016382 and NM_001166664. Exemplary human 2B4 amino acid sequences include GenBank Accession Nos. NP_057466 and NP_001160136. One of ordinary skill in the art can identify additional 2B4 nucleic acid and amino acid sequences, for example, utilizing currently available or subsequently developed sequence search and database tools.

CD28 homolog (CD28H): CD28H belongs to the CD28 family of immune receptors, which includes regulators of the immune system, such as checkpoint inhibitors PD-1 and CTLA-4. CD28H was initially described as a molecule involved in cell-cell interaction, cell migration, and angiogenesis of epithelial and endothelial cells. CD28H has a single extracellular immunoglobulin domain followed by a transmembrane domain and a 110 amino acid-long cytoplasmic region. CD28H is a costimulatory receptor in naïve T cells. The ligand of CD28H is B7 homolog 7 (B7H7, also known as B7-H5, encoded by the gene HHLA2), which co-stimulates T-cell growth and cytokine production. Besides expression on antigen presenting cells after stimulation, B7H7 is also broadly expressed in tumor tissues. CD28H⁺ naïve and memory T cells show diminished effector function and increased naïve features. CD28H expression has been described on NK cells, innate lymphoid cells (ILCs), and plasmacytoid dendritic cells (pDC) in human peripheral blood.

CD28H sequences are publicly available. Exemplary human CD28H nucleic acid sequences include NM_144615 and NM_001308232. Exemplary human CD28H amino acid sequences include GenBank Accession Nos. NP_653216 and NP_001295161. One of ordinary skill in the art can identify additional CD28H nucleic acid and amino acid sequences, for example, utilizing currently available or subsequently developed sequence search and database tools.

Chimeric antigen receptor (CAR): A chimeric molecule that includes an target-binding portion (such as a single domain antibody or scFv) and a signaling domain, such as a signaling domain from a T cell receptor (e.g. CD3ζ, also referred to herein as "TCRζ"). Typically, CARs include a target-binding portion, a transmembrane domain, and an intracellular domain. The intracellular domain typically includes a signaling domain having one or more immunoreceptor tyrosine-based activation motifs (ITAM), such as TCRζ (CD3ζ) or FcεR1γ. In some instances, the intracellular domain also includes the intracellular portion of at least one additional co-stimulatory domain or intracellular signaling molecule.

DAP12 (TYROBP): A transmembrane protein including an ITAM motif in the cytoplasmic domain, which may act as an activating signal transduction element and may bind ZAP70 and SYK.

DAP12 sequences are publicly available. Exemplary human DAP12 nucleic acid sequences include NM_198125 and NM_001173515. Exemplary human DAP12 amino acid sequences include GenBank Accession Nos. NP_937758 and NP_001166986. One of ordinary skill in the art can identify additional DAP12 nucleic acid and amino acid sequences, for example, utilizing currently available or subsequently developed sequence search and database tools.

Isolated: An "isolated" biological component, such as a nucleic acid, protein (including antibodies) or organelle, has been substantially separated or purified away from other biological components in the environment (such as a cell) in which the component naturally occurs, e.g., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Natural Killer (NK) cells: Cells of the immune system that kill target cells in the absence of a specific antigenic stimulus and without restriction according to MHC class. Target cells can be tumor cells or cells harboring viruses. NK cells are characterized by the presence of CD56 and the absence of CD3 surface markers. NK cells typically comprise approximately 10-15% of the mononuclear cell fraction in normal peripheral blood. Historically, NK cells were first identified by their ability to lyse certain tumor cells without prior immunization or activation. NK cells are thought to provide a "back up" protective mechanism against viruses and tumors that might escape the CTL response by down-regulating MHC class I presentation. In addition to being involved in direct cytotoxic killing, NK cells also serve a role in cytokine production, which can be important to control cancer and infection.

In some examples, a "modified NK cell" is a NK cell transduced or transformed with a heterologous nucleic acid (such as one or more of the nucleic acids or vectors disclosed herein) or expressing one or more heterologous proteins. The terms "modified NK cell" and "transduced NK cell" are used interchangeably in some examples herein.

Purified: The term purified does not require absolute purity; rather, it is intended as a relative term. Thus, for example, a purified protein or nucleic acid preparation is one in which the protein or nucleic acid is more enriched than the protein or nucleic acid is in its natural environment (e.g., within a cell). In one embodiment, a preparation is purified such that the protein or nucleic acid represents at least 50% of the total protein or nucleic acid content of the preparation. Substantial purification denotes purification from other proteins or cellular components. A substantially purified protein or nucleic acid is at least 60%, 70%, 80%, 90%, 95% or 98% pure. Thus, in one specific, non-limiting example, a substantially purified protein or nucleic acid is 90% free of other components.

Recombinant: A nucleic acid or protein that has a sequence that is not naturally occurring or has a sequence that is made by an artificial combination of two otherwise separated segments of sequence (e.g., a "chimeric" sequence). This artificial combination can be accomplished by chemical synthesis or by the artificial manipulation of isolated segments of nucleic acids, for example, by genetic engineering techniques.

Subject: A living multi-cellular vertebrate organism, a category that includes both human and veterinary subjects, including human and non-human mammals.

T cell: A white blood cell (lymphocyte) that is an important mediator of the immune response. T cells include, but are not limited to, CD4⁺ T cells and CD8⁺ T cells. A CD4⁺ T lymphocyte is an immune cell that carries a marker on its surface known as "cluster of differentiation 4" (CD4). These cells, also known as helper T cells, help orchestrate the immune response, including antibody responses as well as killer T cell responses. CD8⁺ T cells carry the "cluster of differentiation 8" (CD8) marker. In one embodiment, a CD8⁺ T cell is a cytotoxic T lymphocyte (CTL). In another embodiment, a CD8⁺ T cell is a suppressor T cell.

Activated T cells can be detected by an increase in cell proliferation and/or expression of or secretion of one or more cytokines (such as IL-2, IL-4, IL-6, IFNγ, or TNFα). Activation of CD8⁺ T cells can also be detected by an increase in cytolytic activity in response to an antigen.

In some examples, a "modified T cell" is a T cell transduced or transformed with a heterologous nucleic acid (such as one or more of the nucleic acids or vectors disclosed herein) or expressing one or more heterologous proteins. The terms "modified T cell" and "transduced T cell" are used interchangeably in some examples herein.

Transduced or Transformed: A transformed cell is a cell into which a nucleic acid molecule has been introduced by molecular biology techniques. As used herein, the terms transduction and transformation encompass all techniques by which a nucleic acid molecule might be introduced into such a cell, including transfection with viral vectors, the use of plasmid vectors, and introduction of DNA by electroporation, lipofection, and particle gun acceleration.

Treating or ameliorating a disease: "Treating" refers to a therapeutic intervention that decreases or inhibits a sign or symptom of a disease or pathological condition after it has begun to develop, such as a reduction in tumor size or tumor burden. "Ameliorating" refers to the reduction in the number or severity of signs or symptoms of a disease, such as cancer.

Vector: A nucleic acid molecule that can be introduced into a host cell (for example, by transfection or transduction), thereby producing a transformed host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant nucleic acid vectors having at least some nucleic acid sequences derived from one or more viruses. A replication deficient viral vector is a vector that requires complementation of one or more regions of the viral genome required for replication due to a deficiency in at least one replication-essential gene function.

II. Chimeric Antigen Receptors

Provided herein are CARs that include an intracellular signaling domain from CD28H and at least one additional intracellular signaling domain (such as 1 or 2 additional intracellular signaling domains). In some embodiments, the CAR includes (in N- to C-terminal order) a target binding domain (such as an antigen binding domain), optionally a hinge (or "stem") domain, a transmembrane domain, and an intracellular domain, including a first intracellular signaling domain from CD28H and a second intracellular signaling domain. The first and second intracellular signaling domains can be in any order. In particular embodiments, the intracellular domain includes a first intracellular signaling domain from CD28H and a second intracellular signaling domain from 2B4, TCRζ, FcεR1γ, or DAP12. Exemplary CARs include, but are not limited to, those schematically illustrated in FIG. 13B.

Also provided are CARs that include an intracellular signaling domain from CD28H and at least two additional intracellular signaling domains. In some embodiments, the CAR includes (in N- to C-terminal order) a target binding domain (such as an antigen binding domain), optionally a hinge (or "stem") domain, a transmembrane domain, and an intracellular domain including a first intracellular signaling domain from CD28H, a second intracellular signaling domain from 2B4, and a third intracellular signaling domain. The first, second, and third intracellular signaling domains can be in any order. In some examples, the third intracellular signaling domain is from TCRζ, FcεR1γ, or DAP12. Exemplary CARs include, but are not limited to, those schematically illustrated in FIG. 15A and those described in Table 2.

In some embodiments, the first intracellular signaling domain is from CD28H and includes an amino acid sequence at least 90%, at least 95%, at least 96%, at least 97%, at least 98%, or at least 99% identical to, or including or consisting of amino acids 172-282 of SEQ ID NO: 2. In additional examples, the CD28H intracellular signaling domain is encoded by a nucleic acid molecule with at least 90%, at least 95%, at least 96%, at least 97%, at least 98% or at least 99% identical to, or including or consisting of nucleotides 514-846 of SEQ ID NO: 1. In other examples, the nucleic acid encoding the CD28H intracellular signaling domain is codon-optimized and includes a nucleic acid molecule with at least 90%, at least 95%, at least 96%, at least 97%, at least 98% or at least 99% identical to, or including or consisting of nucleotides 1018-1350 of SEQ ID NO: 15.

In some embodiments, the intracellular domain includes a second intracellular signaling domains. The second intracellular signaling domain may be C-terminal to the first intracellular signaling domain, or may be N-terminal to the first intracellular signaling domain. In one example, the second intracellular signaling domain is from TCRζ. In some examples, the second intracellular signaling domain includes an amino acid sequence at least 90%, at least 95%, at least 96%, at least 97%, at least 98%, or at least 99% identical to, or including or consisting amino acids 283-395 of SEQ ID NO: 2. In additional examples, the TCRζ intracellular signaling domain is encoded by a nucleic acid molecule with at least 90%, at least 95%, at least 96%, at least 97%, at least 98% or at least 99% identical to, or including or consisting of nucleotides 847-1185 of SEQ ID NO: 1. In other embodiments, the second intracellular signaling is from 2B4 and includes an amino acid sequence at least 90%, at least 95%, at least 96%, at least 97%, at least 98%, or at least 99% identical to, or including or consisting of amino acids 171-291 of SEQ ID NO: 10. In additional examples, the 2B4 intracellular signaling domain is encoded by a nucleic acid molecule with at least 90%, at least 95%, at least 96%, at least 97%, at least 98% or at least 99% identical to, or including or consisting of nucleotides 514-873 of SEQ ID NO: 9. In still further embodiments, the second intracellular signaling domain is from FcεR1γ or DAP12.

In some embodiments, the intracellular domain includes a second intracellular domain from 2B4 (for example, as described above) and a third intracellular signaling domain. In particular embodiments, the third intracellular signaling domain is from TCRζ, FcεR1γ, or DAP12, for example, as described above.

In some embodiments, the target binding domain (also referred to as an antigen binding domain) is an antigen binding domain or scFv that binds to a target of interest, such as a protein expressed on a cancer or tumor cell or a tumor associated antigen. Any target binding domain can be inserted in the CARs described herein. In some embodiments, the target binding domain binds to a protein expressed on a hematological malignancy or a solid tumor. In some non-limiting examples, the antigen binding domain binds to CD19 (such as an scFv that binds to CD19). In other examples, the target binding domain binds to B7H7 (such as the extracellular domain of CD28H). Exemplary targets of the extracellular binding domain and corresponding malignancies are shown in Table 1.

TABLE 1

Exemplary extracellular antigen binding domain targets and malignancies

| Target | Malignancies |
|--------|--------------|
| CD19 | Acute lymphoblastic leukemia (ALL), lymphoma, Non-Hodgkin lymphoma |
| CD22 | ALL, lymphoma, Non-Hodgkin lymphoma |
| B cell maturation factor (BCMA) | Multiple myeloma |
| CD171 | Neuroblastoma |
| Epidermal growth factor receptor variant III (EGFRvIII) | Glioblastoma |
| Interleukin-13 receptor alpha (IL13Ra) | Glioblastoma |
| Mesothelin | Ovarian cancer, cervical cancer, breast cancer, Fallopian tube cancer, pancreatic cancer, lung cancer, colorectal cancer, peritoneal carcinoma |
| Mucin 16 (MUC-16) | Ovarian cancer |
| Mucin 1 (Muc1) | Sarcoma, breast cancer, cervical cancer, pancreatic cancer, lung cancer, liver cancer, glioma, colorectal cancer, gastric cancer |
| Receptor tyrosine kinase like orphan receptor 1 (ROR-1) | Breast cancer, ovarian cancer, lung adenocarcinoma, lymphoblastic leukemia |
| Prostate Stem Cell Antigen (PSCA) | Pancreatic cancer, lung cancer |
| CD33 | Myeloid leukemia |
| Prostate specific membrane antigen (PSMA) | Prostate cancer, bladder cancer, cervical cancer |
| CD123 | Acute myeloid leukemia (AML), leukemia |
| CD70 | B cell malignancies, breast cancer, ovarian cancer, pancreatic cancer, melanoma, renal cell cancer |
| Human epidermal growth factor receptor 2 (HER2) | Breast cancer, ovarian cancer, lung cancer, gastric cancer, colorectal cancer, pancreatic cancer, glioblastoma, glioma |
| Carcinoembryonic antigen (CEA) | Breast cancer, lung cancer, colorectal cancer, gastric cancer, pancreatic cancer, liver metastases |
| GTPase-activating protein (GAP) | Solid tumors |
| CD5 | T cell ALL, T cell non-Hodgkin lymphoma |
| CD38 | Multiple myeloma |
| Ephrin type-A receptor 2 (EphA2) | Glioma |
| Fibroblast activation protein alpha (FAP) | Mesothelioma |
| Ganglioside G2 (GD2) | Glioma, neuroblastoma, sarcoma, cervical cancer |
| Epithelial cell adhesion molecule (EpCam) | Breast cancer, prostate cancer, colon cancer, pancreatic cancer, gastric cancer, hepatic carcinoma, esophageal carcinoma, lymphoma, leukemia |
| CD133 | AML, breast cancer, ovarian cancer, colorectal cancer, glioma, pancreatic cancer, liver cancer |
| Glypican 3 (GPC3) | Lymphoma, leukemia, pancreatic cancer, colorectal cancer, lung cancer, liver cancer |
| B7H7 (HHLA2) | Breast cancer |

Thus, in some embodiments, the extracellular target binding domain binds to one or more of CD19, CD22, B cell maturation factor (BCMA), CD171, epidermal growth factor receptor variant III (EGFRvIII), interleukin-13 receptor alpha (IL-13Ra), mesothelin, mucin 16, mucin 1, receptor tyrosine kinase-like orphan receptor 1 (ROR-1), prostate stem cell antigen (PSCA), CD33, prostate-specific membrane antigen (PMSA), CD123, CD70, human epidermal growth factor receptor 2 (HER2), carcinoembryonic antigen (CEA), GTPase-activating protein (GAP), CD5, CD38, ephrin type-A receptor 2 (EphA2), fibroblast activation protein alpha (FAP), ganglioside G2 (GD2), epithelial cell adhesion molecule (EpCam), CD133, and glypican 3 (GPC3). This list is non-limiting, and additional extracellular targeting domains can also be utilized. In particular examples, the targeting domain is a scFv that binds to CD19 (such as amino acids 32-273 of SEQ ID NO: 12, or encoded by nucleotides 94-819 of SEQ ID NO: 11). In other particular examples, the extracellular target binding domain is a CD28H extracellular domain (such as amino acids 1-150 of SEQ ID NO: 8, or encoded by nucleotides 1-450 of SEQ ID NO: 7).

In some embodiments, the extracellular region of the CAR further includes a signal sequence domain, e.g., N-terminal to the antigen binding domain, for example, to facilitate expression of the CAR on the cell surface. In some examples, the signal sequence domain may be cleaved off of the CAR, during synthesis and/or upon expression on the cell surface. Therefore, in some embodiments, the CAR lacks a signal sequence domain. The signal sequence domain can include any suitable signal peptide sequence. In one non-limiting example, the signal sequence domain is a CD8α signal sequence. In some examples, the signal sequence includes or consists of amino acids 1-21 of SEQ ID NO: 16 or is encoded by nucleotides 1-63 of SEQ ID NO: 15. In another non-limiting example, the signal sequence domain is a human granulocyte-macrophage colony-stimulating factor (GM-CSF) signal sequence.

In other embodiments, the extracellular region of the CAR further includes a detectable label or tag, for example to facilitate detecting expression of the CAR in NK cells. In some examples, the detectable label or tag is N-terminal to the antigen binding domain; however, one of skill in the art could locate the detectable label or tag elsewhere in the construct, for example, C-terminal to the intracellular domains. In one non-limiting example, the detectable label or tag is a Myc tag. Other detectable labels or tags can be selected, including, but not limited to a fluorescent label.

In some embodiments, the disclosed CARs also include a hinge (or "stem") domain, which is in some examples a spacer between the extracellular targeting domain and the transmembrane region. However, in other embodiments, the CAR does not include a hinge domain. In some embodiments, the extracellular hinge domain is a CD8α hinge domain. In some examples, the hinge domain is a CD8α hinge domain at least 90%, at least 95%, at least 96%, at least 97%, at least 98% or at least 99% identical to, or including or consisting of the amino acid sequence of amino acids 274-318 of SEQ ID NO: 12. In additional examples, the CD8α hinge domain is encoded by a nucleic acid molecule with at least 90%, at least 95%, at least 96%, at least 97%, at least 98% or at least 99% identical to, or including or consisting of nucleotides 820-954 of SEQ ID NO: 11. In other examples, the hinge domain is included in the CD28H sequences utilized in the CARs disclosed herein (for example, the hinge domain between the Ig domain and the transmembrane domain of CD28H).

The disclosed CARs include a transmembrane domain that is linked to the hinge domain, if present (e.g., C-terminal to the hinge domain) and the intracellular domain (e.g., N-terminal to the intracellular domain). In other examples, the transmembrane domain is linked to the extracellular targeting domain (e.g., C-terminal to the extracellular targeting domain) and the intracellular domain (e.g., N-terminal to the intracellular domain), if a hinge domain is not present. In some embodiments, the transmembrane domain is a CD28H transmembrane domain. In other examples, the transmembrane domain is a CD28 transmembrane domain, an NKp30 transmembrane domain, an NKp46 transmembrane domain, a CD16 (FCGR3A) transmembrane domain, an NKp44 transmembrane domain, or a KIR2DS4 transmembrane domain. In one specific example, the transmembrane domain is from CD28H. In some examples, the transmembrane domain is a CD28H transmembrane domain with at least 90%, at least 95%, at least 96%, at least 97%, at least 98% or at least 99% identical to, or including or consisting of amino acids 319-339 of SEQ ID NO: 16. In additional examples, the CD28H transmembrane domain is encoded by a nucleic acid molecule (which in at least some examples, may be codon-optimized) with at least 90%, at least 95%, at least 96%, at least 97%, at least 98% or at least 99% identical to, or including or consisting of nucleotides 955-1017 of SEQ ID NO: 15. In other specific examples, the transmembrane domain is at least 90%, at least 95%, at least 96%, at least 97%, at least 98% or at least 99% identical to, or including or consisting of amino acids 136-156 of SEQ ID NO: 23 (NKp30), amino acids 256-279 of SEQ ID NO: 22 (NKp46), amino acids 209-229 of SEQ ID NO: 21 (CD16), amino acids 193-213 of SEQ ID NO: 24 NKp44), or amino acids 246-265 of SEQ ID NO: 25 (KIR2DS4).

In some embodiments, the CAR includes an intracellular region C-terminal of the transmembrane domain and N-terminal to the first intracellular signaling domain (for In particular embodiments, the CAR includes an amino acid sequence with at least 90% sequence identity (for example, at least 91%, at least 92%, at least 93%, at least 94%, at least 95%, at least 96%, at least 97%, at least 98% at least 99% identity) to any one of SEQ ID NOs: 2, 6, 12, 16, and 20. In some examples, the CAR includes or consists of the amino acid sequence of any one of SEQ ID NOs: 2, 6, 12, 16, and 20. In particular examples, the signal peptide and/or Myc tag included in any one of SEQ ID NOs: 2, 6, 12, 16, and 20 are removed prior to use.

Also provided are nucleic acids encoding the CARs disclosed herein. In some embodiments, the CAR is encoded by a nucleic acid sequence with at least 90% sequence identity (for example, at least 91%, at least 92%, at least 93%, at least 94%, at least 95%, at least 96%, at least 97%, at least 98% or at least 99% sequence identity) to any one of SEQ ID NOs: 1, 5, 11, 15, and 19 or includes or consists of the nucleic acid sequence of any one of SEQ ID NOs: 1, 5, 11, 15, and 19. In particular examples, the signal sequence and/or Myc tag encoding sequences included in any one of SEQ ID NOs: 1, 5, 11, 15, and 19 are removed prior to use.

TABLE 2

| Exemplary CARs | | | | | | | |
|---|---|---|---|---|---|---|---|
| | | Extracellular | | TM | Cytoplasmic | | |
| CD28H plus one other signaling domain | Myc-tag | Anti-CD19 scFv | CD8α hinge | CD28H | CD28H | TCRζ | |
| | Myc-tag | Anti-CD19 scFv | CD8α hinge | CD28H | CD28H | FceR1γ | |
| | Myc-tag | Anti-CD19 scFv | CD8α hinge | CD28H | CD28H | DAP12 | |
| | Myc-tag | Anti-CD19 scFv | CD8α hinge | CD28H | CD28H | 2B4 | |
| | Myc-tag | Anti-CD19 scFv | CD8α hinge | CD16[a] | CD28H | 2B4 | |
| | Myc-tag | Anti-CD19 scFv | CD8α hinge | NKp46[a] | CD28H | 2B4 | |
| | Myc-tag Extracellular | Anti-CD19 scFv | CD8α hinge | NKp30[a] TM | CD28H Cytoplasmic | 2B4 | |
| | Myc-tag | Anti-CD19 scFv | CD8α hinge | NKp44[a] | CD28H | 2B4 | |
| | Myc-tag | Anti-CD19 scFv | CD8α hinge | KIR2DS4[a] | CD28H | 2B4 | |
| CD28H plus two other signaling domains | Myc-tag | Anti-CD19 scFv | CD8α hinge | CD28H | CD28H | 2B4 | TCRζ |
| | Myc-tag | Anti-CD19 scFv | CD8α hinge | CD28H | CD28H | 2B4 | FceR1γ |
| | Myc-tag | Anti-CD19 scFv | CD8α hinge | CD28H | CD28H | 2B4 | DAP12 |

[a]These TM domains may optionally also include an intracellular region from the indicated protein, linked C-terminal to the TM domain example, an intracellular region of about 20-70 amino acids, such as about 25-50 amino acids, about 35-60 amino acids, or about 45-70 amino acids). In particular examples, this intracellular region is from NKp30, NKp46, CD16, NKp44, or KIR2DS4, and is linked C-terminal to their respective transmembrane domain (see e.g., Table 2 for examples). In particular examples, the intracellular region is at least 90%, at least 95%, at least 96%, at least 97%, at least 98% or at least 99% identical to, or includes or consists of amino acids 230-254 of SEQ ID NO: 21 (CD16), amino acids 280-304 of SEQ ID NO: 22 (NKp46), amino acids 157-201 of SEQ ID NO: 23 (NKp30), amino acids 214-276 of SEQ ID NO: 24 (NKp44), or amino acids 266-304 of SEQ ID NO: 25 (KIR2DS4).

Figure 15A:
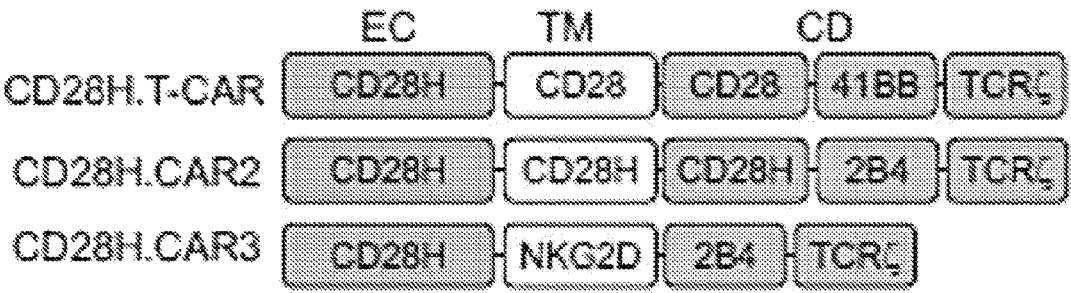
FIGS. 15A-15D show lysis of B7H7+ MHC-I+ tumor cells by NK cells expressing a CD28H-CAR, compared to NK cells expressing a 3rd generation T-CAR or an NKG2D-2B4-TCRζ CAR.

Exemplary CARs of this disclosure include, but are not limited to, those schematically illustrated in FIGS. 13B and 15A and those described in Table 2.

Also provided are functional variants of the CARs or the domains thereof described herein, which retain the biological activity of the CAR of which it is a variant or retains the biological activity of the particular domain. The functional variant can be at least about 80%, about 85%, about 90%, about 91%, about 92%, about 93%, about 94%, about 95%, about 96%), about 97%, about 98%, about 99% or more identical in amino acid sequence to the parent CAR or domain. Substitutions can be made, for example, in one or more of the extracellular targeting domain, hinge domain, transmembrane domain, and intracellular signaling domains.

In some examples, the functional variant includes the amino acid sequence of the parent CAR or domain with at least one conservative amino acid substitution (such as up to 10 conservative amino acid substitutions, for example, 1, 2, 3, 4, 5, 6, 7, 8, 9, or 10 conservative substitutions). In other examples, the functional variant includes the amino acid sequence of the parent CAR or domain with at least one non-conservative amino acid substitution (such as up to 10 non-conservative amino acid substitutions, for example, 1, 2, 3, 4, 5, 6, 7, 8, 9, or 10 non-conservative substitutions). In this case, the non-conservative amino acid substitution does not interfere with or inhibit the biological activity of the functional variant. The non-conservative amino acid substitution may enhance the biological activity of the functional variant, such that the biological activity of the functional variant is increased as compared to the parent CAR or domain.

The CARs or domains thereof can in some examples, include one or more synthetic amino acids in place of one or more naturally-occurring amino acids. Such synthetic amino acids include, for example, aminocyclohexane carboxylic acid, norleucine, a-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, oc-aminocycloheptane carboxylic acid, -(2-amino-2-norbornane)-carboxylic acid, γ-diaminobutyric acid, α,β-diaminopropionic acid, homophenylalanine, and α-tert-butylglycine. The CARs may be glycosylated, amidated, carboxylated, phosphorylated, esterified, N-acylated, cyclized via, e.g., a disulfide bridge, or converted into an acid addition salt and/or optionally dimerized or polymerized, or conjugated. In other embodiments, nucleic acids encoding the CARs may be codon-optimized, for example to improve expression in a cell of interest.

In some embodiments, a nucleic acid molecule encoding a disclosed CAR is included in an expression vector (such as a viral vector) for expression in a host cell, such as a T cell or NK cell. In some examples, the expression vector includes a promoter operably linked to the nucleic acid molecule encoding the CAR. Additional expression control sequences, such as one or more enhancers, transcription and/or translation terminators, and initiation sequences can also be included in the expression vector. In some embodiments, a nucleic acid encoding a CAR provided herein is included in a viral vector. Examples of suitable virus vectors include retrovirus (e.g., a gammaretrovirus, such as MoMLV or lentivirus), adenovirus, adeno-associated virus, vaccinia virus, and fowlpox vectors. In some examples, the CAR encoding nucleic acid is included in a MoMLV vector, such as an SFG retroviral vector or a pHAGE-CPPT lentiviral vector. In another example, the CAR-encoding nucleic acid is included in a pCDH-EF1α-MSC-T2A-Puro lentivirus expression vector. In other examples, the vector may be a DNA vector. In further example, the CAR-encoding nucleic acid is included in a γ-retrovirus vector, such as MSGV-1.

In some examples, the vector further includes a nucleic acid sequence encoding at least one additional CAR. In some examples, the additional CAR is specific to an additional tumor antigen, for example, to increase specificity of targeting of the disclosed CAR to tumor cells expressing or overexpressing a target antigen.

III. Cells Expressing Chimeric Adaptor Proteins

Also provided herein are cells (for example, immune cells) that express the disclosed CARs and compositions including cells expressing the disclosed CARs. In particular embodiments, the compositions include cells (such as NK cells or T cells) expressing a disclosed CAR and a pharmaceutically acceptable carrier.

In some embodiments, a nucleic acid molecule encoding a disclosed CAR is included in an expression vector (such as a viral vector) for expression in a host cell, such as a T cell or NK cell. In some examples, the expression vector includes a promoter operably linked to the nucleic acid molecule encoding the CAR. Additional expression control sequences, such as one or more enhancers, transcription and/or translation terminators, and initiation sequences can also be included in the expression vector.

The disclosed nucleic acids can be expressed in a host cell, such as a bacterial, plant, yeast, insect, or mammalian cell, for example, using an expression vector including a nucleic acid encoding the CAR. When the host is a eukaryote, methods of transfection of DNA such as calcium phosphate coprecipitation, microinjection, electroporation, insertion of a plasmid encased in liposomes, or virus vectors may be used. Eukaryotic cells can also be co-transformed with polynucleotide sequences encoding the CAR, and a second nucleic molecule encoding a selectable phenotype, such as the herpes simplex thymidine kinase gene. Another method is to use a eukaryotic viral vector, such as simian virus 40 (SV40), a lentivirus, or a retrovirus, to transduce or transform eukaryotic cells and express the CAR (see for example, *Viral Expression Vectors*, Springer Press, Muzyczka ed., 2011). In some examples, such expression systems are used to produce recombinant proteins in cells such as 293, COS, CHO, HeLa, or myeloma cell lines.

In some embodiments, a viral vector is utilized for expression of the CAR. Viral vectors include, but are not limited to simian virus 40, adenoviruses, adeno-associated virus (AAV), lentiviral vectors, and retroviruses, such as gamma retroviruses. Retroviral vectors provide a highly efficient method for gene transfer into eukaryotic cells. Moreover, retroviral integration takes place in a controlled fashion and results in the stable integration of one or a few copies of the new genetic information per cell. Without being bound by theory, lentiviral vectors have the advantage over vectors derived from onco-retroviruses such as murine leukemia viruses in that they can transduce non-proliferating cells, such as hepatocytes. They also have the added advantage of low immunogenicity. In one non-limiting example, the vector is a lentivirus vector such as pELNS, for example, with an EF1a promoter. Other exemplary vectors include pLV-ER1a-IRES-Neo, with neomycin deleted or retroviral vector MSGV. In a specific example, the vector is a pCDH-EF1α-MCS-T2A Puro lentivirus expression vector, which can be used to produce lentivirus along with plasmids sPAX2 and pMD2.G. for example.

Also provided are immune cells (such as NK cells or T cells) expressing a CAR disclosed herein. The immune cells are transduced with an expression vector including a nucleic acid encoding a CAR. In some examples, the transduced cells are peripheral blood lymphocytes (for example, obtained from a subject), peripheral blood mononuclear cells (for example, obtained from a subject), isolated T cells (such as a primary T cell or T cells obtained from a subject), or isolated NK cells (such as a primary NK cell or NK cells obtained from a subject). T cells or NK cells can be obtained from a sample from a subject, for example, blood, plasma, bone marrow, lymph node, or thymus. In some examples, T cells or NK cells are also enriched, purified, and/or expanded from a sample from a subject, for example before and/or after transduction with the CAR expression vector.

IV. Methods of Immunotherapy

Disclosed herein are methods of treating a subject with cancer (such as a hematological malignancy or a solid tumor) with a CAR. In some embodiments, the methods include administering to the subject a composition including a T cell or NK cell expressing a CAR disclosed herein (for example, transduced with a vector encoding the CAR) and a pharmaceutically acceptable carrier. In other examples, the methods include administering to the subject a pharmaceutical composition including an expression vector encoding a disclosed CAR and a pharmaceutically acceptable carrier. The extracellular targeting domain of the CAR is selected based on the cancer being treated, for example, as shown in Table 1.

Examples of hematological malignancies include leukemias, including acute leukemias (such as 11q23-positive acute leukemia, acute lymphocytic leukemia (ALL), T-cell ALL, acute myelocytic leukemia, acute myelogenous leukemia (AML), and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), lymphoblastic leukemia, polycythemia vera, lymphoma, diffuse large B cell lymphoma, Burkitt lymphoma, T cell lymphoma, follicular lymphoma, mantle cell lymphoma, Hodgkin disease, non-Hodgkin lymphoma, multiple myeloma, Waldenstrom macroglobulinemia, heavy chain disease, myelodysplastic syndrome, hairy cell leukemia, and myelodysplasia. In one non-limiting example, the hematological malignancy is acute lymphocytic leukemia (ALL).

Examples of solid tumors, include sarcomas (such as fibrosarcoma, myxosarcoma, liposarcoma, chondrosarcoma, osteogenic sarcoma, and other sarcomas), synovioma, mesothelioma, Ewing sarcoma, leiomyosarcoma, rhabdomyosarcoma, colon cancer, colorectal cancer, peritoneal cancer, esophageal cancer, pancreatic cancer, breast cancer (including basal breast carcinoma, ductal carcinoma and lobular breast carcinoma), lung cancer, ovarian cancer, prostate cancer, liver cancer (including hepatocellular carcinoma), gastric cancer, squamous cell carcinoma (including head and neck squamous cell carcinoma), basal cell carcinoma, adenocarcinoma, sweat gland carcinoma, medullary thyroid carcinoma, papillary thyroid carcinoma, pheochromocytoma, sebaceous gland carcinoma, papillary carcinoma, papillary adenocarcinoma, medullary carcinoma, bronchogenic carcinoma, hepatoma, bile duct carcinoma, choriocarcinoma, Wilms tumor, cervical cancer, fallopian tube cancer, testicular tumor, seminoma, bladder cancer (such as renal cell cancer), melanoma, and CNS tumors (such as a glioma, glioblastoma, astrocytoma, medulloblastoma, craniopharyrgioma, ependymoma, pinealoma, hemangioblastoma, acoustic neuroma, oligodendroglioma, meningioma, neuroblastoma and retinoblastoma). Solid tumors also include tumor metastases (for example, metastases to the lung, liver, brain, or bone).

A variety of pharmaceutically acceptable carriers can be used in the compositions provided herein, for example, buffered saline and the like, for introducing the cells or vectors to a subject. These solutions are sterile and generally free of undesirable matter. The compositions may be sterilized. In some examples, the compositions also include pharmaceutically acceptable auxiliary substances such as pH adjusting and buffering agents, toxicity adjusting agents, and preservatives, for example, sodium acetate, sodium chloride, potassium chloride, calcium chloride, sodium lactate and the like. The concentration in these formulations can vary, and will be selected primarily based on fluid volumes, viscosities, body weight and the like in accordance with the particular mode of administration selected and the subject's needs.

The precise amount of the composition to be administered can be determined by a physician with consideration of individual differences in age, weight, tumor size, extent of metastasis, and condition of the patient (subject). In some embodiments, a pharmaceutical composition comprising the T cells or NK cells expressing a CAR described herein is administered at a dosage of about $10^4$ to $10^9$ cells/kg body weight (for example, about $10^4$, $10^5$, $10^6$, $10^7$, $10^8$, or $10^9$ cells/kg), such as about $10^4$ to $10^6$ cells/kg, about $10^5$ to $10^7$ cells/kg, or about $10^6$ to $10^8$ cells/kg. Exemplary doses are about $10^5$ cells/kg to about $10^9$ cells/kg, such as about $10^6$ cells/kg, about $5\times10^6$ cells/kg, about $10^7$ cells/kg, about $5\times10^7$ cells/kg, about $10^8$ cells/kg, or about $5\times10^8$ cells/kg. The population of modified T cells or NK cells is typically administered parenterally, for example intravenously; however, injection or infusion to a tumor or close to a tumor (local administration) or administration to the peritoneal cavity can also be used. One of skill in the art can determine appropriate doses and routes of administration.

In some examples, the composition (such as a composition including the T cells or NK cells expressing the CAR) is administered one or more times, such as 1, 2, 3, 4, 5, 6, 7, 8, 9, or 10 times. The composition can be administered by intravenous injection or infusion. In some examples, the composition is administered daily, weekly, bimonthly or monthly. If multiple doses are administered, the time between administrations may be 1, 2, 3, 4, 5, 6, 7, 8, 9, 10, 11, 12, 13, 14 days, or more. In some non-limiting examples, the composition is formulated for intravenous administration and is administered multiple times. The quantity and frequency of administration will be determined by such factors as the condition of the subject and the type and severity of the subject's disease, although appropriate regimens may be determined by clinical trials.

In some examples, the CAR-modified NK cells or T cells are able to persist and/or replicate in vivo in the subject, resulting in long-term persistence that can lead to sustained tumor control. In same examples, the NK or T cells administered to the subject, or the progeny of these cells, persist in the subject for at least two months, three months, four months, five months, six months, seven months, eight months, nine months, ten months, eleven months, twelve months, thirteen months, fourteen months, fifteen months, sixteen months, seventeen months, eighteen months, nineteen months, twenty months, twenty-one months, twenty-two months, twenty-three months, or for years after administration to the subject. In other embodiments, the cells or their progeny are present for less than six months, five months, four months, three months two months, or one month, e.g., three weeks, two weeks, one week, after administration of the cells to the subject.

In one embodiment, the CAR is introduced into cells, such NK cells or T cells, and the subject (such as a subject with cancer) receives an administration of the cells. In some embodiments, the methods include isolating NK or T cells from a subject, transforming the NK or T cells with an expression vector (such as a lentiviral vector or a retroviral vector) encoding the CAR, and administering the modified NK cells or T cells expressing the CAR to the subject for treatment. The NK cells or T cells can be autologous to a recipient or allogeneic (for example, the isolated and transformed NK cells or T cells are not from the subject being treated). In some examples, the subject may undergo an immunosuppressive regimen (e.g., lymphodepletion or partial lymphodepletion) prior to administering the modified NK cells or T cells. Immune system supportive therapies (such as IL-2 and/or G-CSF) may also be administered to the subject, for example to promote expansion of the modified cells in the subject and/or to support recovery of neutrophils.

In some embodiments, a population of cells including lymphocytes (such as PBMCs) can be obtained by any method, including, but not limited to apheresis. All or a portion of the population of cells can be utilized immediately or all or a portion of the cells can be cryopreserved for future use. When ready for use, all or a portion of the population of cells is thawed (if previously cryopreserved) and NK cells or T cells are activated, enriched, and/or expanded in culture. Methods of isolating, activating, and expanding NK cells or T cells are known in the art (e.g., WO 2018/006054 and WO 2018/022646, incorporated herein by reference in their entirety). The cells are transduced with a vector including a CAR. In particular examples, about $10^7$-$10^9$ cells are transduced (for example, about $1\times10^7$, $5\times10^7$, $1\times10^8$, $5\times10^8$, or $1\times10^9$ cells). Transduced T cells or NK cells can be expanded ex vivo and can be cryopreserved at appropriate dosage amounts (for example, about $10^6$ to $10^{12}$ cells) following expansion. The transduced NK cells or T cells are thawed (if previously frozen), prior to administration to the subject. The subject may undergo an immunosuppressive regimen (e.g., lymphodepletion) prior to administering the modified NK cells or T cells. The modified NK cells or T cells are administered to the subject, for example by injection or infusion.

Treatment efficacy is monitored by methods such as tumor size, number of lesions, tumor stage, response rate, or other criteria. In some examples, a decrease in size of a primary tumor or metastases (for example, as defined by standard RECIST or irRECIST criteria) indicates inhibition of cancer in the subject. In other examples, progression-free survival and/or overall survival (for example, for 1 month, 3 months, 6 months, 9 months, 12 months, 18 months 2 years, or more, such as 1-12 months, 6-18 months, 1-2 years, or more) indicates inhibition of cancer in the subject. In other examples, one or more of persistence of circulating CAR-expressing NK cells or T cells, changes in immune cell subsets, and activation status of immune cells, as well as other immunologic determinants are evaluated, with clinical outcomes evaluated at baseline (e.g., prior to or at the time of administration of the modified cells), at different time points during treatment, and/or at the time of disease progression.

In some examples, the subject is also treated with one or more of surgery, chemotherapy, radiation, immunosuppressive agents, chemotherapeutic agents, or any combination of two or more thereof. Exemplary agents include, but are not limited to alkylating agents, such as nitrogen mustards (for example, chlorambucil, chlormethine, cyclophosphamide, ifosfamide, and melphalan), nitrosoureas (for example, carmustine, fotemustine, lomustine, and streptozocin), platinum compounds (for example, carboplatin, cisplatin, oxaliplatin, and BBR3464), busulfan, dacarbazine, mechlorethamine, procarbazine, temozolomide, thiotepa, and uramustine; antimetabolites, such as folic acid (for example, methotrexate, pemetrexed, and raltitrexed), purine (for example, cladribine, clofarabine, fludarabine, mercaptopurine, and thioguanine), pyrimidine (for example, capecitabine, cytarabine, fluorouracil, and gemcitabine; plant alkaloids, such as podophyllum (for example, etoposide, and teniposide), taxane (for example, docetaxel and paclitaxel), vinca (for example, vinblastine, vincristine, vindesine, and vinorelbine); cytotoxic/antitumor antibiotics, such as anthracycline family members (for example, daunorubicin, doxorubicin, epirubicin, idarubicin, mitoxantrone, and valrubicin), bleomycin, hydroxyurea, and mitomycin; topoisomerase inhibitors, such as topotecan and irinotecan; monoclonal antibodies, such as alemtuzumab, bevacizumab, cetuximab, gemtuzumab, rituximab, panitumumab, atezolizumab, avelumab, ipilimumab, ofatumumab, nivolumab, pembrolizumab, rituximab, durvalumab, and trastuzumab; photosensitizers, such as aminolevulinic acid, methyl aminolevulinate, porfimer sodium, and verteporfin; proteasome inhibitors, such as bortezomib, carfilzomib, oprozomib, ixazomib, marizomib, and delanzomib; kinase inhibitors, such as gefitinib, imatinib, sunitinib, sorafenib, vemurafenib, trametinib, and ruxolitinib; growth factor receptor inhibitors, such as acitinib, erlotinib, cabozantinib, and crizotinib; mTOR inhibitors, such as everolimus, temsirolimus, and temisorotimus; and other agents, such as alitretinoin, altretamine, amsacrine, anagrelide, arsenic trioxide, asparaginase, bexarotene, celecoxib, denileukin diftitox, enzalutamide, flutamide, nilutamide, bicalutamide, topilutamide, apalutamide, estramustine, hydroxycarbamide, pentostatin, masoprocol, mitotane, pegaspargase, tamoxifen, clomifene, raloxifene, anastrozole, fulvestrant, and tretinoin. Additional agents include checkpoint inhibitors, such as antibodies (e.g., nivolumab, pembrolizumab, ipilimumab, durvalumab, and atezolizumab) or small molecule inhibitors (e.g., BMS-1001, BMS-1166, CCX4503). In some examples, a checkpoint inhibitor is not administered to the subject. One of ordinary skill in the art can select one or more available agents appropriate to the subject and condition being treated.

EXAMPLES

The following examples are provided to illustrate certain particular features and/or embodiments. These examples should not be construed to limit the disclosure to the particular features or embodiments described.

Example 1

CD28 Homolog is a Strong Activator of Natural Killer Cells for Lysis of B7H7+ Tumor Cells Data included in this example was published in Zhuang and Long, *Cancer Immunol. Res.* 7(6):939-951, published online on Apr. 24, 2019, which is incorporated by reference herein in its entirety.

Materials and Methods

Plasmids: A plasmid containing B7H7 cDNA was obtained from Harvard PlasmID Database (#HsCD00044662). B7H7 cDNA was amplified and cloned into the EcoRI and NotI cloning sites of pAc5.1/V5-His A vector (Thermo Fisher Scientific) for expression in *Drosophila* S2 cells, and the EcoRI and NotI cloning sites of pCDH-EF1-T2A-Puro vector (System Biosciences) for expression in human cell lines. The cDNA of CD28H was obtained from Harvard PlasmID Database (#HsCD00416184) in the vector pLX304. CD28H cDNA was amplified and cloned into the EcoRI and NotI cloning sites of pCDH-EF1-T2A-Puro lentivirus vector (System Biosciences) for transduction of human cell lines. CD28H mutants and chimeras were generated using the In-Fusion HD cloning kit (Clontech) and verified by sequencing. All of the cDNAs cloned into the PCDH vector were in frame with the 2A-peptide. Expressed proteins could be detected by anti-2A antibody in immunoblots. All plasmid constructions were carried out using the In-Fusion HD cloning kit (Clontech).

Cells: Human NK cells were isolated from peripheral blood of healthy U.S. donors by negative selection (STEM-CELL Technologies). NK cells were resuspended in Iscove's modified Dulbecco's medium (IMDM; Gibco) supplemented with 10% human serum (Valley Biomedical) and used within 4 days. IL2 and PHA activated NK cells were cultured as described previously (Liu et al., *Immunity* 36:600-611, 2012). Briefly, freshly isolated NK cells were cultured with irradiated autologous feeder cells in OptTi-mizer (Invitrogen) supplemented with 10% purified IL2 (Hemagen), 100 units/ml recombinant IL2 (Roche) and 5 μg/ml phytohemagglutinin (PHA, Sigma), and expanded in the same medium without PHA and feeder cells. CD28H expression was tested after 2 weeks of activation. To obtain NK cells activated by NKp46 and CD2 plus IL2, freshly isolated NK cells were cultured in plates coated with 5 μg/ml CD2 and NKp46 mAbs, in the presence of 100 units/ml recombinant IL2 (Roche). CD28H expression was tested at day 3, day 5, and day 7. NKL cells (obtained from M. J. Robertson, Indiana University Cancer Research Institute, Indianapolis, IN) and KHYG-1 cells were cultured in IMDM Medium (Gibco) supplemented with 10% heat-inactivated fetal calf serum (Gibco), 2 mM L-Glutamine (Gibco), and 100 units/ml recombinant IL-2 (Roche). 721.221 cells (referred to as 221 cells), P815 cells (obtained from American Type Culture Collection, Manassas, VA), Daudi cells (ATCC Manassas, VA) and HDLM-2 cells (Ju et al., *PNAS* 113:1624-1629, 2016) (obtained from T. Wald-mann, NCI, NIH) were cultured in RPMI 1640 medium (Gibco) containing 10% heat-inactivated fetal calf serum (Gibco) and 2 mM L-Glutamine (Gibco). 221 cells trans-fected with HLA-E (221.AEH), which included the HLA-A signal peptide to achieve proper HLA-E expression (Lee et al., *PNAS* 95:199-204, 1998), were a gift from D. Geraghty (Fred Hutchinson Cancer Research Center, Seattle). Lenti-X 293T cells (Clontech) were cultured in DMEM medium (Gibco) supplemented with 10% heat-inactivated fetal calf serum (Gibco) and 2 mM L-Glutamine (Gibco). Cells were *mycoplasma*-free, as tested by the NIH Office of Research Services. All cell lines used were maintained in culture for no longer than 2 months after thawing, and were authenti-cated by morphology, growth characteristics, expression of surface markers, and functional assays.

Transfection and lentivirus production: For S2 cells trans-fection, cells were transfected with plasmids for CD48 and B7H7 expression, both together or each one alone, together with a pAc5.1/V5-His A-puro plasmid for selection in 6 μg/ml puromycin at $\frac{1}{10}^{th}$ the amount of the expression plasmids. Resistant cells were cloned, and tested for CD48 and B7H7 expression. For production of lentivirus, low-passage Lenti-X 293T cells (Clontech) were plated in a T75 flask 1 day before transfection. Cells were transfected with PEI Max (Polyethylenimine). Briefly, plasmids pMD2.G 1.2 μg, psPAX2 2.3 μg, PCDH 4.6 μg and 217 μl serum-free DMEM were mixed in a 15 ml Falcon tube. 65 μl of PEI Max 40K (Polysciences) stock solution (1 mg/ml) were added, and samples were vortexed briefly. After 10 min at room temperature, 8.6 ml DMEM media with 10% FCS were added to the tube. Culture medium for the 293T cells was replaced with the fresh medium containing the trans-fection reagent mixture. Two days after transfection, super-natants were collected, passed through a 0.45 μm filter, aliquoted and stored at −80° C. Supernatants for transduc-tion were used either directly or after enrichment with PEG-it (System Biosciences) to increase virus titer. For transduction of human cell lines, lentivirus was added to cells together with polybrene to a final concentration of 8 μg/ml, and incubated for 2 days. Cells were centrifuged at 1200 rpm for 10 min, and resuspended in complete medium with pre-titrated concentrations of puromycin. Surface expression of transduced genes on puromycin-resistant cells was verified by flow cytometry.

Flow cytometry assays: Most flow cytometry assays were performed by incubating cells with premixed fluorophore-conjugated antibodies at 4° C. for 30 minutes. Staining for HLA-E was performed by first incubating cells with anti-HLA-E (3D12) or control mouse IgG1 (clone MOPC-21), followed by PE-conjugated polyclonal goat F (ab') 2 anti-mouse IgG Fc (Jackson). NK cells expanded in IL2 were pre-incubated in 10% human serum for 30 minutes on ice to block Fc receptor CD16, prior to staining with antibodies. As resting NK cells were cultured in IMDM containing 10% human serum until use, no further Fc receptor blocking was needed. Cells were washed after staining, and analyzed on a LSR II (BD Biosciences) or LSRFortessa™ X-20 (BD Biosciences). Data were analyzed with FlowJo (FlowJo, LLC).

Degranulation and cytotoxicity assays: Redirected cyto-toxicity assays were performed as described (Bryceson et al., *Blood* 107:159-166, 2006). Briefly, P815 cells were incubated with 5 μg/ml of the indicated combinations of mAbs to CD28H (R&D MAB83162), 2B4 (BioLegend 329502), NKp46 (BD 557847), NKG2D (R&D MAB139), CD2 (BD 555323), DNAM-1 (BD Biosciences 559787), CD16 (BD 555404) and CD56 (BD 555513) for 15 minutes at room temperature. Resting NK cells were added at an E:T ratio of 1:2, mixed and gently centrifuged at 300 rpm for 1 minute. After 2 hours at 37° C., cells were stained with Live/Dead-NIR (Thermo Fisher), anti-CD56-Bv421 (BD 562751) and anti-CD107a-PE (BD 555801) and analyzed by flow cytometry. Target cell lysis assays were either per-formed using the ToxiLight Non-Destructive Cytotoxicity BioAssay Kit (Lonza) following the manufacturer's instruc-tions, or through a flow-based assay. Briefly, NK cells were incubated with PKH67-labeled target cells for 6 hours in IMDM medium with 10% FCS at the indicated E:T ratios. Cells were stained with Live/Dead NIR, and the lysis of target cells were determined by flow cytometry. For CD28H blocking, NK cells were pre-incubated with 10 μg/ml CD28H antibody (R&D Systems) for 15 min before mixing with 221.B7H7 cells. KHYG-1 and NKL cells were rested in complete IMDM medium without IL-2 for 1 day, prior to use in cytotoxicity assays.

S2 cell mixing and multiple functional assays: Resting NK cells were mixed with transfected S2 cells at an ET ratio of 1:2. Cells were incubated in IMDM medium with 10% FCS for 2 hours, stained with Live/Dead-NIR, anti-CD56-Bv421 and anti-CD107a-PE, and analyzed by flow cytom-etry. To stain for intracellular cytokines and chemokines, NK cells and S2 cells were incubated for 1 hour, and in the presence of 3 μM GolgiStop (BD Biosciences) for 5 hours. For CD28H blocking, 10 μg/ml CD28H antibody (R&D Systems) was pre-incubated with NK cells for 15 min before mixing with S2 cells. Cells were stained with anti-CD107a-PE (BD 555801) and anti-CD56-Bv421 (BD 562751), fixed with 4% paraformaldehyde for 10 min, and permeabilized with the Intracellular Staining Permeabilization Wash Buffer (BioLegend). Cells were stained with anti-IFN-γ-APC (Bi-oLegend 506510), anti-TNF-α-BV650 (BioLegend 502937), anti-MIP-1α-FITC (Invitrogen MA523564) and anti-MIP-1β-PerCP-Cy5.5 (BD 560688). Data were obtained on a LSR II (BD Biosciences) or LSRFortessa™ X-20 (BD Biosciences), and analyzed with FlowJo (FlowJo, LLC).

ADCC assays: S2 cells were pre-incubated with a rabbit anti-S2 serum diluted 1:10,000 for 15 min at room temperature. Resting NK cells were added at an E:T ratio of 1:2, mixed, and centrifuged at 300 rpm for 1 min. After 2 hours at 37° C. in IMDM medium with 10% FCS, cells were stained with Live/Dead-NIR, anti-CD56-Bv421, and anti-CD107a-PE, and analyzed by flow cytometry. For ADCC assays using Rituximab, 221 cells and Daudi cells were pre-incubated with 10 μg/ml Rituximab at room temperature for 15 min. Resting NK cells were added at an E:T ratio of 5:1, and incubated for 5 hours. Lysis of target cells was determined using the ToxiLight Non-Destructive Cytotoxicity BioAssay Kit (Lonza) following the manufacturer's instructions.

Statistical analysis: Statistical analysis was performed with GraphPad PRISM V7. Data are presented as mean±SEM, and compared by two-tailed Mann-Whitney test or Wilcoxon signed-rank test.

Human donors: Peripheral blood samples from healthy U.S. adults were obtained from the NIH Department of Transfusion Medicine in accordance with the Belmont Report, under an NIH Institutional Review Board-approved protocol (99-CC-0168) with informed written consent.

Results

Figures 1A, 1B, 1C:
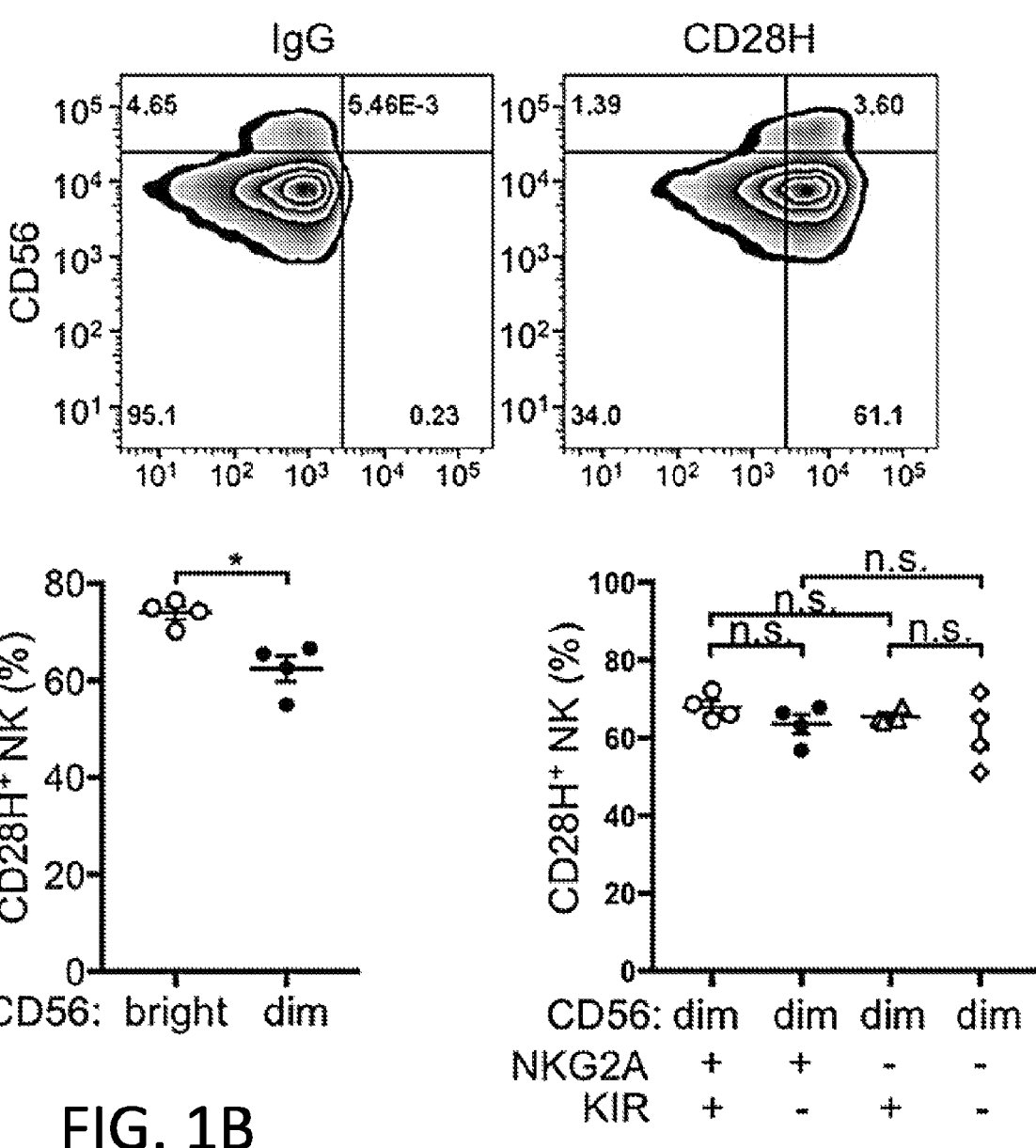
Figure 2A:
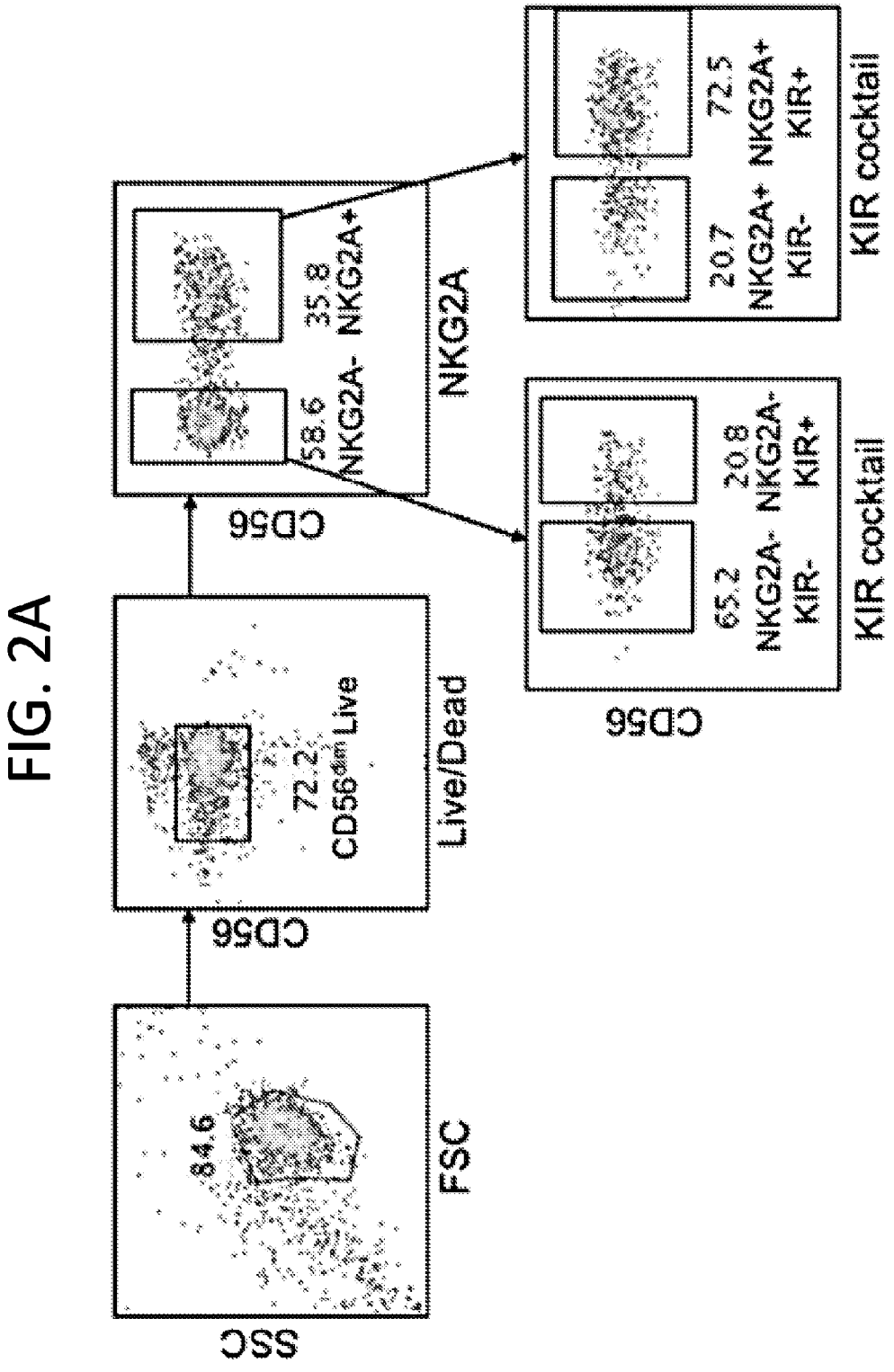
Figures 2E, 2F:
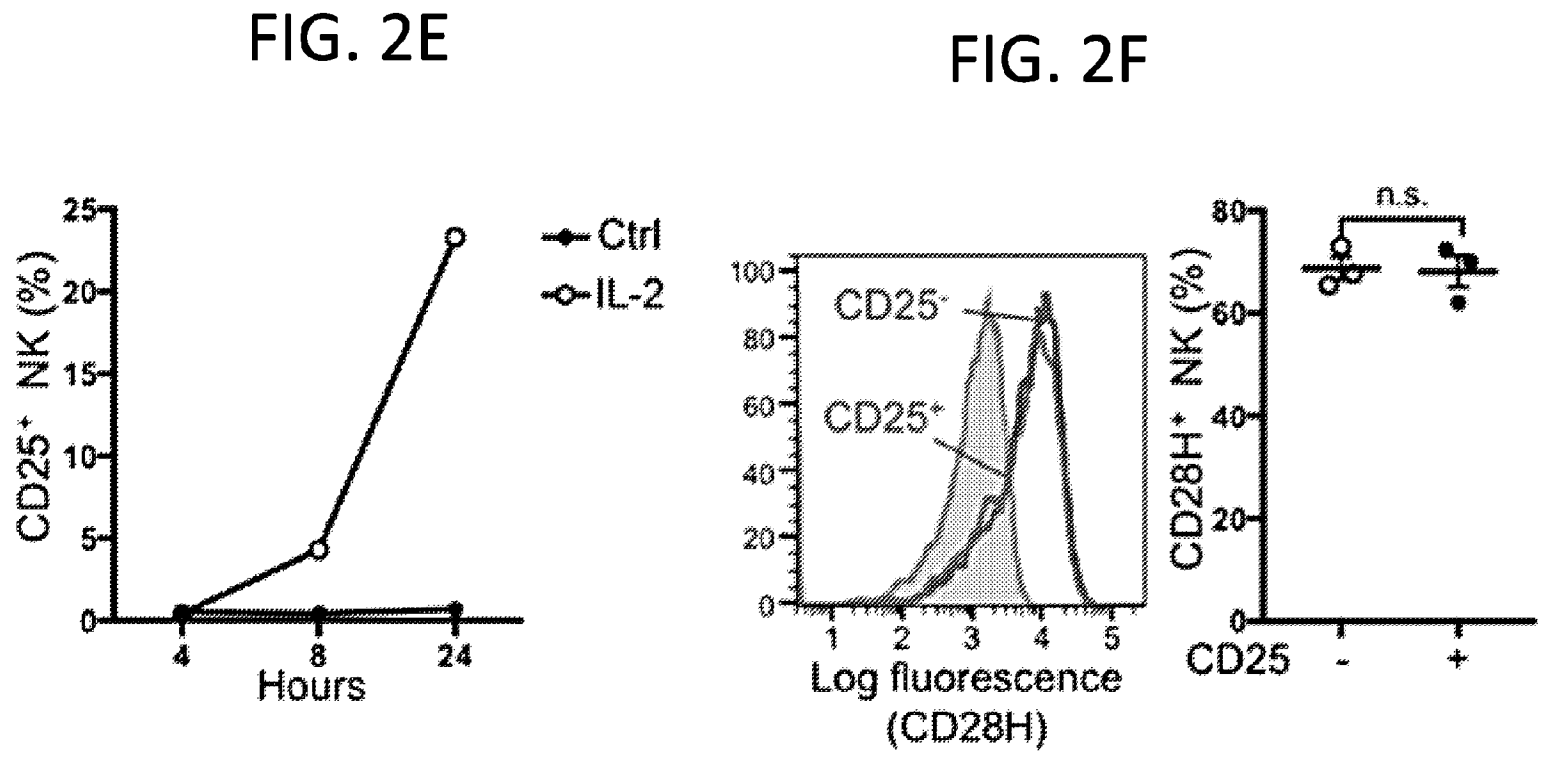

CD28H is expressed on primary, resting human NK cells: The majority of freshly isolated, human NK cells expressed CD28H at the cell surface (FIG. 1A). Human NK cells can be divided into CD56$^{bright}$ and CD56$^{dim}$ NK subsets based on the expression of CD56. The two subsets have distinct phenotypes and properties (Cooper et al., *Trends Immunol.* 22:633-640, 2001). We examined CD28H expression in the two NK subsets, and a greater fraction of the CD56$^{bright}$ subset expressed CD28H (FIG. 1B). Most of the CD56$^{bright}$ NK cells are phenotyped as CD56$^{bright}$CD16 KIR NKG2A$^+$ CD57$^-$, and represent a less mature NK cell population (Cooper et al., *Trends Immunol.* 22:633-640, 2001). Expression of KIR and NKG2A can divide CD56$^{dim}$ NK cells into several subsets (FIG. 2A). However, no significant difference in CD28H expression was found between CD56$^{dim}$ NK cells that were NKG2A$^+$KIR$^+$, NKG2A$^+$KIR$^-$, NKG2A$^-$ KIR$^+$, and NKG2A$^-$KIR$^-$ NK (FIG. 1C). CD57 expression can also be used to further separate CD56$^{dim}$ NK cells (Lopez-Verges et al., *Blood* 116:3865-3874, 2010). CD57$^+$ NK cells are mature, terminal differentiated, and have decreased capacity for proliferation (Lopez-Verges et al., *Blood* 116:3865-3874, 2010). A lower proportion of CD57$^+$ cells expressed CD28H, as compared to the CD56$^{dim}$CD57$^-$ NK subset (FIG. 1D). Ex vivo expanded and activated NK cells are highly cytotoxic and have been used in clinical and basic research for decades (Bachanova et al., *Crit Rev Oncog.* 19:133-141, 2014; Granzin et al., *Front Immunol.* 8:458, 2017). A well-established strategy for NK cell expansion in culture is the combination of IL2 and PHA in the presence of irradiated autologous PBMC as feeder cells (Liu et al., *Immunity* 36:600-611, 20012; Granzin et al., *Front Immunol.* 8:458, 2017). CD28H expression on NK cells was lost after 2 weeks in IL2 and PHA (FIG. 2B), a result consistent with a quantitative proteomics analysis of immune cells, in which NK cells had been stimulated with IL2 and plate-coated mAbs to CD2 and NKp46 (Rieckmann et al., *Nat Immunol.* 18:583-593, 2017). Using the same stimulating conditions, we confirmed the decrease of CD28H expression by immunostaining (FIG. 2C). A reduction in the proportion of NK cells that expressed CD28H was observed 3 days after activation, and gradually dropped to ~20% of NK cells after 7 days of activation (FIG. 2D). We also tested expression of CD28H on NK cells activated for a shorter time in IL2. CD25 expression was used as a marker for activation (FIG. 2E). No significant difference was observed in CD28H expression on CD25$^+$ and CD25$^-$ NK cells after activation in IL2 for 24 hours (FIG. 2F). The results showed that expression of CD28H decreased only after long-term stimulation and expansion, but not by short-term activation with IL2.

Figure 3A:
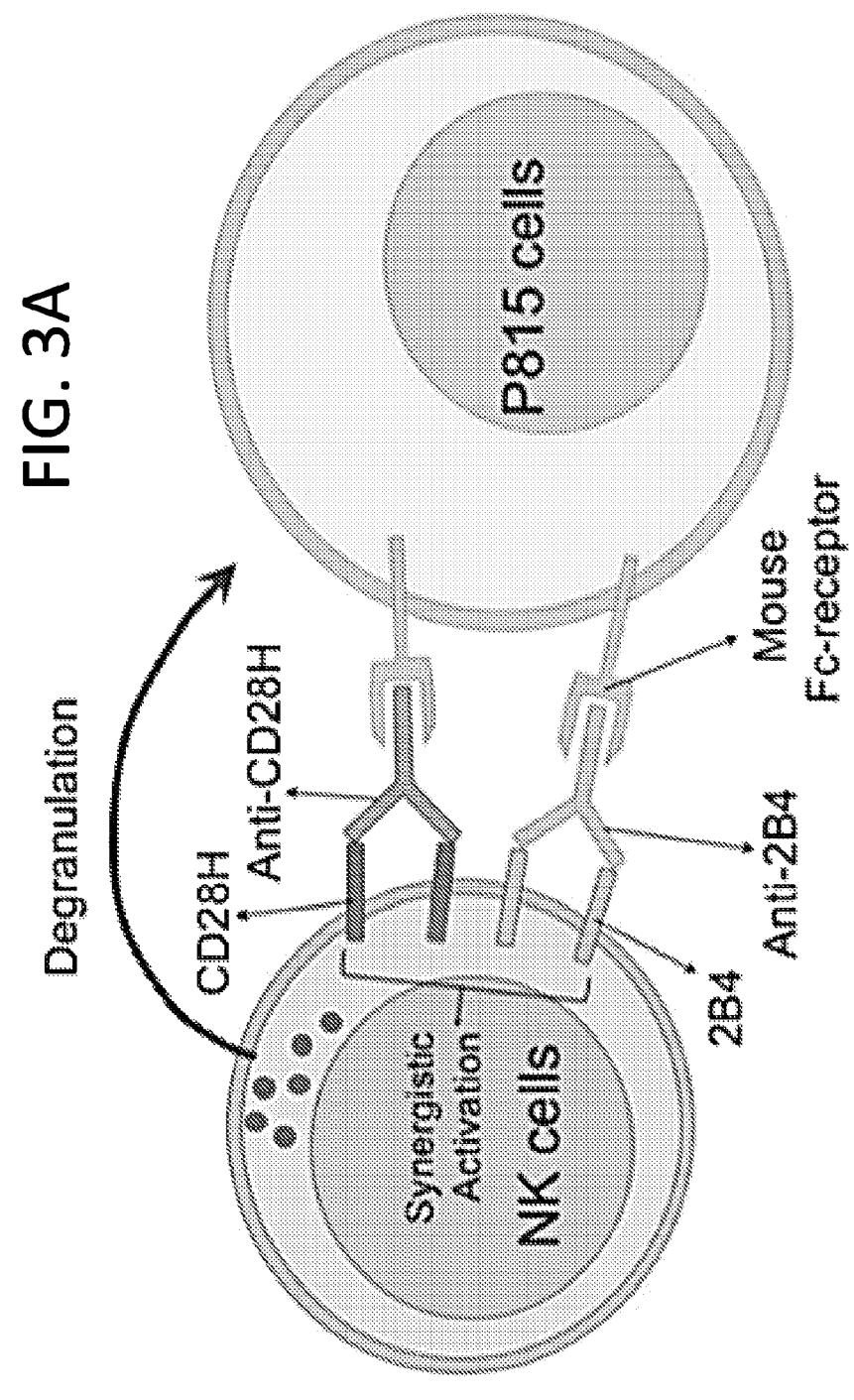
FIGS. 3A-3C.
Figure 4A:
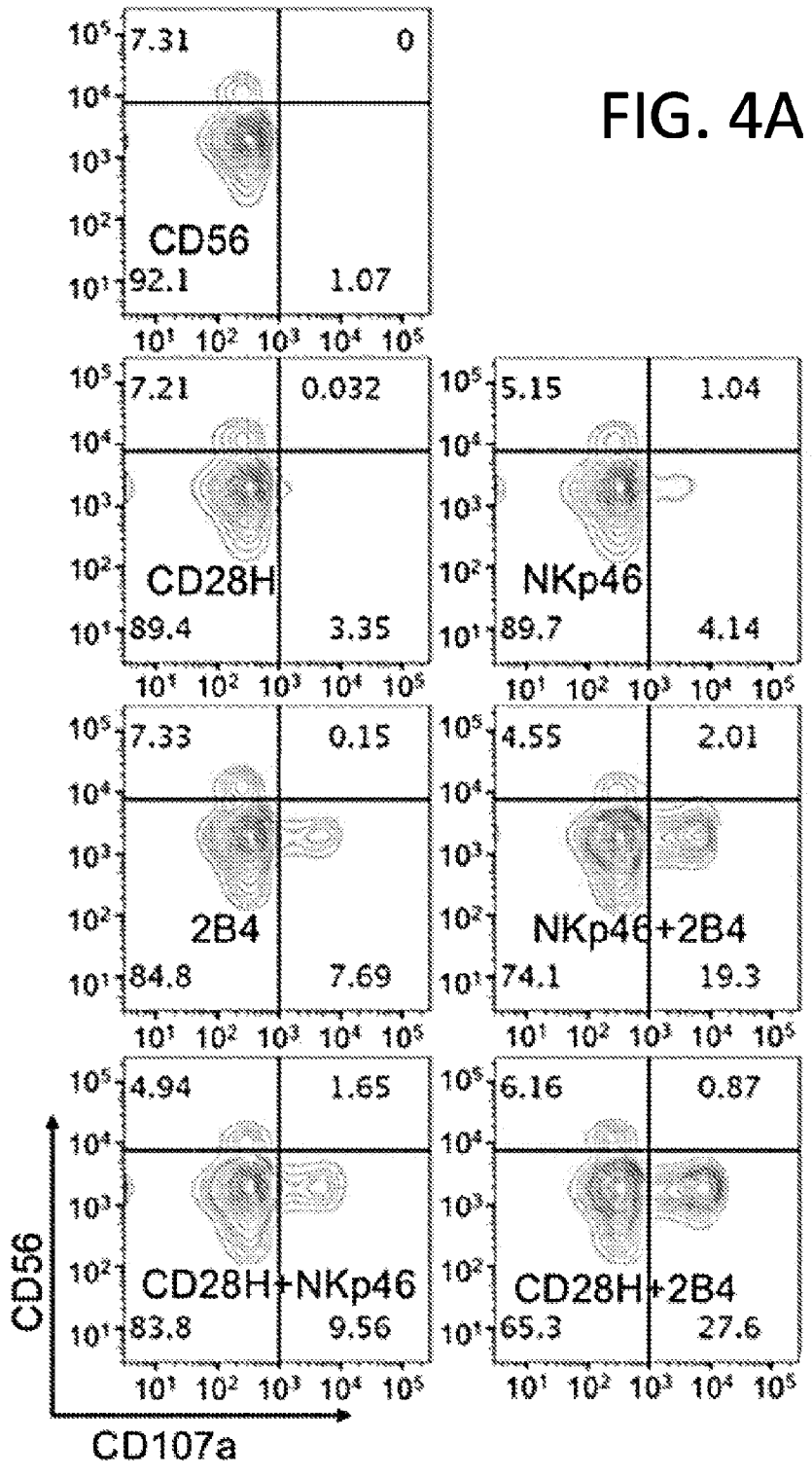
Figures 4B, 4C, 4D, 4E, 4F:
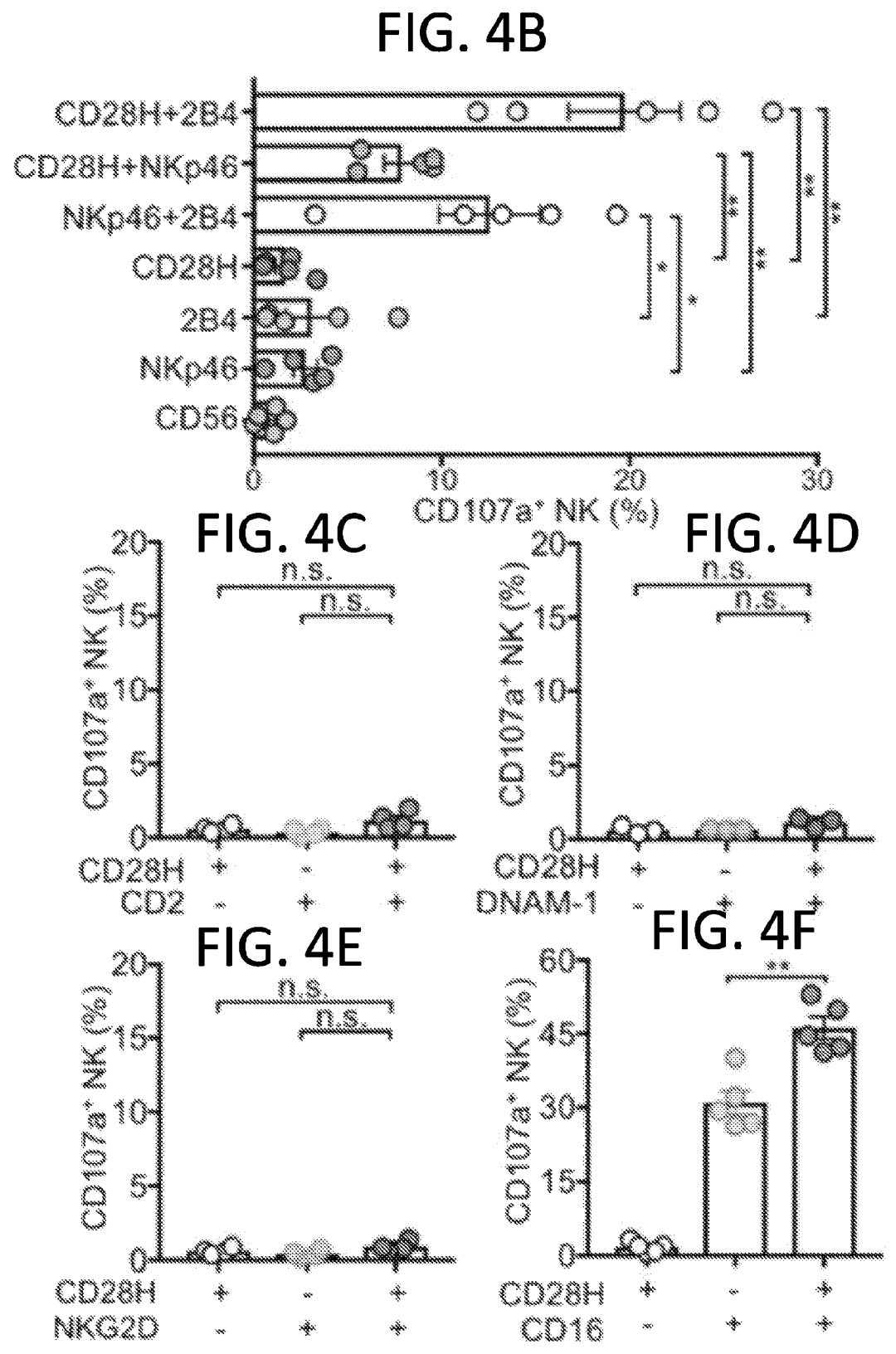

CD28H synergizes with 2B4 and NKp46 and enhances NK cell activation by CD16: NK-cell degranulation induced by CD28H alone and CD28H co-engaged with other receptors was tested using the redirected cytotoxicity assay (also known as reverse ADCC) (Bryceson et al., *Blood* 107:159-166, 2006; Vitale et al., *J. Exp. Med.* 187:2065-2072, 1998). The FcR$^+$ mouse cell line P815 was mixed with monoclonal antibodies (mAbs) to CD28H and other receptors and incubated with NK cells. The F(ab')$_2$ portions of the mAbs bound to their respective NK cell receptors, whereas the Fc fragments bound to FcR on mouse P815 cells. Activation of NK cells and lysis of P815 cells were induced by co-engagement of NK activation receptors (FIG. 3A). Strong NK-cell degranulation, determined by staining for CD56 and CD107a, occurred only after co-engagement of CD28H with either 2B4 or NKp46 (FIGS. 4A and 4B), but not with CD2, NKG2D, or DNAM-1 (FIGS. 4C-4E). CD56$^{dim}$ NK cells in peripheral blood are competent in both cytotoxicity and cytokine production, whereas CD56$^{bright}$ NK cells are less cytotoxic and have been viewed as cytokine producers (Cooper et al., *Trends Immunol.* 22:633-640, 2001; Fauriat et al., *Blood* 115:2167-2176, 2010). Therefore, although a slightly greater fraction of CD56$^{bright}$ NK cells expressed CD28H (FIG. 1B), NK-cell degranulation was observed only on CD56$^{dim}$ NK cells (FIG. 4A), consistent with previous studies (Bryceson et al., *Blood* 107:159-166, 2006; Bryceson et al., *Blood* 114:2657-2666, 2009). CD28H also enhanced the NK-cell degranulation induced by CD16 (FIG. 4F). To titrate the response of NK cells to stimulation through CD28H, mAbs to 2B4, NKp46, and CD16 were used at a constant concentration in redirected cytotoxicity assays in the presence of increasing concentrations of CD28H antibody (FIGS. 4G-4I). Enhancement of degranulation was observed with as low as 100 ng/ml CD28H antibody, and stimulation reached a plateau at about 5 μg/ml (FIGS. 4G-4I). Lysis of P815 cells in this redirected cytotoxicity assay was also investigated at different effector to target ratios (FIGS. 4J-4K). NK cells lysed P815 target cells efficiently upon co-engagement of CD28H with 2B4 and NKp46, and none of the three receptors alone triggered NK cell cytotoxicity (FIGS. 4J-4K).

Figures 3B, 3C:
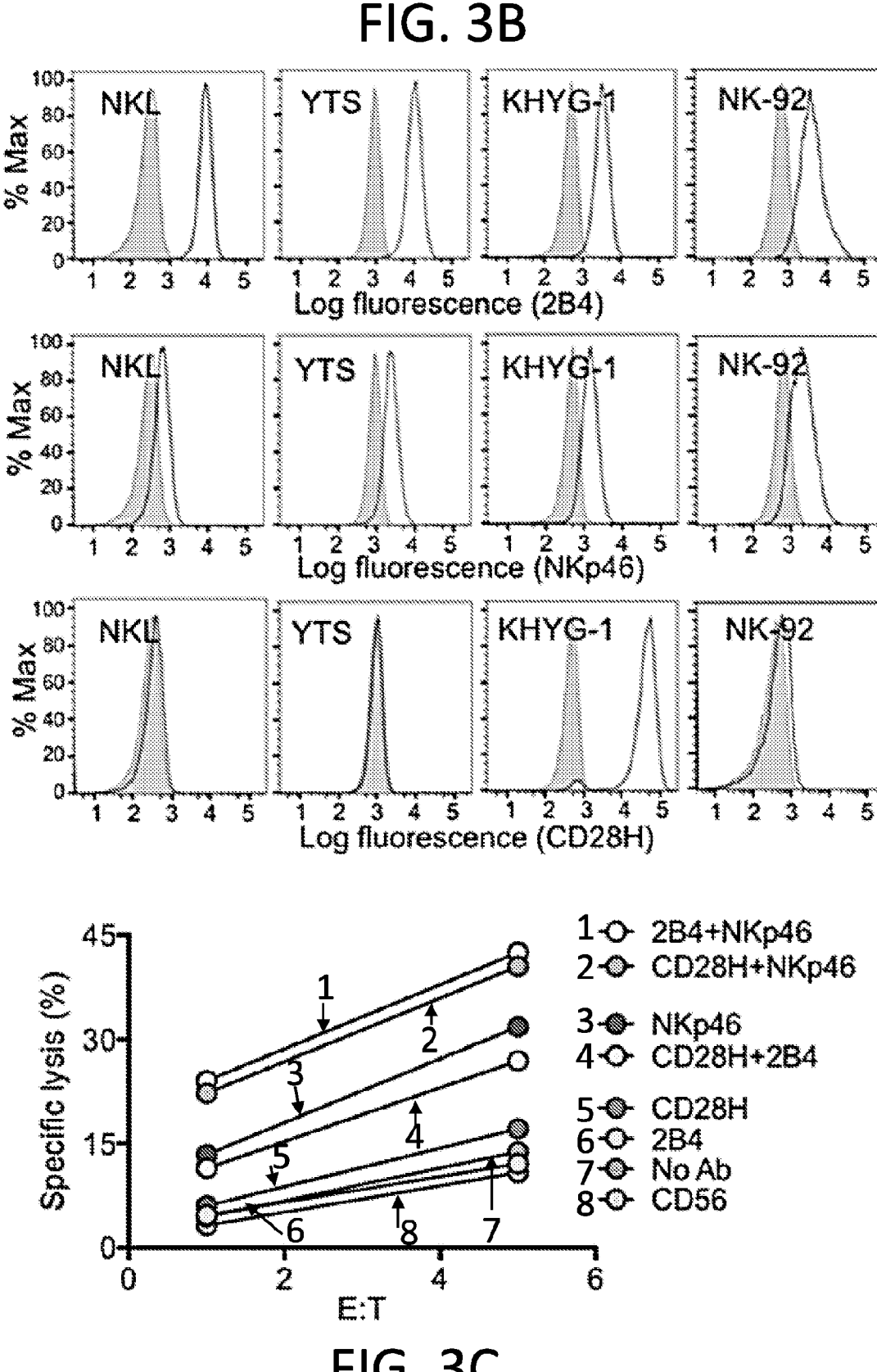

Among four commonly used NK cell lines, namely NKL, YTS, KHYG-1, and NK-92, only KHYG-1 expressed CD28H, whereas all four expressed 2B4 and NKp46 (FIG. 3B). KHYG-1 cells lysed P815 target cells in the presence of antibodies to CD28H and 2B4, or CD28H and NKp46 (FIG. 3C). Therefore, the synergy of CD28H with 2B4 and NKp46 observed with resting NK cells was reproduced with KHYG-1 cells.

Figures 6A, 6B:
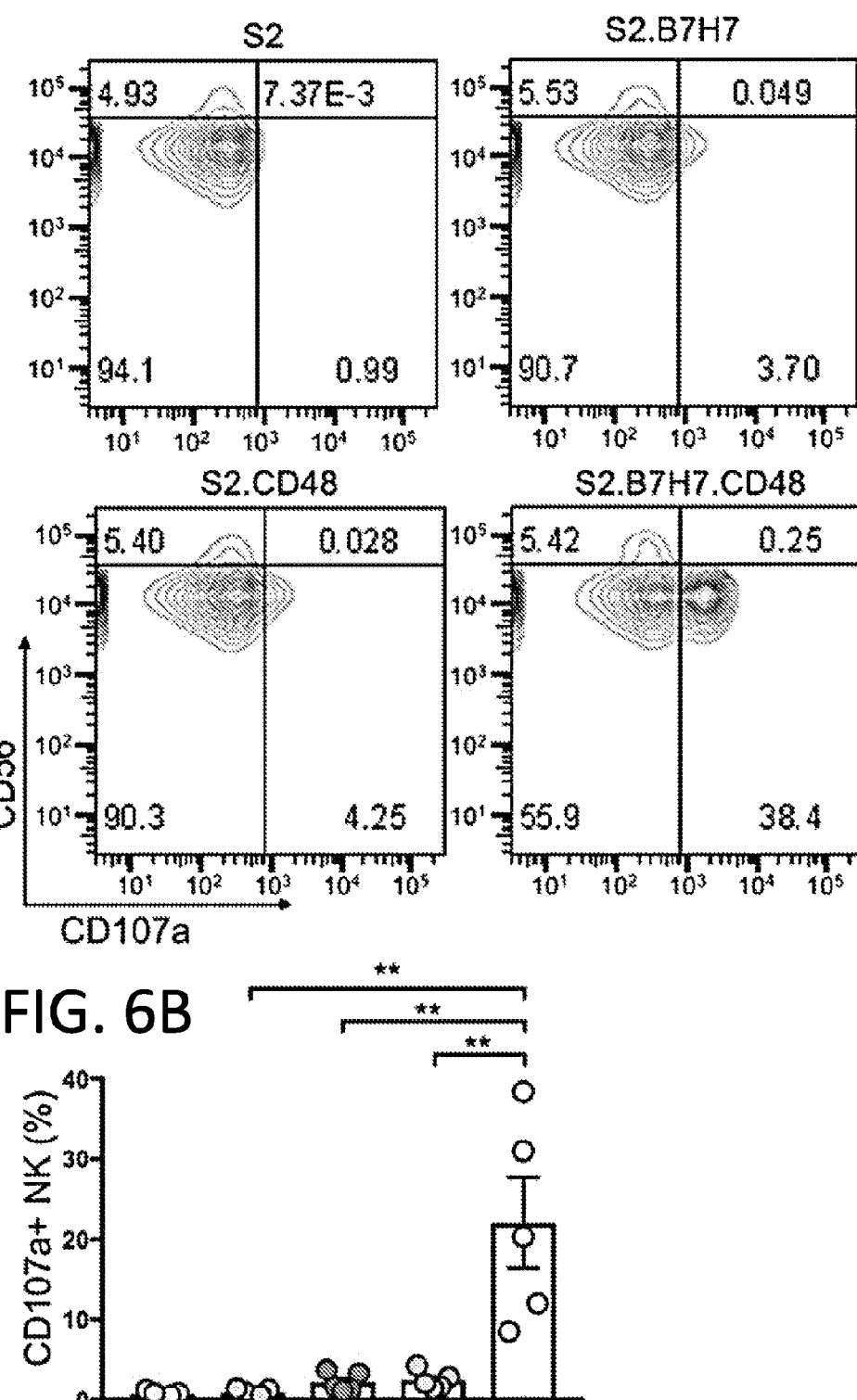
Figures 6E, 6F:
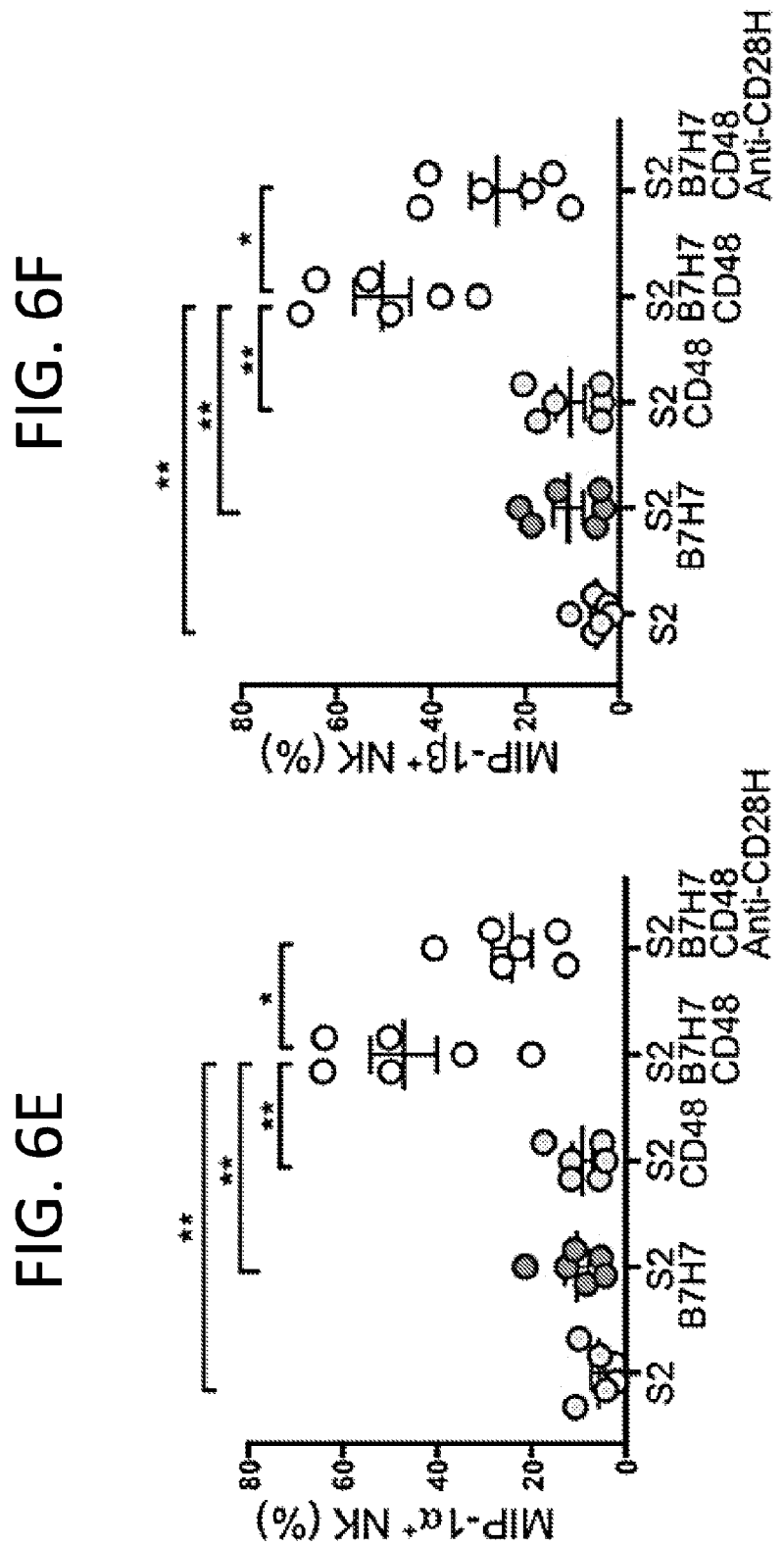

B7H7 and CD48 coexpression triggers NK-cell degranulation and cytokine production: To study the synergistic activation of NK cells by CD28H and 2B4 in the context of receptor-ligand interactions, we expressed B7H7 and CD48, either alone or in combination, in *Drosophila* S2 cells (FIG. 5A). CD48, which is expressed on most hematopoietic cells, is the ligand of 2B4. NK cells incubated with S2 cells expressing B7H7 (S2.B7H7) or CD48 (S2.CD48) for 2 hours did not degranulate (FIG. 6A). In contrast, S2 cells expressing both B7H7 and CD48 induced NK-cell degranulation (FIGS. 6A-6B). The results showed that engagement of both CD28H and 2B4 by their respective ligands lead to synergistic activation of NK cells. Coexpression of B7H7 and CD48 on S2 cells induced production of IFNγ, TNFα, MIP-1α, and MIP-1β in primary NK cells (FIGS. 6C-6F). As observed with NK-cell degranulation, cytokine and chemokine production was triggered only by synergy of CD28H and 2B4, but not by either receptor alone. Moreover, expression of IFNγ, TNF-α, MIP-1α, and MIP-1β was reduced in the presence of a CD28H blocking antibody (FIGS. 6C-6F), confirming stimulation through CD28H. Although CD48 and B7H7 alone stimulated a small proportion of NK cells to express MIP-1α, B7H7 and CD48 together induced strong NK cell responses—approximately 70% of NK cells expressed MIP-1α, and approximately 10% of NK cells had at least 3 different responses (FIG. 5B). It is worth noting that degranulating NK cells and IFNγ-producing NK cells were only partially overlapping. Moreover, the blocking antibody toward CD28H attenuated all of the NK responses.

Figure 7A:
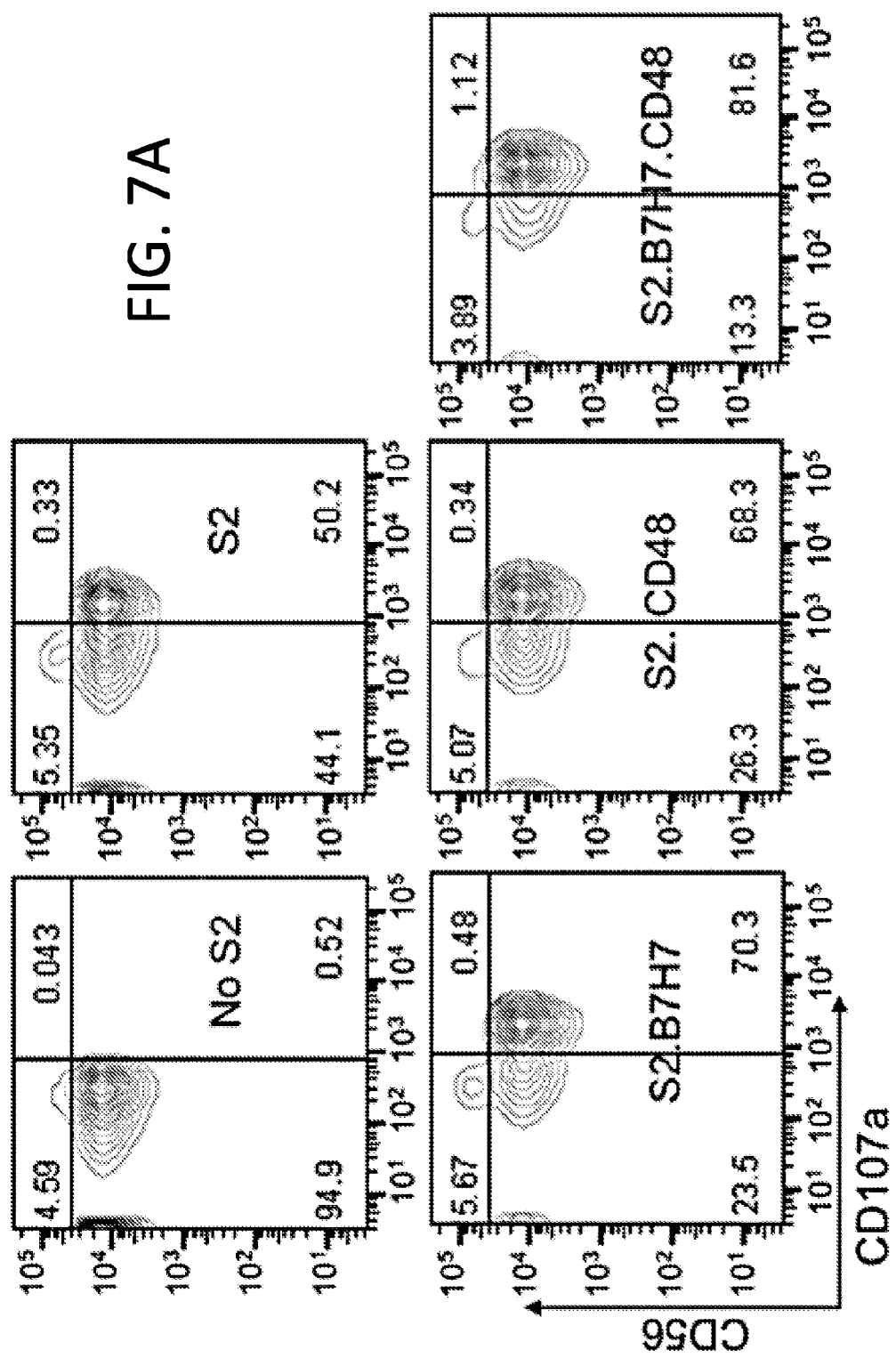
FIGS. 7A-7E show that B7H7 on target cells enhances ADCC by NK cells.
Figure 7B:
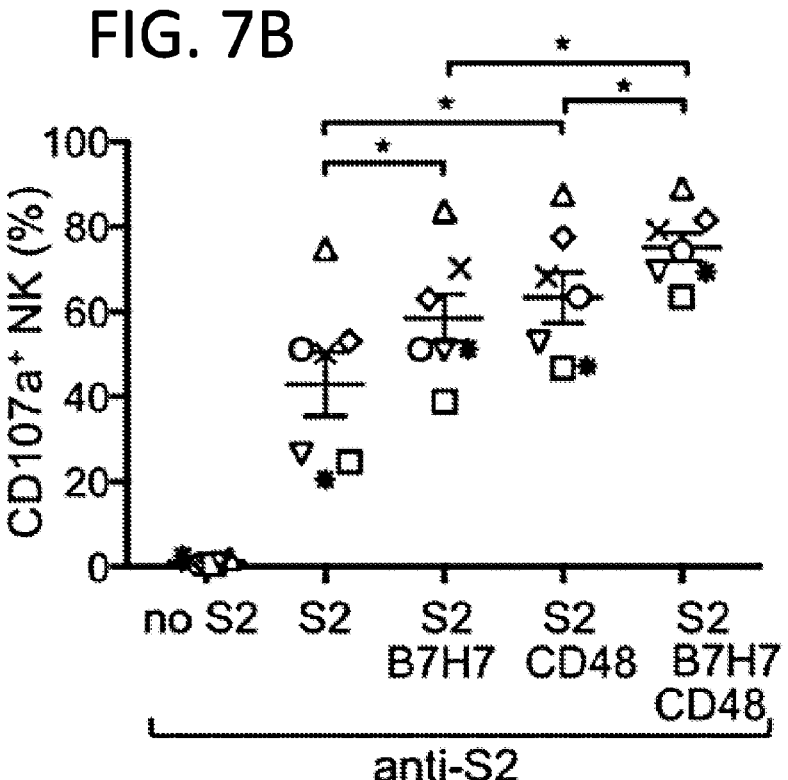
Figure 7C:
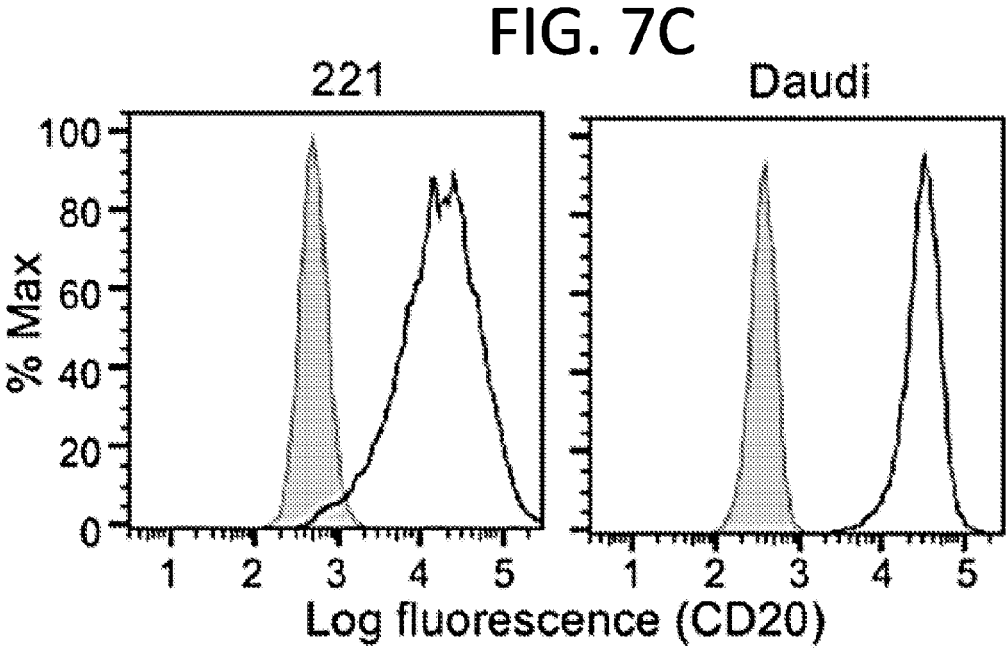
Figures 7D, 7E:
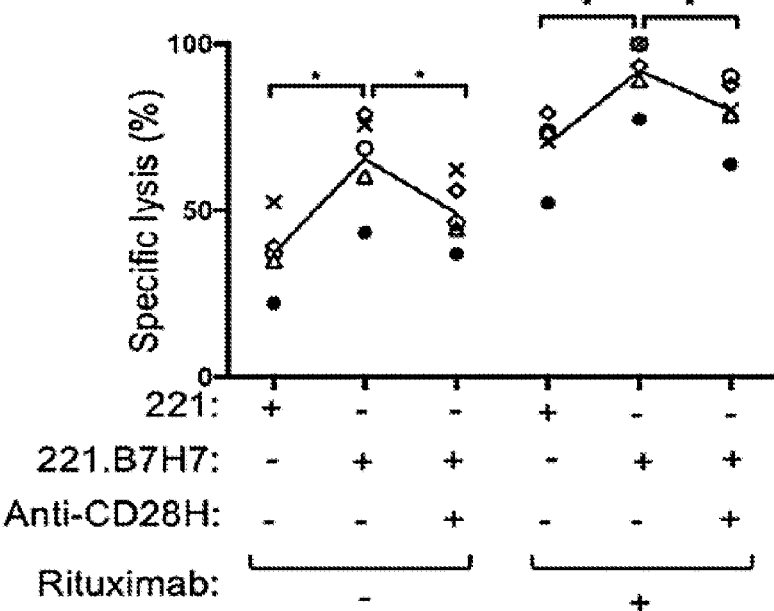
Figure 8A:
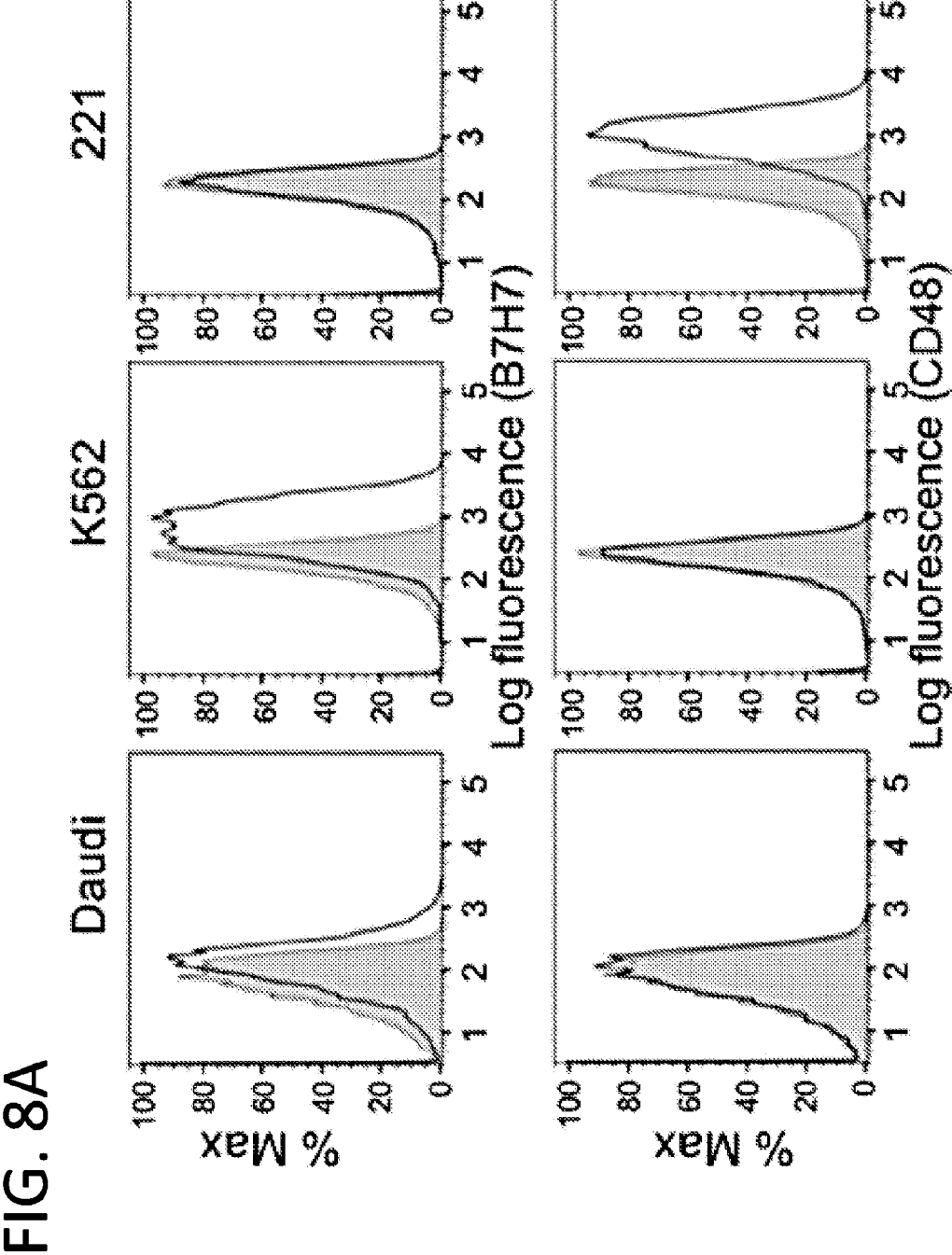
FIGS. 8A-8C show that B7H7 on 221 cells promotes CD28H-dependent lysis by NK cells.
Figures 8B, 8C:
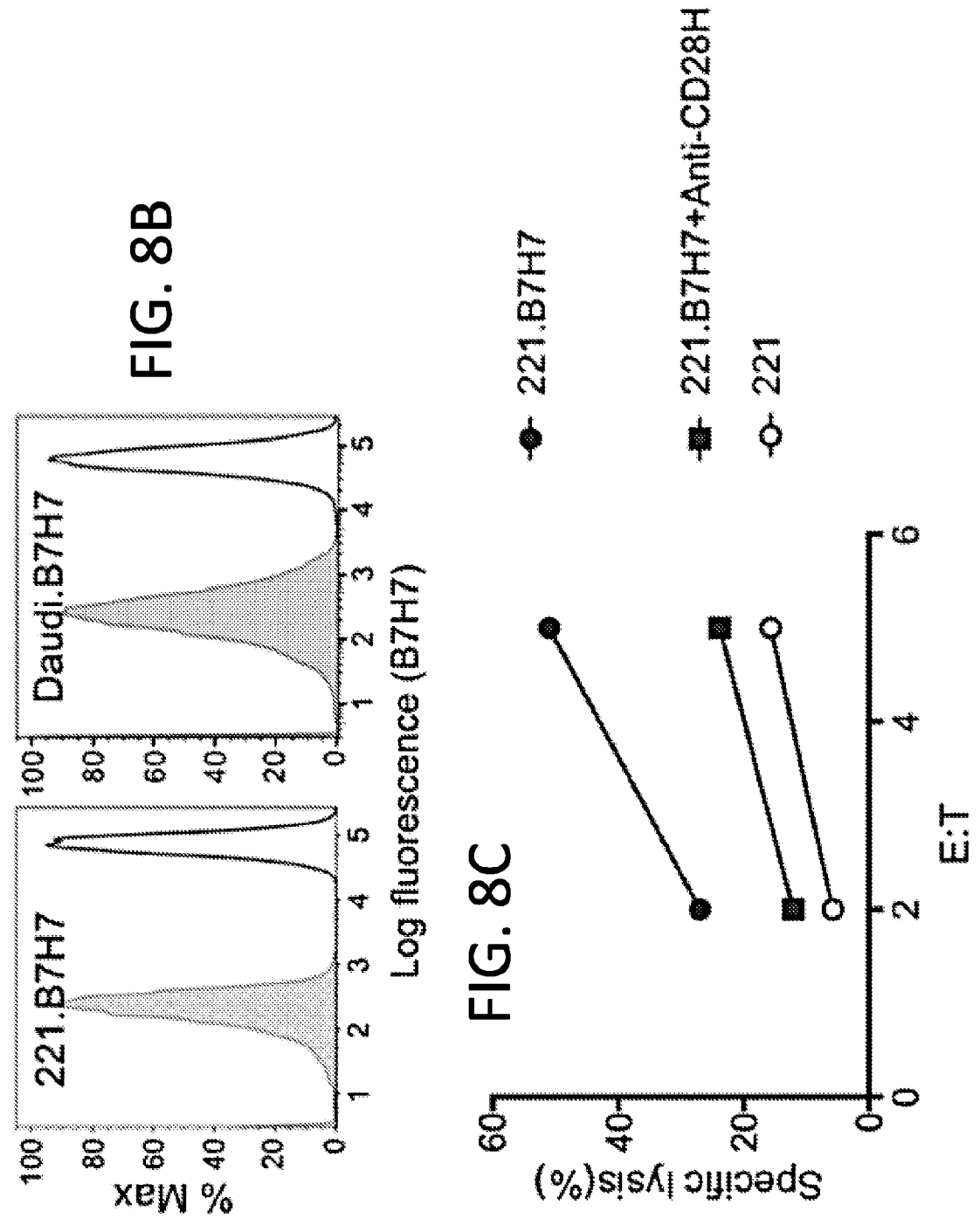

CD28H enhances CD16-mediated ADCC: To explore the possible enhancement of NK cell-mediated ADCC by CD28H, assays were performed with a rabbit antiserum to S2 cells (Bryceson et al., *Blood* 107:159-166, 2006). S2 cells were precoated with anti-S2 serum, followed by incubation with primary human NK cells. Expression of B7H7 in S2 cells enhanced NK activation in the ADCC assay, whereas expressing both B7H7 and CD48 increased NK degranulation even further (FIGS. 7A and 7B). NK cell-mediated ADCC plays a central role in the mechanism of action of therapeutic antibodies, such as rituximab (anti-CD20) and cetuximab (anti-EGFR) (Scott et al., *Nat Rev Cancer* 12:278-287, 2012). Three MHC class I-deficient cell lines commonly used as targets for NK cells were examined for expression of B7H7 (FIG. 8A). B7H7 was expressed by K562 cells, but not Daudi or 221 cells (FIG. 8A). Among these three cell lines, only 221 expressed CD48 (FIG. 8A). We transduced 221 and Daudi cells with a lentivirus for expression of B7H7 and obtained bright and uniform expression of B7H7 (FIG. 8B). Freshly isolated human NK cells lysed 221 cells expressing B7H7 (221.B7H7) more efficiently than untransfected 221 cells (FIG. 8C). The enhanced lysis of 221.B7H7 was blocked by a CD28H specific mAb (FIG. 8C). As Daudi and 221 cells are both CD20+ lymphoblastoid B-cell lines (FIG. 7C), we used rituximab to induce ADCC. Specific lysis of target cells in rituximab-induced ADCC was increased by the expression of B7H7, and the enhancement in killing was specifically blocked by CD28H antibody (FIGS. 7D and 7E). We concluded that the CD28H-B7H7 interaction enhanced natural killing of 221 and Daudi cells by primary NK cells, as well as lysis of 221 and Daudi cells through ADCC.

Figure 9A:
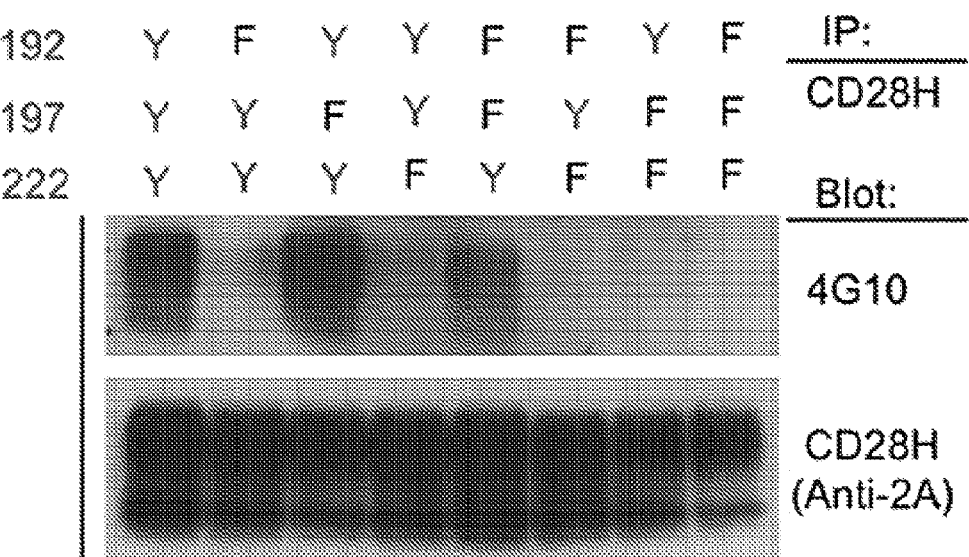
FIGS. 9A-9F illustrate that Tyr192 of CD28H is essential for CD28H-mediated NK-cell activation.
Figure 9B:
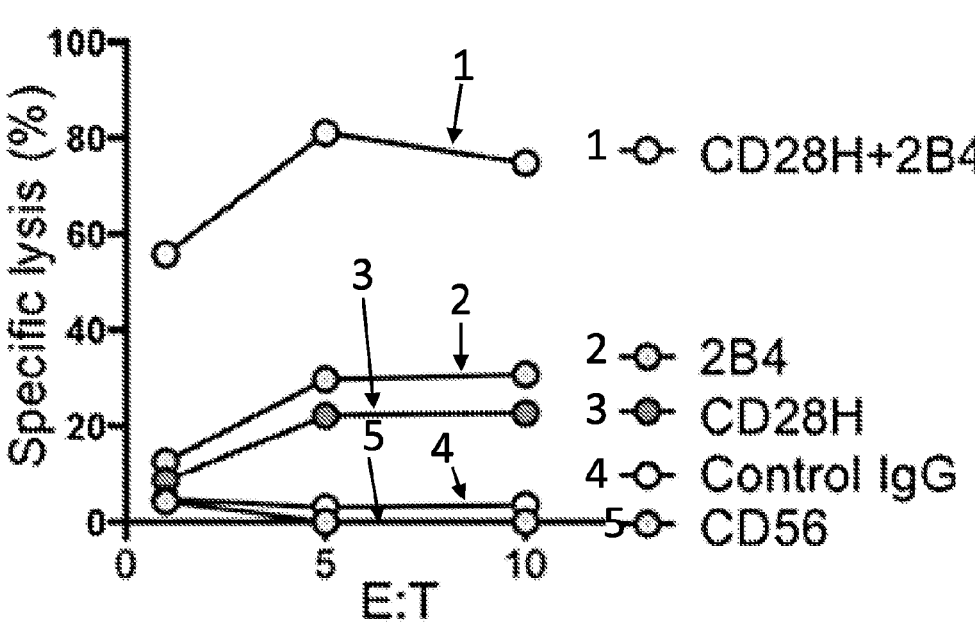
Figure 9C:
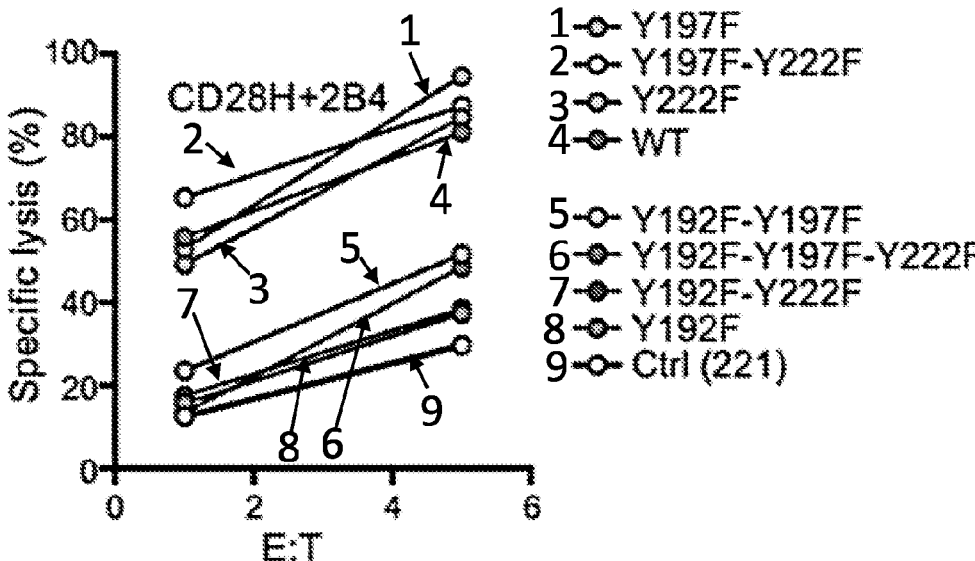
Figure 9D:
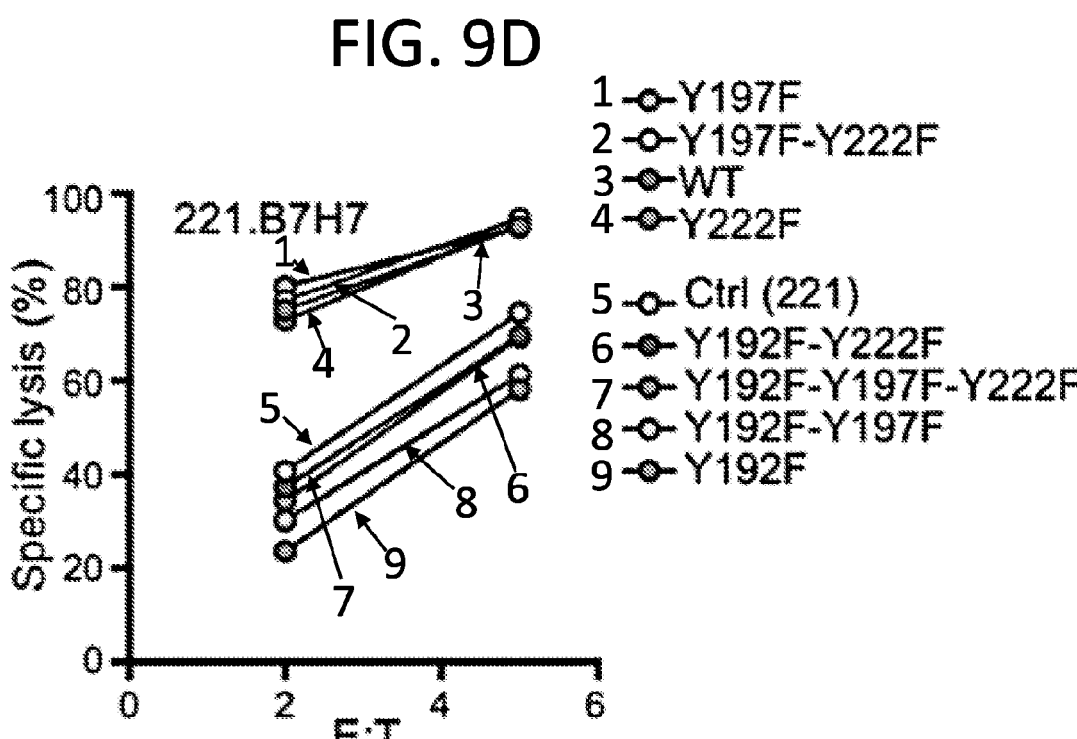
Figure 9E:
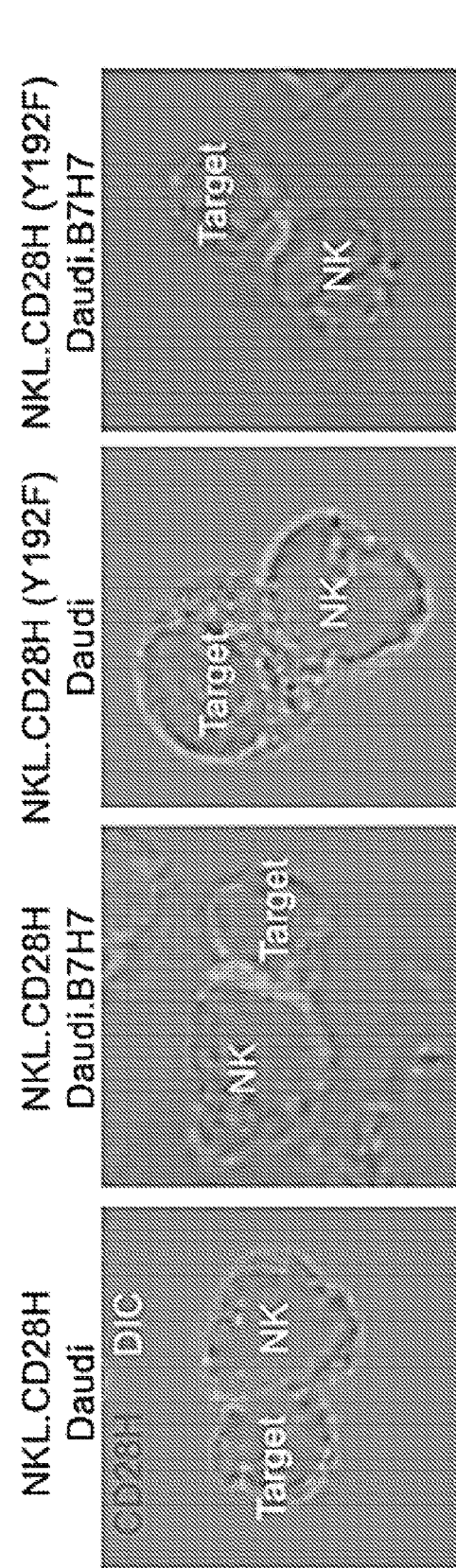
Figure 9F:
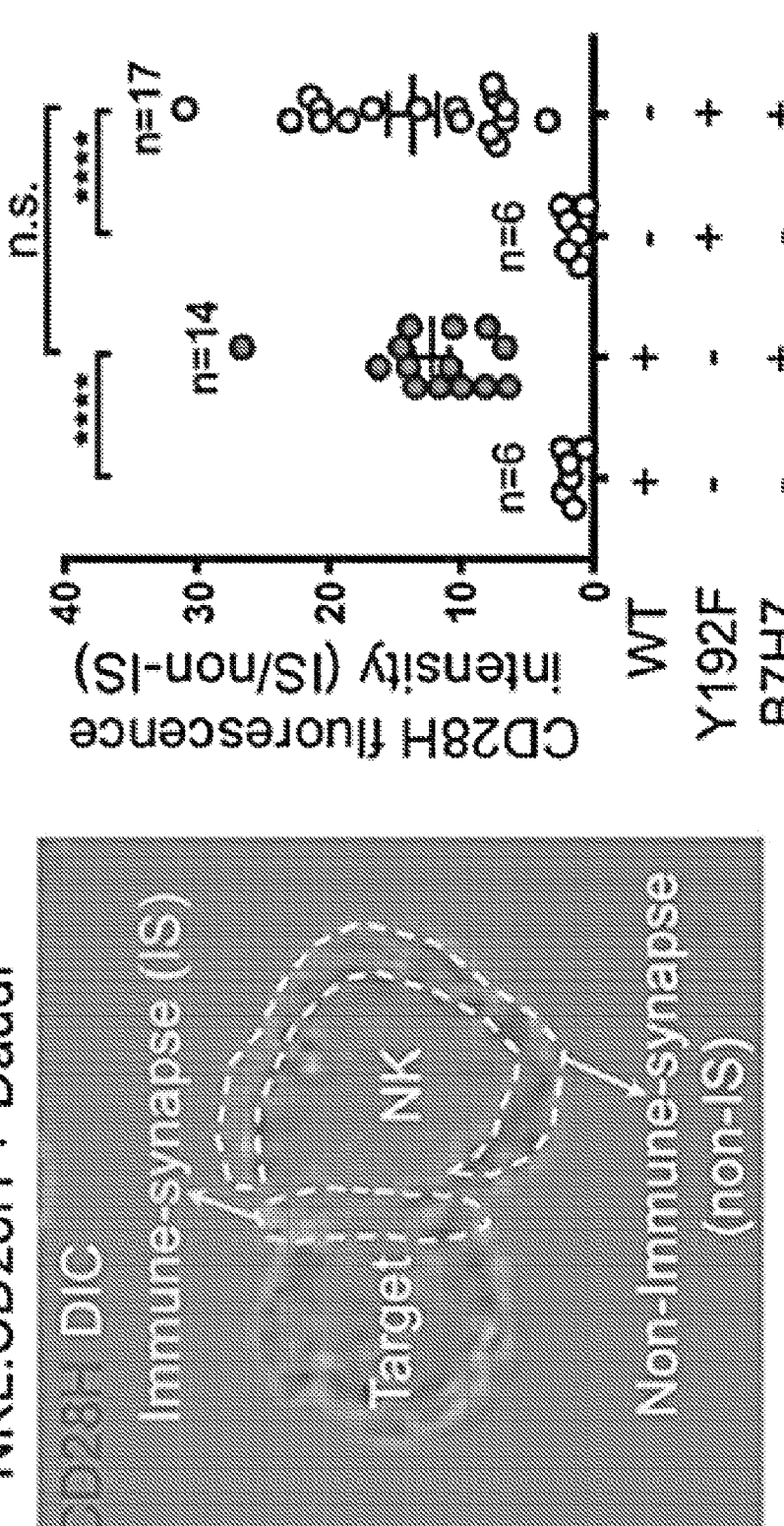
Figure 10:
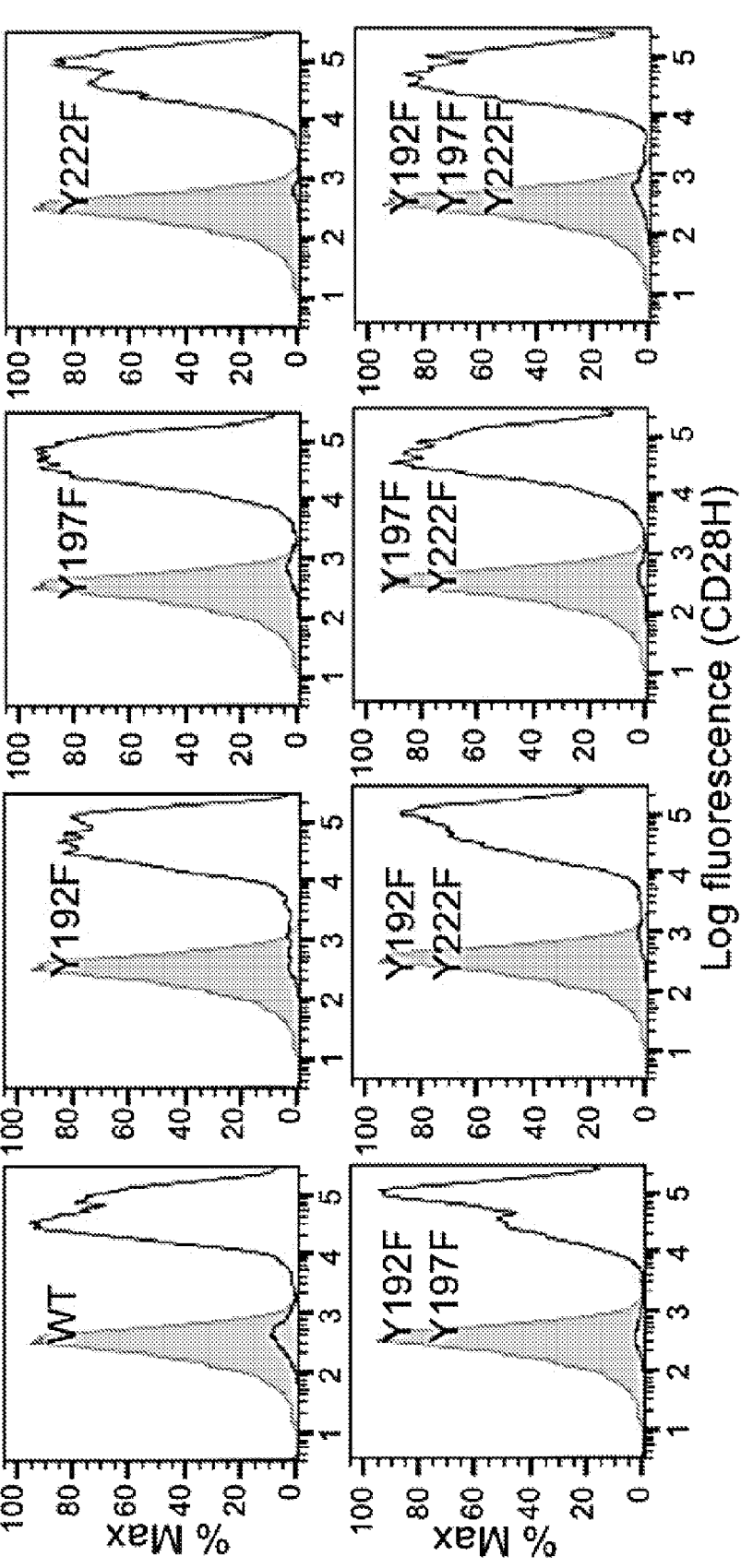
FIG. 10 shows CD28H expression on NKL cells transfected with the indicated CD28H mutants. Shaded histograms represent staining of untransfected cells.

Tyr192 is essential for CD28H-mediated NK-cell activation: The CD28H cytoplasmic tail includes three tyrosines, which could potentially contribute to transduction of activation signals. Each tyrosine was replaced with a phenylalanine, in all possible combinations. CD28H wild-type and each one of the mutants were immunoprecipitated from transfected HEK293T cells after treatment with the tyrosine phosphatase inhibitor pervanadate. Tyrosine phosphorylation was greatly diminished by mutation of either Y192 or Y222 (FIG. 9A). The function of each of the mutants was tested by expressing them in an NK cell line. Exogenous expression of wild-type CD28H in the CD28H⁻ 2B4⁺ cell line NKL reproduced the synergy of CD28H and 2B4, as shown in the redirected ADCC assay with P815 cells (FIG. 9B). CD28H mutants were expressed in NKL cells to test the contribution of each tyrosine to CD28H-dependent activation of NK cells (FIG. 10). Single-site mutation of Y192 (Y192F) abolished synergistic activation by CD28H and 2B4 (FIG. 9C). Lysis of 221.B7H7 cells by NKL cells expressing wild-type CD28H and CD28H mutants was also investigated. Consistent with the redirected cytotoxicity assays, enhancement of killing of 221 cells by B7H7 expression was also lost with mutation Y192F (FIG. 9D), indicating that phosphorylation of Y192 may be essential for NK-cell activation. The Y192F mutation did not alter accumulation of CD28H at the immunological synapse (FIGS. 9E and 9F), suggesting that the accumulation of CD28H and its ability to signal for cytotoxicity were uncoupled. There are multiple stages in the formation of NK cell immunological synapses (Orange *Nat. Rev. Immunol.* 8:713-725, 2008). The accumulation of mutant Y192F at the synapse indicated that signals specifically triggered by Y192 are not required for that stage of synapse formation. In addition to the three tyrosine residues in the cytoplasmic tail, CD28H also contains a proline-rich domain, which may be involved in signal transduction.

Figure 11A:
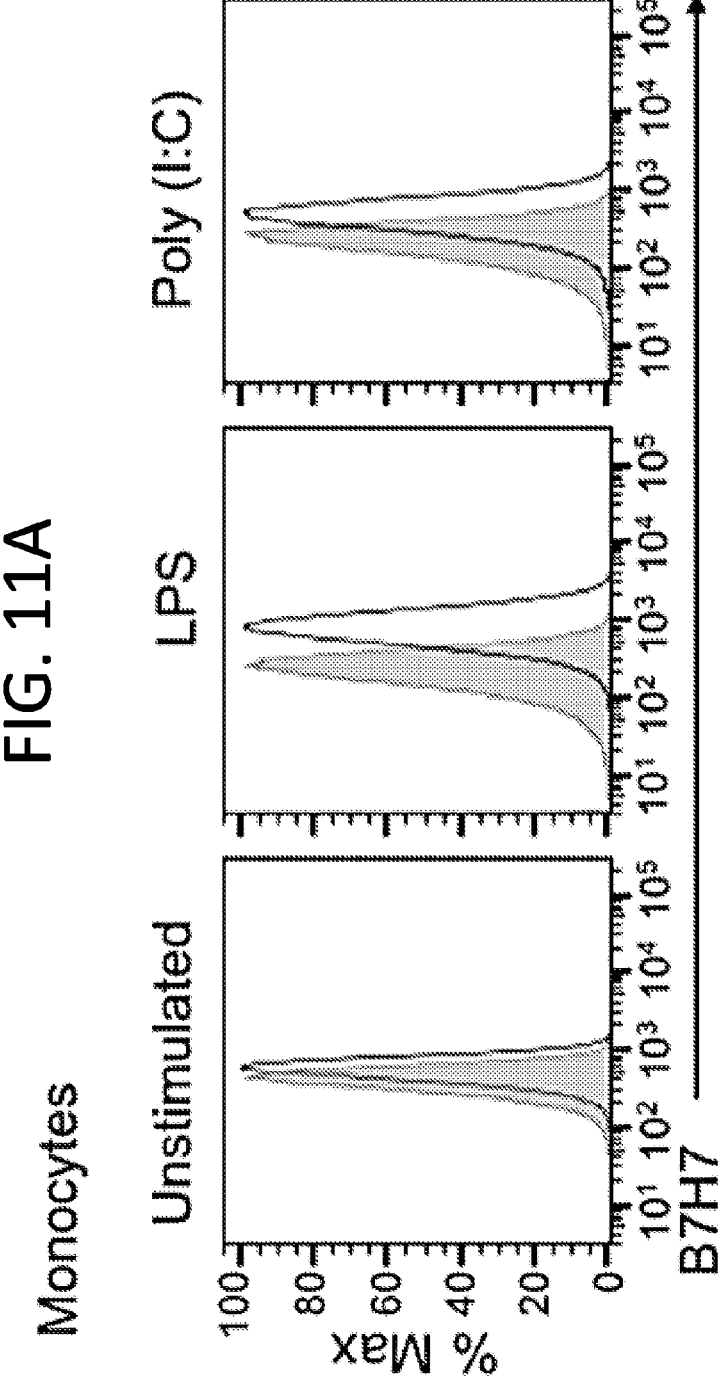
FIGS. 11A and 11B show B7H7 expression on circulating monocytes and myeloid dendritic cells.
Figure 11B:
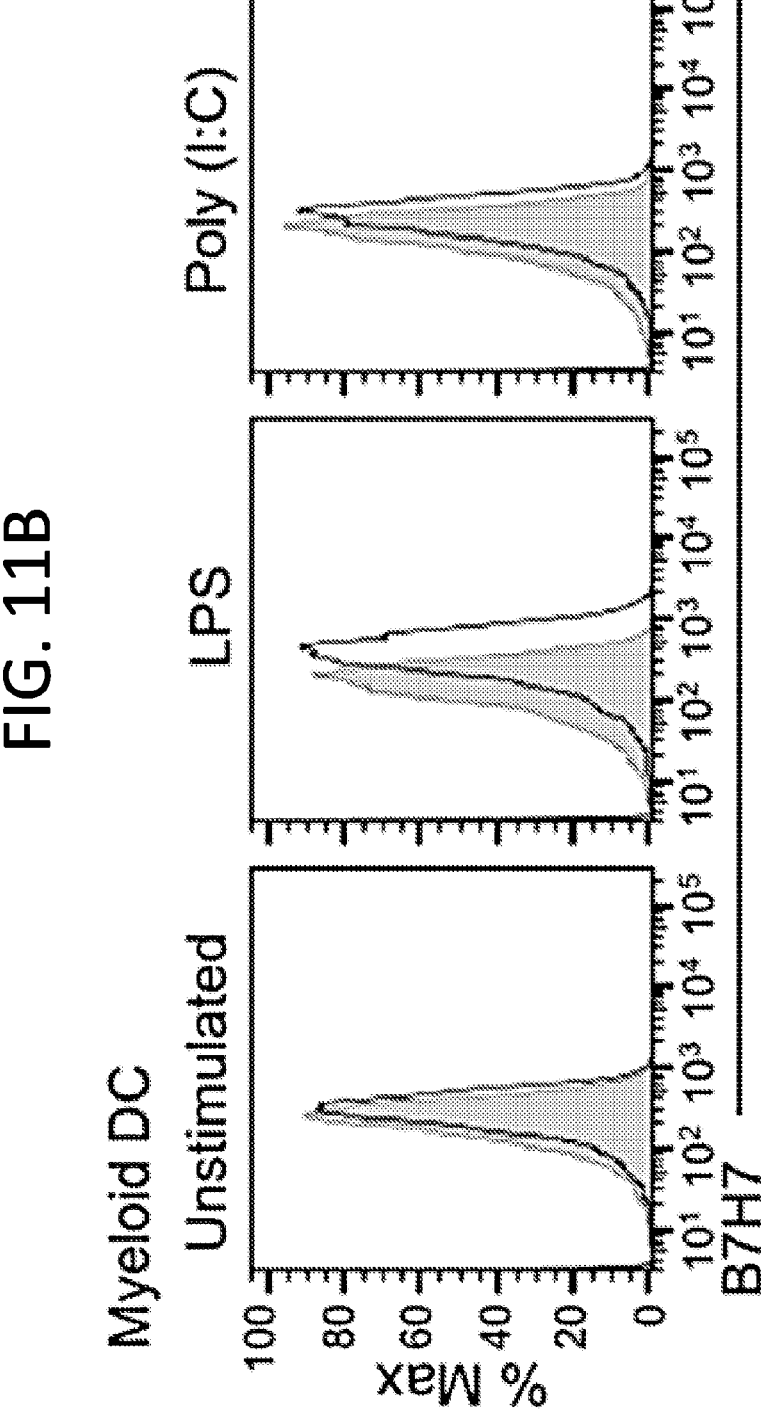
Figures 12A, 12B, 12C:
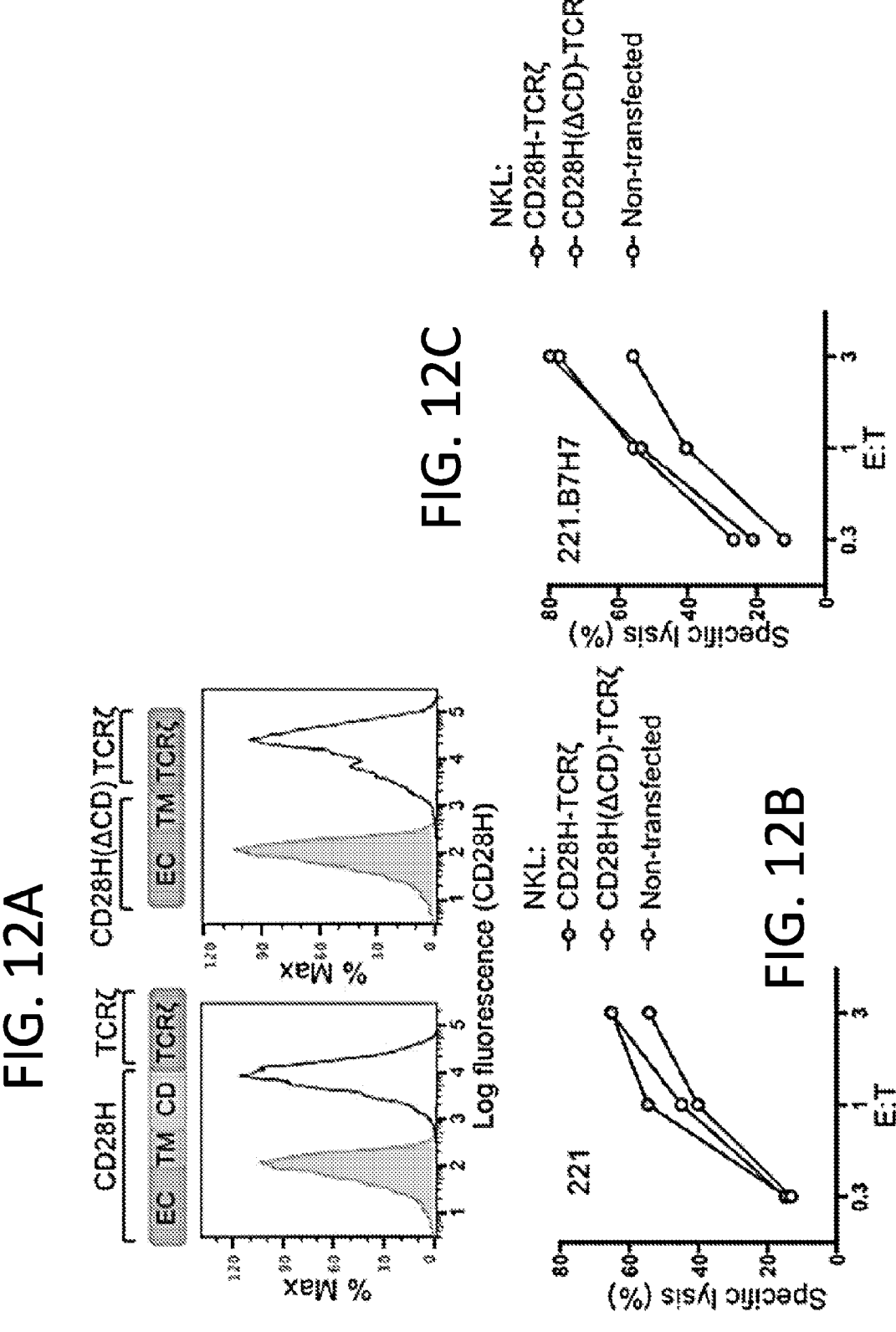
Figures 12D, 12E:
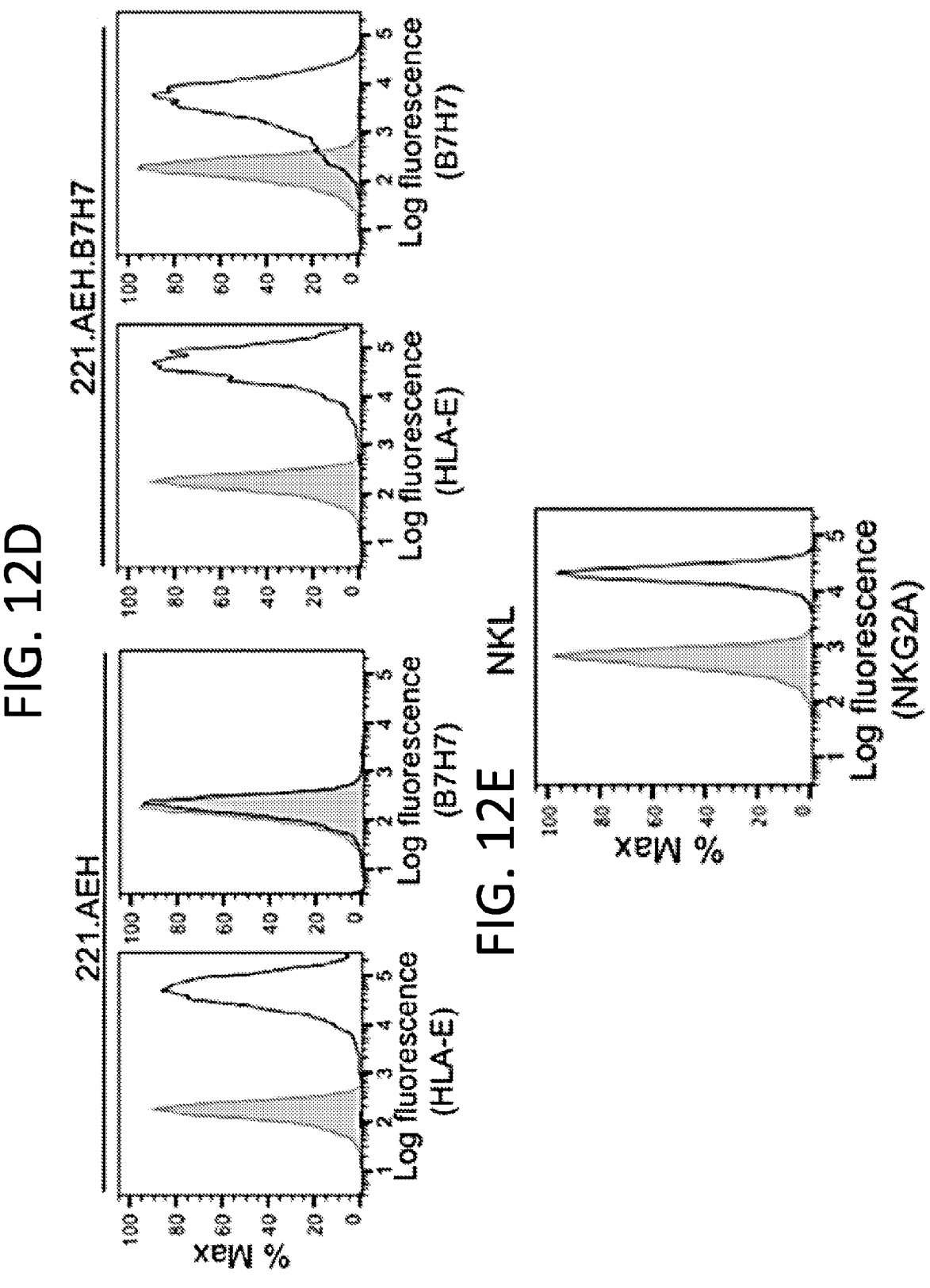

NK cells with a CD28H-CAR kill B7H7⁺ tumor cells by overriding inhibition by NKG2A: Expression of the CD28H ligand B7H7 is limited to activated myeloid cells (Zhu et al., *Nat. Commun.* 4; 2043, 2013; Zhao et al., *PNAS* 110:9879-9884, 2013) and tumor cells (Janakiram et al., *Clin. Cancer Res.* 21:2359-2366, 2015). We have detected marginal expression of B7H7 on monocytes and DCs activated by LPS or poly(I:C) (FIGS. 11A and 11B). The broader expression of B7H7 in tumor tissues motivated us to explore the possibility of utilizing the CD28H-B7H7 interaction to target tumors in cancer immunotherapies. We constructed two CD28H CARs by fusing full-length or cytoplasmic domain-truncated (ΔCD) CD28H with the signal transduction domain of the TCR ζ chain (FIG. 12A and SEQ ID NOs: 1-4). Expression of the CD28H-CARs in NKL cells (FIG. 12A) did not significantly alter the cytotoxic activity toward untransfected 221 cells (FIG. 12B), and enhanced killing of 221.B7H7 cells (FIG. 12C). The nonclassical MHC-I antigen HLA-E binds inhibitory receptor NKG2A on NK cells and suppresses NK-cell activation (Long et al., *Annu. Rev. Immnuol.* 31:227-258, 2013). To test whether CD28H or CD28H-CARs were capable of overcoming NKG2A-mediated inhibition, 221.AEH cells, which express HLA-E at the cell surface, were transfected with B7H7 (FIG. 12D). NKL cells express NKG2A (FIG. 12E). Cytotoxicity of NKL.CD28H and NKL.CD28H-CAR cells toward 221.AEH cells was low, presumably due to inhibition by NKG2A (FIG. 12F). Remarkably, NKL.CD28H-TCRζ cells killed 221.AEH.B7H7 cells, indicating that NKG2A-mediated inhibition was overcome by the CD28H-B7H7 interaction (FIG. 12G). Expression of wild-type CD28H alone or CD28HΔCD-TCRζ chimeric receptor in NKL did not overcome NKG2A inhibition, indicating the essential costimulatory function of CD28H in the CD28H-TCRζ chimera (FIG. 12G). We used the B7H7⁺ Hodgkin's lymphoma cell line HDLM-2 to further test the antitumor activity of CD28H-CARs (FIG. 12H). HDLM-2 cells, which express HLA-E (FIG. 12H), were lysed by the CD28H⁺NKG2A⁺ KHYG-1 NK cell line only after blocking the NKG2A-HLA-E interaction with a mAb to NKG2A (FIG. 12I).

Figure 12J:
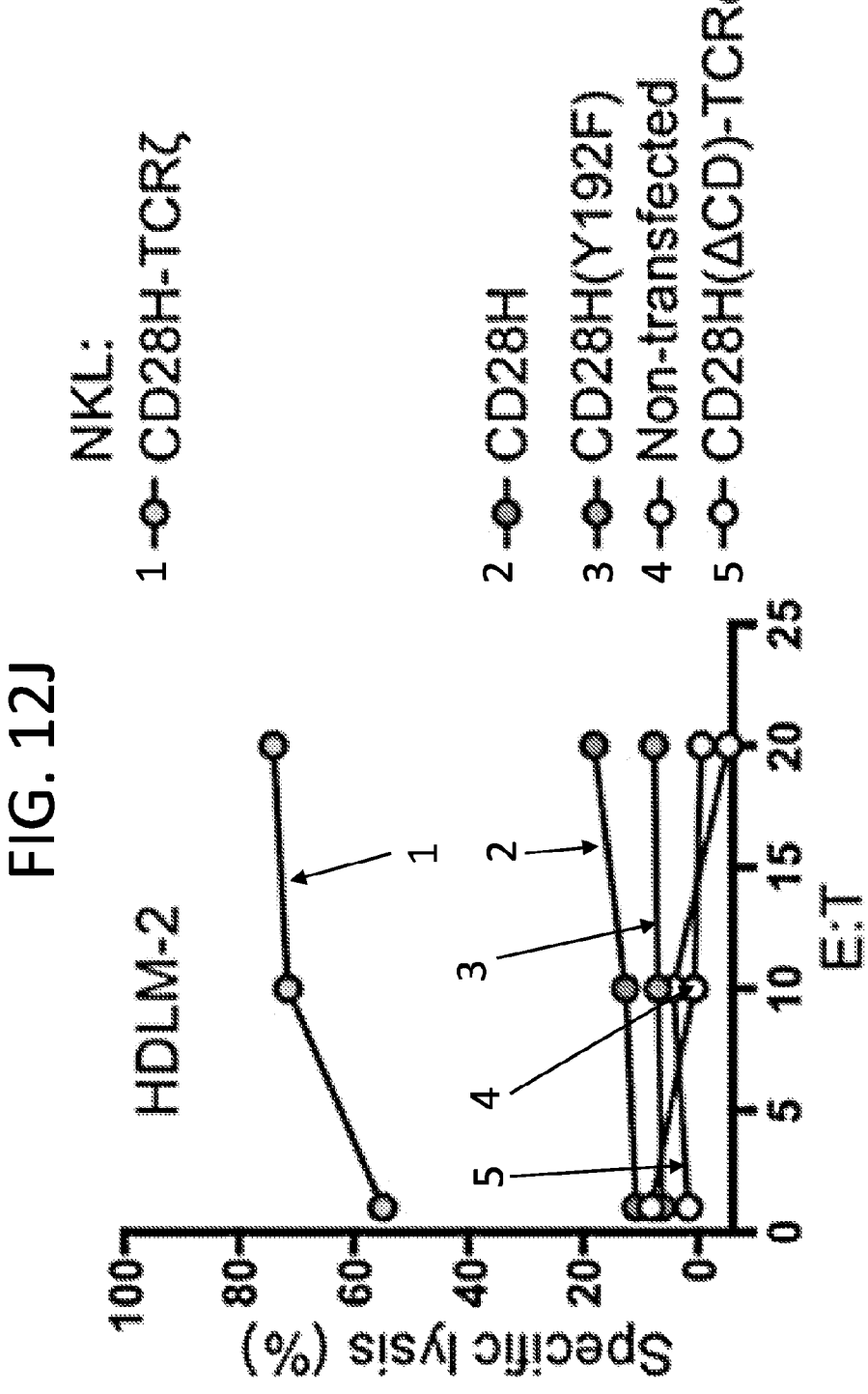

However, NKL cells expressing the CAR with full-length CD28H achieved efficient killing of the B7H7$^+$ HLA-E$^+$ HDLM-2 tumor cells (FIG. 12J), showing that CD28H-CARs have antitumor activity and therapeutic potential.

Discussion

We showed that most NK cells in circulating blood express CD28H, a member of the CD28 receptor family that has been described in T cells. Co-engagement of CD28H with 2B4 resulted in synergistic activation of freshly isolated NK cells for degranulation, target cell lysis, and expression of cytokines and chemokines. CD28H is an addition to the family of NK cell coactivation receptors and synergizes with 2B4 and NKp46, but not with NKG2D, CD2, or DNAM-1. CD28H expression is turned off during prolonged activation with IL2. Downregulation of CD28H has also been observed in human T cells after antigenic stimulation. NK cells freshly isolated from peripheral blood, which are commonly referred to as 'resting,' are nevertheless fully functional even in the absence of IL2 and IL15. Co-engagement with CD28H also enhanced CD16-mediated NK-cell degranulation and cytotoxicity. Unlike coactivation receptors that require synergy, CD16 signaling in NK cells is sufficient to activate cytotoxicity. Other activation receptors, such as 2B4, CD2, NKG2D, and DNAM-1 have also been reported to enhance ADCC.

We and others have shown that B7H7 expresses on activated myeloid cells. Considering the fact that CD48 is broadly expressed on hematopoietic cells, the expression of B7H7 on activated myeloid cells might contribute to the interaction between NK cells and APCs. The involvement of other potential synergies between CD28H and other activation receptors might add another layer of complexity to the regulation of NK-APC interactions and immune homeostasis. In fact, activating receptors such as NKp30 and NKG2D have been reported as regulators of NK-DC interactions. Besides its costimulatory function, B7H7 can also have a coinhibitory effect on T cells and has been proposed as an immune checkpoint inhibitor. In the context of this Example, there was no inhibitory effect of B7H7 toward NK cell lines and primary NK cells in the functional assays performed here, including degranulation, target cell lysis, and cytokine expression. However, expression of checkpoint coinhibitory receptors, such as PD-1 and LAG-3, is usually induced or upregulated on NK cells after activation. It is possible that expression of a coinhibitory receptor for B7H7 is induced on NK cells by activation or other stimulations.

We tested the contribution of B7H7 expressed on cell lines to the activation of NK cells through CD28H. The mutant cell line 221 is sensitive to NK cell cytotoxicity due to the loss of several MHC-I ligands for NK cell inhibitory receptors. Expression of B7H7 on 221 cells rendered them even more sensitive to NK cells. This could be explained by a synergy of CD28H with 2B4, the ligand of which, CD48, is expressed on 221. However, expression of B7H7 on 221 cells that expressed also HLA-E was not sufficient to overcome inhibition by NKG2A expressed on NK cell lines, which is consistent with the dominant inhibitory function of MHC-I specific receptors on NK cells.

The signaling basis of CD28H synergy with 2B4 and NKp46 is unknown. We showed that just one of the three tyrosine residues (tyrosine 192) in the cytoplasmic tail of CD28H is required and sufficient to coactivate NK cell cytotoxicity. Substitution of the other two tyrosines with phenylalanines did not impair CD28H-mediated NK-cell activation. Tyrosine 192 and adjacent amino acids form a sequence motif (YxN) that predicts binding of SH2 domains of the adaptor Grb2 and related proteins.

We tested the possibility of using CD28H itself as a CAR by fusing it to the intracellular domain of TCRζ. Expression of the CD28H-TCRζ CAR in NKL cells did not result in greater sensitivity of 221.B7H7 cells, which are already highly sensitive to lysis by NKL cells expressing CD28H. However, the CD28H-TCRζ CAR in NKL cells provided complete resistance to inhibition by NKG2A, as shown with 221 cells coexpressing B7H7 and HLA-E. Resistance to inhibition was also observed with a Hodgkin's lymphoma tumor cell, HDLM-2, that naturally expresses both B7H7 and HLA-E. As expected, CD28H$^-$ NKG2A$^+$ NKL cells did not kill HDML-2 cells. Remarkably, expression of the CD28H-TCRζ CAR in NKL cells resulted in very efficient lysis of HDML-2 cells, whereas neither the CD28H cytoplasmic tail nor the TCRζ chain on their own could overcome inhibition. The natural transmembrane domain and cytoplasmic tail of CD28H can now be added to the list of CAR components for use in NK cells.

Solutions proposed to overcome signaling by MHC-I specific inhibitory receptors on NK cells include silencing of inhibitory receptors concomitant with CAR expression in NK cells, or combining CAR-expressing NK cells with blockade of inhibitory receptors KIR and NKG2A with antibodies, some of which are already used in the clinic. A simpler and less costly approach is to design NK-tailored CARs that overcome inhibition by KIR and NKG2A in the context of tumor cells expressing HLA-C and HLA-E. As an example, the CD28H-TCRζ CAR was completely resistant to inhibition by NKG2A during contact with HLA-E$^+$ tumor cells. In summary, we have shown that CD28H is an activation receptor of NK cells, and we raised the possibility of utilizing CD28H for design of NK-CARs in order to overcome signaling by inhibitory receptors and to target tumors expressing B7H7.

Example 2

Inhibition-Resistant Chimeric Antigen Receptor in NK Cells Delivers Strong and Persistent Activation Signals Materials and Methods Cells: Isolation of human NK cells was performed as previously described. NKL cell line was obtained from M.J. Robertson (Indiana University Cancer Research Institute, Indianapolis, IN) and cultured in IMDM (Gibco) with 10% heat-inactivated fetal calf serum (FCS, Gibco). P815 cells (ATCC), 721.221 cells (referred as 221 cells), and HLA-E or HLA-C (Cw15) transfected 221 cells were cultured in RPMI-1640 (Gibco) supplemented with 10% heat-inactivated FCS.

Plasmids, lentivirus production: CAR constructs were either directly synthesized as gBlocks (IDT) or amplified by PCR from existing template, and then cloned into the EcoRI and NotI restriction sites of pCDH-EF1-T2A-Puro vector (System Biosciences). All plasmid constructions were performed using the In-Fusion HD cloning kit (Clontech). For production of lentivirus, low-passage Lenti-X 293T cells (Clontech) were transfected with PEI Max (polyethyleneimine) as described previously (Zhuang et al., *Cancer Immunol. Res.* 7:939-951, 2019). Culture media from *Lenti*-X 293T cells were collected 2 days after transfection and passed through a 0.45 µM filter. Culture media were directly used for transduction or concentrated using PEG-it (System Biosciences).

Cytotoxicity assay: Calcein-AM release assays were used to determine lysis of target cells by NK cells. Briefly, target cells at a final concentration of $10^6$/ml in complete media were incubated with 15 µM calcein-AM (Invitrogen) at 37° C. for 30 min. After 2 washes with complete media, labeled target cells were added to 96-well-plate at $10^4$/well. Effecter NK cells were added at different ET ratio and incubated for 4 hours. Target cell lysis was determined by fluorescence of released calcein-AM in the supernatants measured by a plate reader (Enspire, Perkin Elmer, MA and SpectraMax plus, Molecular Devices, CA).

Bead stimulation: Cells were stimulated with antibody-coated goat-anti-mouse Dynabeads (Invitrogen) at the ratio of 4 beads per cell. Antibodies used for bead coating included Myc-tag antibody (9B11, mouse IgG2a, Cell Signaling), NKG2A antibody (Z199, mouse IgG2b, Beckman Coulter), control mouse IgG2b (MOPC-141, Sigma), and control mouse IgG2a (UPC-10, Sigma). 107 beads were coated for 30 min at 37° C. with 2 µg total IgG at different combinations: 1 µg mIgG2a+1 µg mIgG2b, 1 µg mIgG2a+1 µg anti-NKG2A, 1 µg anti-Myc-tag+1 µg mIgG2b, or 1 µg anti-Myc-tag+1 µg anti-NKG2A. Beads were washed with 1% FCS hank's-balanced-salt-solution (HBSS, Corning) to remove excessive antibodies and resuspended in the same buffer. Pre-chilled beads and cells were mixed on ice and incubated in 37° C. water bath for 10 min or 45 min. Cells were washed and lysed before analyzing by western blot.

Results and Discussion

Figure 13C:
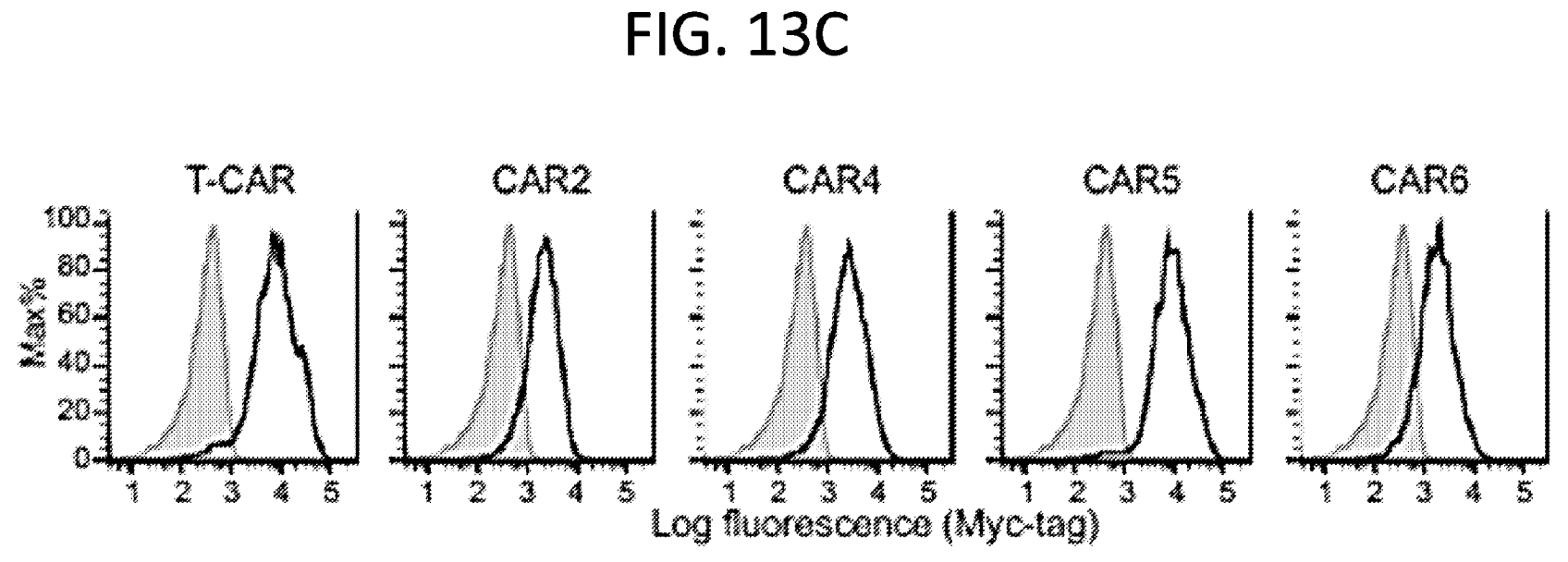
Figures 13D, 13E:
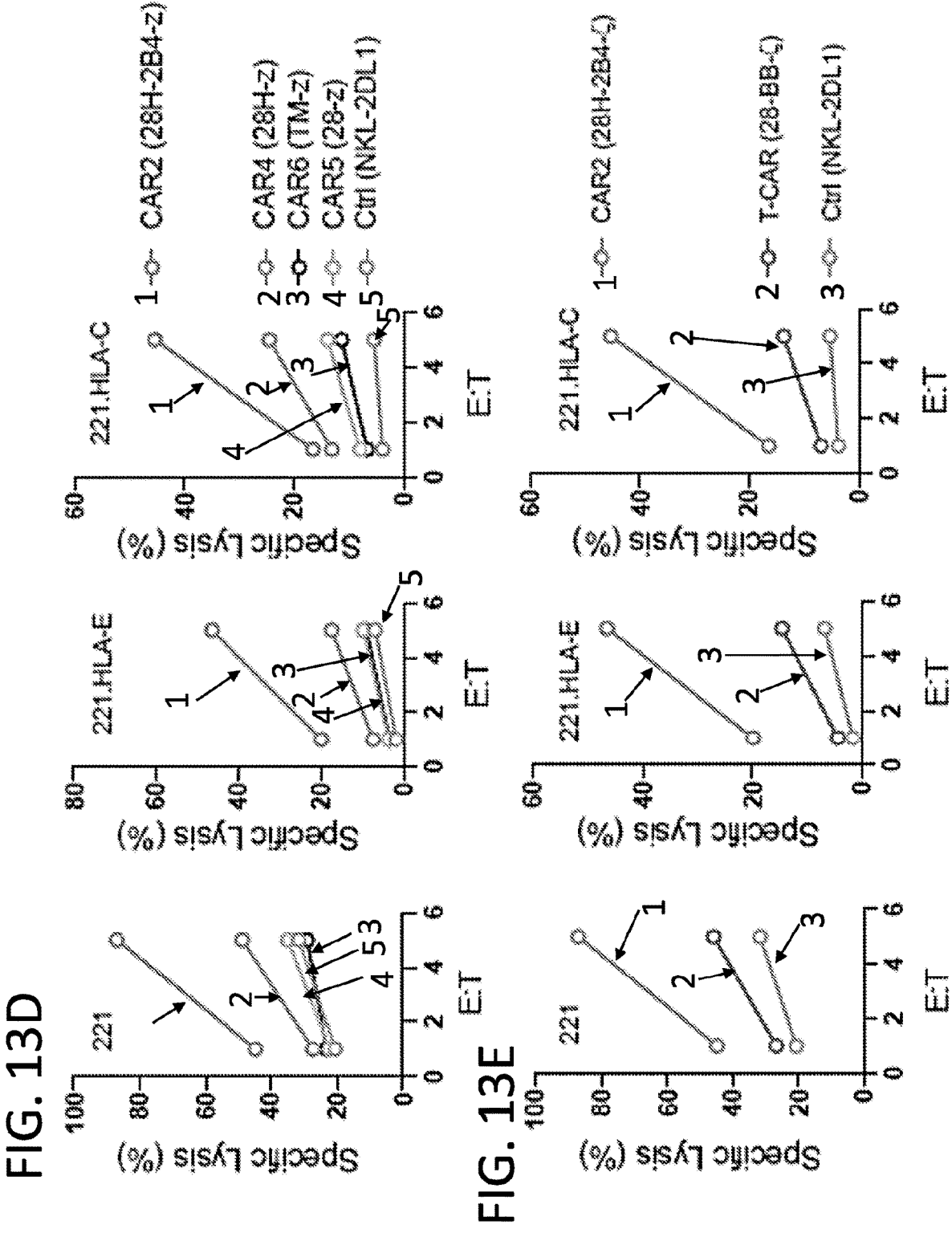
Figure 14:
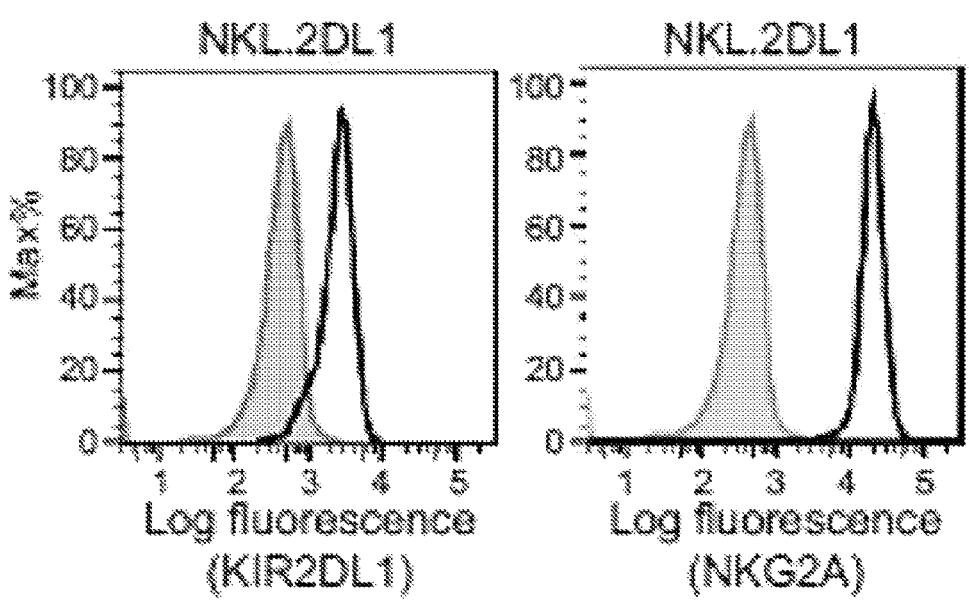
FIG. 14 is a pair of panels showing expression of KIR2DL1 (left) and NKG2A (right) on NKL.2DL1 cells. NKL.2DL1 cells were stained with IgG controls (shaded), and IgG antibodies to KIR2DL1 (left, open histogram) and NKG2A (right, open histogram).

We have demonstrated that CD28H is a strong NK cell co-activation receptor, and that a chimeric receptor containing the signaling domains of both CD28H and TCRζ is resistant to NKG2A-mediated inhibition (Zhuang et al., *Cancer Immunol. Res.* 7:939-951, 2019). Resting human NK cells are activated by synergistic combinations of NK activation receptors (Bryceson et al., *Blood* 107:159-166, 2006; Long et al., *Annu. Rev. Immunol.* 31:227-258, 2013). As one of the combinations, synergy between CD28H and 2B4 can induce robust NK-cell activation and degranulation (FIG. 13A). We hypothesized that combining the signaling domains of CD28H and 2B4 together with TCRζ cytoplasmic domain into a CAR construct can induce potent NK cell activation, which might achieve stronger resistance to inhibitory signals. We designed CAR constructs using anti-CD19 scFv with an N-terminal Myc-tag and a CD8α hinge as an extracellular domain for targeting CD19$^+$ cancer cells. The transmembrane domain was either from CD28 for the T-CARs, or from CD28H for the NK-tailored CARs. The intracellular domains were made of a combination of 1 to 3 signaling domains from NK receptors CD28H and 2B4, T-cell receptors CD28 and 4-1BB, and the ζ chain of the T cell receptor (TCRζ) (FIG. 13B). CAR constructs were transfected into NKL.2DL1 cells, which have endogenous expression of NKG2A and transgenic expression of KIR2DL1 (FIG. 14). Similar expression was achieved among different CAR constructs on NKL cells (FIG. 13C). Killing assays using the MHC-I-negative CD19$^+$ 721.221 lymphoblast cell line (referred to here as 221) as target cells demonstrated that CD19.CAR2 containing the combination of the CD28H, 2B4 and TCRζ signaling domains induced robust NK-cell cytotoxicity toward 221 lymphoblasts, and the signaling domains of both CD28H and 2B4 contributed to this strong activity (FIG. 13D). Compared to a third generation T-cell CAR (denoted as T-CAR), CD19.CAR2 (e.g., SEQ ID NO: 12) exhibited higher tumor-lysis efficacy toward 221 target cells (FIG. 13E).

Figure 15B:
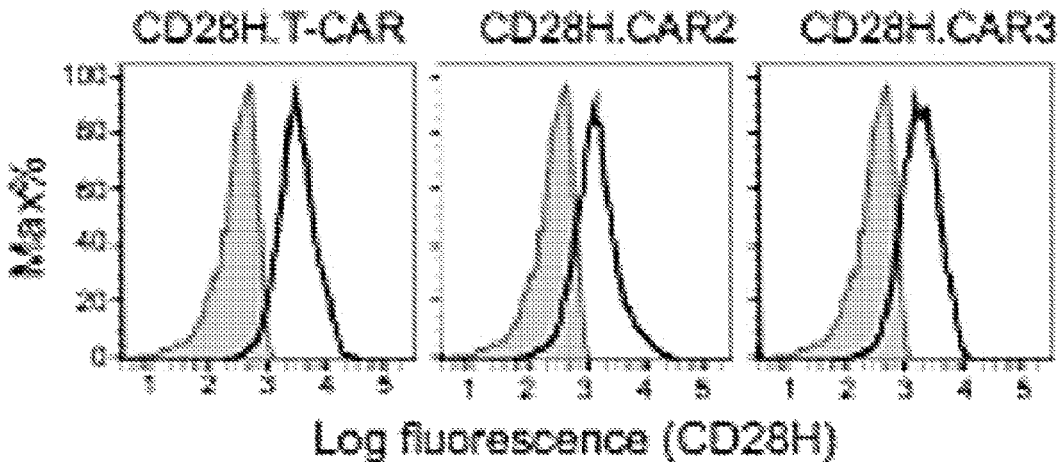
Figure 15C:
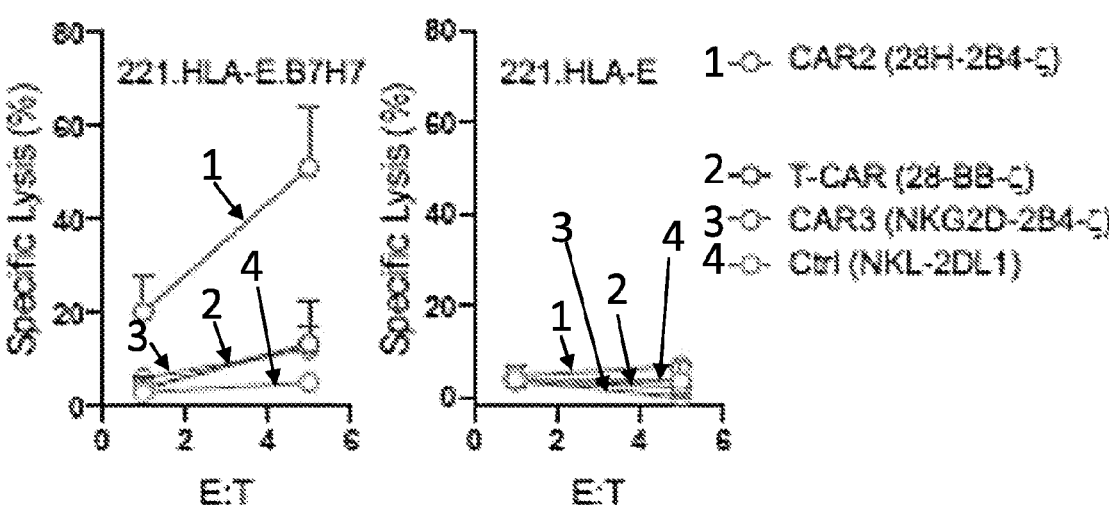
Figure 15D:
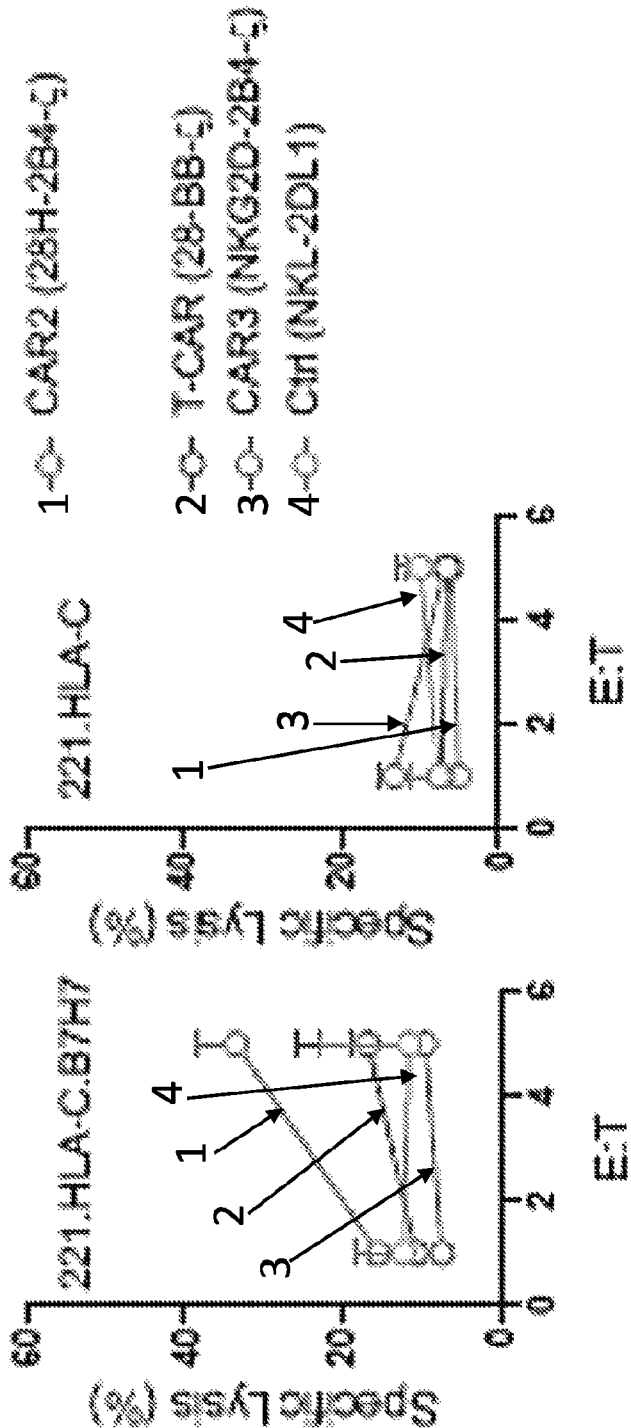

To test resistance of the CAR construct to inhibition mediated by receptors for MHC-I, 221 cells transfected with HLA-E or HLA-C were used for cytotoxicity assays. CD19.CAR2 could overcome inhibition mediated by NKG2A or KIR2DL1 and induced lysis of MHC-I$^+$ lymphoblast target cells, and both co-stimulatory domains were required for this inhibition-resistant response (FIG. 13D). By comparison to CD19.CAR2, the 3$^{rd}$ generation CD19.T-CAR (CD28-41BB-ζ) expressed in NKL.2DL1 cells was much weaker in its ability to overcome inhibition by NKG2A and KIR2DL1 (FIG. 13E). Besides the CAR constructs using CD19 scFv as the extracellular antigen-targeting domain, we also tested CARs using CD28H receptor itself as an extracellular domain for targeting B7H7$^+$ tumor cells (FIGS. 15A and 15B). Killing assays were carried out using B7H7 and MHC-I (HLA-E or HLA-C) transfected 221 lymphoblasts (Zhuang et al., *Cancer Immunol. Res.* 7:939-951, 2019). Compared to CD28H.T-CAR, the CD28H.CAR2 (e.g., SEQ ID NO: 2) induced NK cell activation that was much more resistant to inhibition by either NKG2A or KIR2DL1 (FIGS. 15C and 15D). Moreover, CD28H.CAR2 demonstrated superior inhibition-resistant activity than another NK-tailored CAR (CAR3), composed of the transmembrane domain of NKG2D, for recruitment of the signaling molecule DAP10, fused to the cytoplasmic domains of 2B4 and TCRζ (FIGS. 15C and 15D). This NKG2D-2B4-3 transmembrane and signaling domain composition (CAR3) was previously tested as part of a mesothelin-targeting CAR in iPSC-derived NK cells (Li et al., *Cell Stem Cell* 23:181-192 e5, 2018).

Figure 16A:
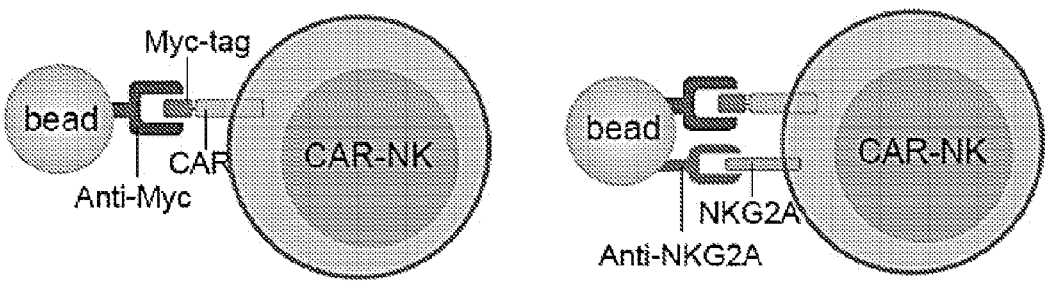
FIGS. 16A-16E illustrates that CD19.CAR2 overcomes NKG2A-mediated inhibition and transduces more persistent activation signals than T-CAR.
Figure 16B:
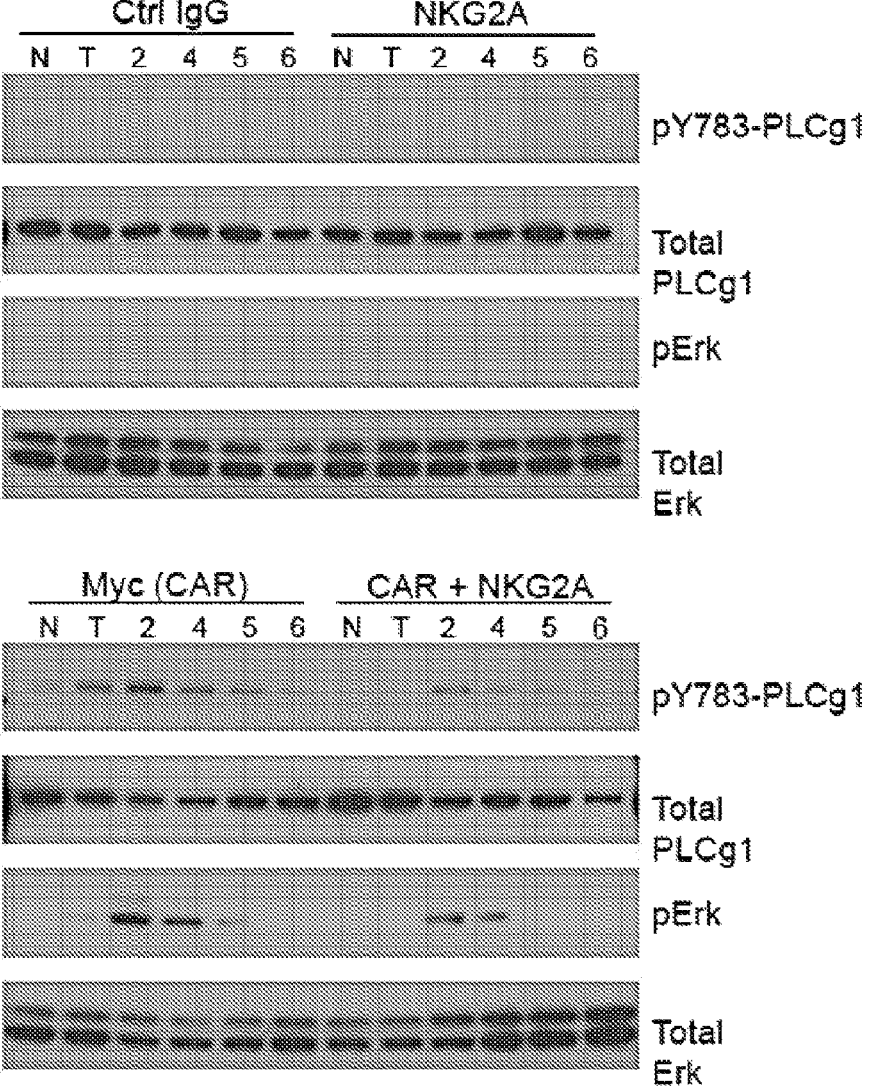
Figure 16D:
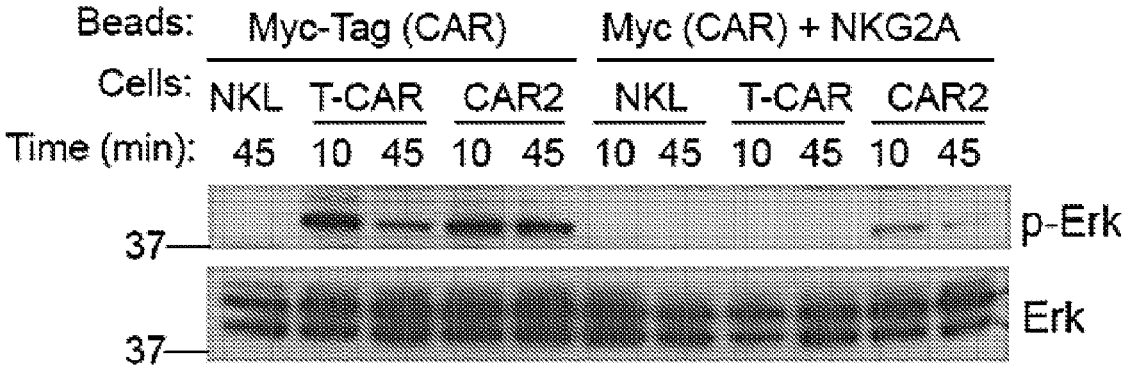
Figure 16E:
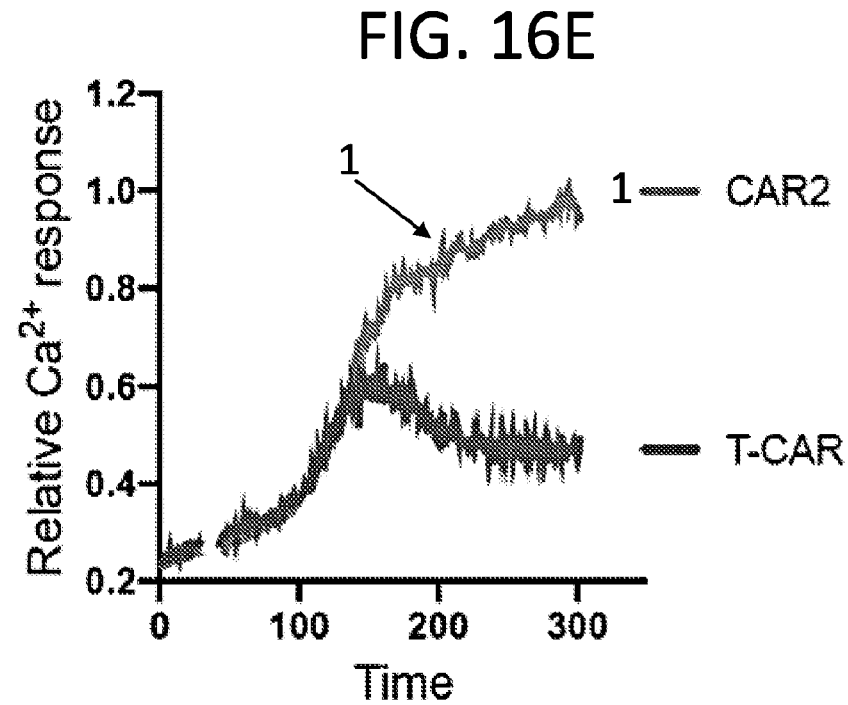

To examine activation signals transduced through CARs, NKL cells expressing CD19.CARs were stimulated by bead-coupled myc-tag antibody (Myc-beads), which induced activation signals through CARs by crosslinking N-terminal myc-tags (FIG. 16A). We evaluated phosphorylation of phospholipase Cγ1 (PLC-γ1) Tyr783 and the mitogen-associated protein kinase (MAPK/Erk) in lysates of NKL cells expressing CD19.CARs. Phosphorylation of PLC-γ1 and of ERK was detectable after stimulation through each CAR, except CAR6, which carries the cytoplasmic signaling domain of TCRζ only (FIG. 16B and FIG. 13B). Among all the tested CARs, CAR2 induced the strongest phosphorylation of both PLC-γ1 and Erk (FIGS. 16B and 16C and FIG. 15A). Stimulation with beads coupled with antibodies to either NKG2A or Myc-tag, or to both, was used to test the resistance to inhibition of different CARs (FIG. 16A). The strongest resistance to inhibition was detected after co-crosslinking NKG2A and CAR2. Substantial PLC-γ1 and Erk phosphorylation was also retained while NKG2A and CAR4 were crosslinked (FIGS. 16B and 16C). Compared to T-CAR, both CAR2 and CAR4 induced NK-cell activating signals that are more resistant to inhibition (FIGS. 16B and 16C). Moreover, sustained Erk phosphorylation was detected in CAR2-mediated NK-cell activation comparing to that of T-CAR, indicating more persistent activation signals were produced by CAR2 (FIG. 16D). This conclusion was further supported by calcium mobilization assays, which showed more sustained calcium mobilization after crosslinking of CAR2 than T-CAR (FIG. 16E).

Here we demonstrated that the NK-tailored CAR2 containing a fused signaling domain of CD28H-2B4-TCRζ was a more effective CAR construct for expression in NK cells than the third-generation T-CAR. CAR2 induced stronger cytotoxicity and activation signals than T-CAR. Importantly, CAR-2 triggered inhibition-resistant activation signals, which facilitated NK cells to overcome inhibition mediated by receptors for MHC class I and kill MHC class I$^+$ cancer cells. Although some transformed cancer cells down regulate MHC class I to escape T-cell-mediated surveillance, many tumor cells still retain substantial expression of MHC class I, which could engage NKG2A or inhibitory KIRs and limit anti-cancer responses of NK cells. These results support that, unlike cellular therapy with T cells, evaluation of inhibition-resistance property of CAR constructs for expression in NK cells is important. Design of CAR2 signaling domain was based on the strong synergy between activating receptors 2B4 and CD28H.

Example 3

In Vivo Evaluation of CAR Efficacy

This example describes methods that can be used to evaluate efficacy of one or more of the disclosed CARs in vivo in a mouse xenograft model. However, one skilled in the art will appreciate that methods that deviate from these specific methods can also be used to test efficacy of CARs in vivo.

NOD-scid IL2Rγ$^{null}$ mice (also known as NSG mice) are injected with $10^5$ to $10^6$ luciferase-expressing NALM-6 B-ALL cells. NK cells are isolated from the PBMCs of healthy donors by positive and/or negative selection using immune-magnetic methods. Expanded NK cells are transduced with a retroviral vector including a CD19-CAR, such as those described herein (e.g., SEQ ID NOs: 1, 5, 11, and 15). A composition comprising $10^6$ to $10^7$ of the transduced and expanded NK cells is administered to tumor-bearing mice intravenously. In vivo proliferation and persistence of CAR-expressing NK cells is supported by administration of human IL-2 or IL-15. Tumor burden is tracked by bioluminescent imaging (BLI). In vivo efficacy of CARs is evaluated by both tumor burden and overall survival (OS) of tumor-bearing NSG mice.

Example 4

Treating B-Cell Lymphoma with CD19-CAR Expressing NK Cells

This example describes methods that can be used to treat a subject with a B-cell lymphoma with CD19-CAR transduced NK cells. However, one skilled in the art will appreciate that methods that deviate from these specific methods can also be used to successfully treat a subject with B-cell lymphoma. In addition, similar methods can be used to treat a subject with other CAR-expressing NK cells and other cancers.

A subject with a B-cell lymphoma undergoes apheresis to collect peripheral blood mononuclear cells. NK cells (e.g., CD56-positive/CD3-negative cells) are isolated from the PBMCs by positive and/or negative selection using immune-magnetic methods. transduced with a retroviral vector including a CD19-CAR, such as those described herein (e.g., SEQ ID NOs: 1, 5, 11, 15, and 19). The transduced NK cells can be cryopreserved for later use or can be formulated for administration to the subject (for example, in a pharmaceutically acceptable carrier). A composition comprising $10^6$ to $10^{12}$ of the expanded NK cells is administered to the subject intravenously.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A chimeric antigen receptor comprising:
   (a) a target binding domain comprising a CD19 scFv or a CD28H extracellular domain;
   (b) a transmembrane domain comprising a CD28H transmembrane domain; and
   (c) an intracellular domain comprising a first intracellular signaling domain from CD28 homolog (CD28H) and a second intracellular signaling domain, wherein the first and second intracellular signaling domains can be in either order.

2. The chimeric antigen receptor of claim 1, wherein the CD28H intracellular signaling domain comprises an amino acid sequence with at least 90% identity to the amino acids 172-282 of SEQ ID NO: 2 or comprises the amino acid sequence of amino acids 172-282 of SEQ ID NO: 2.

3. The chimeric antigen receptor of claim 1, wherein the second intracellular signaling domain is from 2B4, TCRζ, FcεR1γ, or DAP12.

4. The chimeric antigen receptor of claim 1, wherein the second intracellular domain is from TCRζ and wherein the TCRζ intracellular signaling domain comprises an amino acid sequence with at least 90% identity to the amino acids 283-395 of SEQ ID NO: 2 or comprises the amino acid sequence of amino acids 283-395 of SEQ ID NO: 2.

5. The chimeric antigen receptor of claim 1, wherein the second intracellular signaling domain is from 2B4 and wherein the 2B4 intracellular signaling domain comprises an amino acid sequence with at least 90% identity to the amino acids 172-291 of SEQ ID NO: 10 or comprises the amino acid sequence of amino acids 172-291 of SEQ ID NO: 10.

6. The chimeric antigen receptor of claim 1, wherein the intracellular domain further comprises an intracellular region between the transmembrane domain and the first intracellular signaling domain.

7. The chimeric antigen receptor of claim 6, wherein the transmembrane domain and intracellular region are from CD16, NKp46, NKp30, NKp44, or KIR2DS4.

8. A chimeric antigen receptor comprising:
   (a) a target binding domain comprising a CD19 scFv or a CD28H extracellular domain;
   (b) a transmembrane domain comprising a CD28H transmembrane domain; and
   (c) an intracellular domain comprising a first intracellular signaling domain from CD28 homolog (CD28H), a second intracellular signaling domain from 2B4, and a third intracellular signaling domain, wherein the first, second, and third intracellular signaling domains can be in any order.

9. The chimeric antigen receptor of claim 8, wherein:
   the CD28H intracellular signaling domain comprises an amino acid sequence with at least 90% identity to the amino acids 172-282 of SEQ ID NO: 2 or comprises the amino acid sequence of amino acids 172-282 of SEQ ID NO: 2; and/or
   wherein the 2B4 intracellular signaling domain comprises an amino acid sequence with at least 90% identity to the amino acids 172-291 of SEQ ID NO: 10 or comprises the amino acid sequence of amino acids 172-291 of SEQ ID NO: 10.

10. The chimeric antigen receptor of claim 8, wherein the third intracellular signaling domain is from TCRζ, FcεR1γ, or DAP12.

11. The chimeric antigen receptor of claim 1, further comprising:
   a hinge domain, wherein the hinge domain is C-terminal to the target binding domain and N-terminal to the transmembrane domain; and/or
   an amino-terminal signal sequence.

12. The chimeric antigen receptor of claim 11, wherein the hinge region comprises a CD8α hinge region.

13. The chimeric antigen receptor of claim 11, wherein the signal sequence is a CD8α signal sequence.

14. The chimeric antigen receptor of claim 1, comprising an amino acid sequence with at least 90% sequence identity to the amino acid sequence of any one of SEQ ID NOs: 2, 6, 12, 16, and 20 or comprising the amino acid sequence of any one of SEQ ID NOs: 2, 6, 12, 16, and 20.

* * * * *

SEQUENCE LISTING

```
<160> NUMBER OF SEQ ID NOS: 25

<210> SEQ ID NO 1
<211> LENGTH: 1185
<212> TYPE: DNA
<213> ORGANISM: Artificial Sequence
<220> FEATURE:
<223> OTHER INFORMATION: CD28H(FL)-TCRzeta(CD)

<400> SEQUENCE: 1
atggggtccc cgggcatggt gctgggcctc ctggtgcaga tctgggccct gcaagaagcc      60
tcaagcctga gcgtgcagca ggggcccaac ttgctgcagg tgaggcaggg cagtcaggcg     120
accctggtct gccaggtgga ccaggccaca gcctgggaac ggctccgtgt taagtggaca     180
aaggatgggg ccatcctgtg tcaaccgtac atcaccaacg gcagcctcag cctggggggtc     240 tgcgggcccc agggacggct ctcctggcag gcacccagcc atctcaccct gcagctggac     300
cctgtgagcc tcaaccacag cggggcgtac gtgtgctggg cggccgtaga gattcctgag     360
ttggaggagg ctgagggcaa cataacaagg ctctttgtgg acccagatga ccccacacag     420
aacagaaacc ggatcgcaag cttcccagga ttcctcttcg tgctgctggg ggtgggaagc     480
atgggtgtgg ctgcgatcgt gtggggtgcc tggttctggg gccgccgcag ctgccagcaa     540
agggactcag gtaacagccc aggaaatgca ttctacagca acgtcctata ccggccccgg     600
ggggccccaa agaagagtga ggactgctct ggagagggga aggaccagag gggccagagc     660
atttattcaa cctccttccc gcaaccggcc ccccgccagc cgcacctggc gtcaagaccc     720
```

```
tgccccagcc cgagaccctg ccccagcccc aggcccggcc accccgtctc tatggtcagg    780
gtctctccta gaccaagccc cacccagcag ccgaggccaa aagggttccc caaagtggga    840
gaggagagag tgaagttcag caggagcgca gacgccccg cgtaccagca gggccagaac     900
cagctctata acgagctcaa tctaggacga agagaggagt acgatgtttt ggacaagaga    960
cgtggccggg accctgagat ggggggaaag ccgcagagaa ggaagaaccc tcaggaaggc    1020
ctgtacaatg aactgcagaa agataagatg gcggaggcct acagtgagat tgggatgaaa    1080
ggcgagcgcc ggagggggcaa ggggcacgat ggcctttacc agggtctcag tacagccacc   1140
aaggacacct acgacgccct tcacatgcag gccctgcccc ctcgc                    1185
```

```
<210> SEQ ID NO 2
<211> LENGTH: 395
<212> TYPE: PRT
<213> ORGANISM: Artificial Sequence
<220> FEATURE:
<223> OTHER INFORMATION: CD28H(FL)-TCRzeta(CD)

<400> SEQUENCE: 2

Met Gly Ser Pro Gly Met Val Leu Gly Leu Leu Val Gln Ile Trp Ala
1               5                   10                  15

Leu Gln Glu Ala Ser Ser Leu Ser Val Gln Gln Gly Pro Asn Leu Leu
                20                  25                  30

Gln Val Arg Gln Gly Ser Gln Ala Thr Leu Val Cys Gln Val Asp Gln
            35                  40                  45

Ala Thr Ala Trp Glu Arg Leu Arg Val Lys Trp Thr Lys Asp Gly Ala
        50                  55                  60

Ile Leu Cys Gln Pro Tyr Ile Thr Asn Gly Ser Leu Ser Leu Gly Val
65                  70                  75                  80

Cys Gly Pro Gln Gly Arg Leu Ser Trp Gln Ala Pro Ser His Leu Thr
                85                  90                  95

Leu Gln Leu Asp Pro Val Ser Leu Asn His Ser Gly Ala Tyr Val Cys
            100                 105                 110

Trp Ala Ala Val Glu Ile Pro Glu Leu Glu Glu Ala Glu Gly Asn Ile
            115                 120                 125

Thr Arg Leu Phe Val Asp Pro Asp Asp Pro Thr Gln Asn Arg Asn Arg
        130                 135                 140

Ile Ala Ser Phe Pro Gly Phe Leu Phe Val Leu Leu Gly Val Gly Ser
145                 150                 155                 160

Met Gly Val Ala Ala Ile Val Trp Gly Ala Trp Phe Trp Gly Arg Arg
                165                 170                 175

Ser Cys Gln Gln Arg Asp Ser Gly Asn Ser Pro Gly Asn Ala Phe Tyr
                180                 185                 190

Ser Asn Val Leu Tyr Arg Pro Arg Gly Ala Pro Lys Lys Ser Glu Asp
                195                 200                 205

Cys Ser Gly Glu Gly Lys Asp Gln Arg Gly Gln Ser Ile Tyr Ser Thr
            210                 215                 220

Ser Phe Pro Gln Pro Ala Pro Arg Gln Pro His Leu Ala Ser Arg Pro
225                 230                 235                 240

Cys Pro Ser Pro Arg Pro Cys Pro Ser Pro Arg Pro Gly His Pro Val
                245                 250                 255

Ser Met Val Arg Val Ser Pro Arg Pro Ser Pro Thr Gln Gln Pro Arg
                260                 265                 270

Pro Lys Gly Phe Pro Lys Val Gly Glu Glu Arg Val Lys Phe Ser Arg
```

```
               275                 280                 285

Ser Ala Asp Ala Pro Ala Tyr Gln Gln Gly Gln Asn Gln Leu Tyr Asn
    290                 295                 300

Glu Leu Asn Leu Gly Arg Arg Glu Glu Tyr Asp Val Leu Asp Lys Arg
305                 310                 315                 320

Arg Gly Arg Asp Pro Glu Met Gly Gly Lys Pro Gln Arg Arg Lys Asn
                325                 330                 335

Pro Gln Glu Gly Leu Tyr Asn Glu Leu Gln Lys Asp Lys Met Ala Glu
            340                 345                 350

Ala Tyr Ser Glu Ile Gly Met Lys Gly Glu Arg Arg Arg Gly Lys Gly
        355                 360                 365

His Asp Gly Leu Tyr Gln Gly Leu Ser Thr Ala Thr Lys Asp Thr Tyr
    370                 375                 380

Asp Ala Leu His Met Gln Ala Leu Pro Pro Arg
385                 390                 395
```

```
<210> SEQ ID NO 3
<211> LENGTH: 852
<212> TYPE: DNA
<213> ORGANISM: Artificial Sequence
<220> FEATURE:
<223> OTHER INFORMATION: CD28H(EC-TM)-TCRzeta(CD)

<400> SEQUENCE: 3
atggggtccc cgggcatggt gctgggcctc ctggtgcaga tctgggccct gcaagaagcc      60
tcaagcctga gcgtgcagca ggggcccaac ttgctgcagg tgaggcaggg cagtcaggcg     120
accctggtct gccaggtgga ccaggccaca gcctgggaac ggctccgtgt taagtggaca     180
aaggatgggg ccatcctgtg tcaaccgtac atcaccaacg gcagcctcag cctgggggtc     240
tgcgggcccc agggacggct ctcctggcag gcacccagcc atctcaccct gcagctggac     300
cctgtgagcc tcaaccacag cggggcgtac gtgtgctggg cggccgtaga gattcctgag     360
ttggaggagg ctgagggcaa cataacaagg ctctttgtgg acccagatga ccccacacag     420
aacagaaacc ggatcgcaag cttcccagga ttcctcttcg tgctgctggg ggtgggaagc     480
atgggtgtgg ctgcgatcgt gtggggtgcc tggagagtga agttcagcag gagcgcagac     540
gcccccgcgt accagcaggg ccagaaccag ctctataacg agctcaatct aggacgaaga     600
gaggagtacg atgttttgga caagagacgt ggccgggacc ctgagatggg gggaaagccg     660
cagagaagga agaaccctca ggaaggcctg tacaatgaac tgcagaaaga taagatggcg     720
gaggcctaca gtgagattgg gatgaaaggc gagcgccgga ggggcaaggg gcacgatggc     780
ctttaccagg gtctcagtac agccaccaag gacacctacg acgcccttca catgcaggcc     840
ctgccccctc gc                                                          852
```

```
<210> SEQ ID NO 4
<211> LENGTH: 284
<212> TYPE: PRT
<213> ORGANISM: Artificial Sequence
<220> FEATURE:
<223> OTHER INFORMATION: CD28H(EC-TM)-TCRzeta(CD)

<400> SEQUENCE: 4

Met Gly Ser Pro Gly Met Val Leu Gly Leu Leu Val Gln Ile Trp Ala
1               5                   10                  15

Leu Gln Glu Ala Ser Ser Leu Ser Val Gln Gln Gly Pro Asn Leu Leu
            20                  25                  30
```

```
Gln Val Arg Gln Gly Ser Gln Ala Thr Leu Val Cys Gln Val Asp Gln
        35                  40                  45

Ala Thr Ala Trp Glu Arg Leu Arg Val Lys Trp Thr Lys Asp Gly Ala
    50                  55                  60

Ile Leu Cys Gln Pro Tyr Ile Thr Asn Gly Ser Leu Ser Leu Gly Val
65                  70                  75                  80

Cys Gly Pro Gln Gly Arg Leu Ser Trp Gln Ala Pro Ser His Leu Thr
                85                  90                  95

Leu Gln Leu Asp Pro Val Ser Leu Asn His Ser Gly Ala Tyr Val Cys
            100                 105                 110

Trp Ala Ala Val Glu Ile Pro Glu Leu Glu Glu Ala Glu Gly Asn Ile
        115                 120                 125

Thr Arg Leu Phe Val Asp Pro Asp Asp Pro Thr Gln Asn Arg Asn Arg
    130                 135                 140

Ile Ala Ser Phe Pro Gly Phe Leu Phe Val Leu Leu Gly Val Gly Ser
145                 150                 155                 160

Met Gly Val Ala Ala Ile Val Trp Gly Ala Trp Arg Val Lys Phe Ser
                165                 170                 175

Arg Ser Ala Asp Ala Pro Ala Tyr Gln Gln Gly Gln Asn Gln Leu Tyr
            180                 185                 190

Asn Glu Leu Asn Leu Gly Arg Arg Glu Glu Tyr Asp Val Leu Asp Lys
            195                 200                 205

Arg Arg Gly Arg Asp Pro Glu Met Gly Gly Lys Pro Gln Arg Arg Lys
    210                 215                 220

Asn Pro Gln Glu Gly Leu Tyr Asn Glu Leu Gln Lys Asp Lys Met Ala
225                 230                 235                 240

Glu Ala Tyr Ser Glu Ile Gly Met Lys Gly Glu Arg Arg Arg Gly Lys
                245                 250                 255

Gly His Asp Gly Leu Tyr Gln Gly Leu Ser Thr Ala Thr Lys Asp Thr
            260                 265                 270

Tyr Asp Ala Leu His Met Gln Ala Leu Pro Pro Arg
            275                 280
```

```
<210> SEQ ID NO 5
<211> LENGTH: 1545
<212> TYPE: DNA
<213> ORGANISM: Artificial Sequence
<220> FEATURE:
<223> OTHER INFORMATION: CD28H.CAR2

<400> SEQUENCE: 5 atgggggtccc cgggcatggt gctgggcctc ctggtgcaga tctgggccct gcaagaagcc      60
tcaagcctga gcgtgcagca ggggcccaac ttgctgcagg tgaggcaggg cagtcaggcg     120
accctggtct gccaggtgga ccaggccaca gcctgggaac ggctccgtgt taagtggaca     180
aaggatgggg ccatcctgtg tcaaccgtac atcaccaacg gcagcctcag cctggggggtc     240 tgcgggcccc agggacggct ctcctggcag gcacccagcc atctcaccct gcagctggac     300
cctgtgagcc tcaaccacag cggggcgtac gtgtgctggg cggccgtaga gattcctgag     360
ttggaggagg ctgagggcaa cataacaagg ctctttgtgg acccagatga ccccacacag     420
aacagaaacc ggatcgcaag cttcccagga ttcctcttcg tgctgctggg ggtgggaagc     480
atgggtgtgg ctgcgatcgt gtggggtgcc tggttctggg ccgccgcag ctgccagcaa     540 agggactcag gtaacagccc aggaaatgca ttctacagca acgtcctata ccggcccccgg     600 ggggccccaa agaagagtga ggactgctct ggagaggggga aggaccagag gggccagagc     660
```

```
atttattcaa ccagtttccc tcaaccggct ccaagacaac cacatctcgc cagtcggcct   720
tgtccgtccc ctagaccctg ccccagtccc aggcccggcc accccgtctc tatggtcagg   780
gtctctccta gaccaagccc cacccagcag ccgaggccaa aagggttccc caaagtggga   840
gaggagtgga ggagaaagag gaaggagaag cagtcagaga ccagtcccaa ggaattttg    900 acaatttacg aagatgtcaa ggatctgaaa accaggagaa atcacgagca ggagcagact   960
tttcctggag ggggagcac catctactct atgatccagt cccagtcttc tgctcccacg   1020
tcacaagaac ctgcatatac attatattca ttaattcagc cttccaggaa gtctggatcc   1080
aggaagagga accacagccc ttccttcaat agcactatct atgaagtgat tggaaagagt   1140
caacctaaag cccagaaccc tgctcgattg agccgcaaag agctggagaa ctttgatgtt   1200
tattccagtg tgaagttcag caggagcgca gacgcccccg cgtaccagca gggccagaac   1260
cagctctata cgagctcaa tctaggacga agagaggagt acgatgtttt ggacaagaga   1320
cgtggccggg accctgagat gggggaaag ccgcagagaa ggaagaaccc tcaggaaggc    1380
ctgtacaatg aactgcagaa agataagatg gcggaggcct acagtgagat tgggatgaaa   1440
ggcgagcgcc ggagggcaa ggggcacgat ggcctttacc agggtctcag tacagccacc    1500
aaggacacct acgacgccct tcacatgcag gccctgcccc ctcgc               1545
```

```
<210> SEQ ID NO 6
<211> LENGTH: 515
<212> TYPE: PRT
<213> ORGANISM: Artificial Sequence
<220> FEATURE:
<223> OTHER INFORMATION: CD28H.CAR2

<400> SEQUENCE: 6

Met Gly Ser Pro Gly Met Val Leu Gly Leu Leu Val Gln Ile Trp Ala
1               5                   10                  15

Leu Gln Glu Ala Ser Ser Leu Ser Val Gln Gln Gly Pro Asn Leu Leu
            20                  25                  30

Gln Val Arg Gln Gly Ser Gln Ala Thr Leu Val Cys Gln Val Asp Gln
        35                  40                  45

Ala Thr Ala Trp Glu Arg Leu Arg Val Lys Trp Thr Lys Asp Gly Ala
    50                  55                  60

Ile Leu Cys Gln Pro Tyr Ile Thr Asn Gly Ser Leu Ser Leu Gly Val
65                  70                  75                  80

Cys Gly Pro Gln Gly Arg Leu Ser Trp Gln Ala Pro Ser His Leu Thr
                85                  90                  95

Leu Gln Leu Asp Pro Val Ser Leu Asn His Ser Gly Ala Tyr Val Cys
            100                 105                 110

Trp Ala Ala Val Glu Ile Pro Glu Leu Glu Glu Ala Glu Gly Asn Ile
        115                 120                 125

Thr Arg Leu Phe Val Asp Pro Asp Asp Pro Thr Gln Asn Arg Asn Arg
    130                 135                 140

Ile Ala Ser Phe Pro Gly Phe Leu Phe Val Leu Leu Gly Val Gly Ser
145                 150                 155                 160

Met Gly Val Ala Ala Ile Val Trp Gly Ala Trp Phe Trp Gly Arg Arg
                165                 170                 175

Ser Cys Gln Gln Arg Asp Ser Gly Asn Ser Pro Gly Asn Ala Phe Tyr
            180                 185                 190

Ser Asn Val Leu Tyr Arg Pro Arg Gly Ala Pro Lys Lys Ser Glu Asp
        195                 200                 205
```

```
Cys Ser Gly Glu Gly Lys Asp Gln Arg Gly Gln Ser Ile Tyr Ser Thr
    210                 215                 220

Ser Phe Pro Gln Pro Ala Pro Arg Gln Pro His Leu Ala Ser Arg Pro
225                 230                 235                 240

Cys Pro Ser Pro Arg Pro Cys Pro Ser Pro Arg Pro Gly His Pro Val
                245                 250                 255

Ser Met Val Arg Val Ser Pro Arg Pro Ser Pro Thr Gln Gln Pro Arg
                260                 265                 270

Pro Lys Gly Phe Pro Lys Val Gly Glu Glu Trp Arg Arg Lys Arg Lys
                275                 280                 285

Glu Lys Gln Ser Glu Thr Ser Pro Lys Glu Phe Leu Thr Ile Tyr Glu
    290                 295                 300

Asp Val Lys Asp Leu Lys Thr Arg Arg Asn His Glu Gln Glu Gln Thr
305                 310                 315                 320

Phe Pro Gly Gly Gly Ser Thr Ile Tyr Ser Met Ile Gln Ser Gln Ser
                325                 330                 335

Ser Ala Pro Thr Ser Gln Glu Pro Ala Tyr Thr Leu Tyr Ser Leu Ile
                340                 345                 350

Gln Pro Ser Arg Lys Ser Gly Ser Arg Lys Arg Asn His Ser Pro Ser
                355                 360                 365

Phe Asn Ser Thr Ile Tyr Glu Val Ile Gly Lys Ser Gln Pro Lys Ala
    370                 375                 380

Gln Asn Pro Ala Arg Leu Ser Arg Lys Glu Leu Glu Asn Phe Asp Val
385                 390                 395                 400

Tyr Ser Arg Val Lys Phe Ser Arg Ser Ala Asp Ala Pro Ala Tyr Gln
                405                 410                 415

Gln Gly Gln Asn Gln Leu Tyr Asn Glu Leu Asn Leu Gly Arg Arg Glu
                420                 425                 430

Glu Tyr Asp Val Leu Asp Lys Arg Arg Gly Arg Asp Pro Glu Met Gly
                435                 440                 445

Gly Lys Pro Gln Arg Arg Lys Asn Pro Gln Glu Gly Leu Tyr Asn Glu
    450                 455                 460

Leu Gln Lys Asp Lys Met Ala Glu Ala Tyr Ser Glu Ile Gly Met Lys
465                 470                 475                 480

Gly Glu Arg Arg Arg Gly Lys Gly His Asp Gly Leu Tyr Gln Gly Leu
                485                 490                 495

Ser Thr Ala Thr Lys Asp Thr Tyr Asp Ala Leu His Met Gln Ala Leu
                500                 505                 510

Pro Pro Arg
        515
```

```
<210> SEQ ID NO 7
<211> LENGTH: 1119
<212> TYPE: DNA
<213> ORGANISM: Artificial Sequence
<220> FEATURE:
<223> OTHER INFORMATION: CD28H.T-CAR

<400> SEQUENCE: 7
atggggtccc cgggcatggt gctgggcctc ctggtgcaga tctgggccct gcaagaagcc        60
tcaagcctga gcgtgcagca ggggcccaac ttgctgcagg tgaggcaggg cagtcaggcg       120
accctggtct gccaggtgga ccaggccaca gcctgggaac ggctccgtgt taagtggaca       180
aaggatgggg ccatcctgtg tcaaccgtac atcaccaacg gcagcctcag cctgggggtc       240
```

-continued

```
tgcgggcccc aggacggct ctcctggcag gcacccagcc atctcaccct gcagctggac    300
cctgtgagcc tcaaccacag cggggcgtac gtgtgctggg cggccgtaga gattcctgag    360
ttggaggagg ctgagggcaa cataacaagg ctctttgtgg acccagatga ccccacacag    420
aacagaaacc ggatcgcaag cttcccagga ttttgggtgc tggtggtggt tggtggagtc    480
ctggcttgct atagcttgct agtaacagtg gcctttatta ttttctgggt gaggagtaag    540
aggagcaggc tcctgcacag tgactacatg aacatgactc cccgccgccc cgggcccacc    600
cgcaagcatt accagcccta tgccccacca cgcgacttcg cagcctatcg ctccaaacgg    660
ggcagaaaga aactcctgta tatattcaaa caaccattta tgagaccagt acaaactact    720
caagaggaag atggctgtag ctgccgattt ccagaagaag aagaaggagg atgtgaactg    780
agagtgaagt tcagcaggag cgcagacgcc cccgcgtacc agcagggcca gaaccagctc    840
tataacgagc tcaatctagg acgaagagag gagtacgatg ttttggacaa gagacgtggc    900
cgggaccctg agatggggggg aaagccgcag agaaggaaga accctcagga aggcctgtac    960
aatgaactgc agaaagataa gatggcggag gcctacagtg agattgggat gaaaggcgag   1020
cgccggaggg gcaagggggca cgatggcctt taccagggtc tcagtacagc caccaaggac   1080
acctacgacg cccttcacat gcaggccctg cccctcgc                           1119
```

<210> SEQ ID NO 8
<211> LENGTH: 373
<212> TYPE: PRT
<213> ORGANISM: Artificial Sequence
<220> FEATURE:
<223> OTHER INFORMATION: CD28H.T-CAR

<400> SEQUENCE: 8

```
Met Gly Ser Pro Gly Met Val Leu Gly Leu Leu Val Gln Ile Trp Ala
1               5                   10                  15

Leu Gln Glu Ala Ser Ser Leu Ser Val Gln Gln Gly Pro Asn Leu Leu
            20                  25                  30

Gln Val Arg Gln Gly Ser Gln Ala Thr Leu Val Cys Gln Val Asp Gln
        35                  40                  45

Ala Thr Ala Trp Glu Arg Leu Arg Val Lys Trp Thr Lys Asp Gly Ala
    50                  55                  60

Ile Leu Cys Gln Pro Tyr Ile Thr Asn Gly Ser Leu Ser Leu Gly Val
65                  70                  75                  80

Cys Gly Pro Gln Gly Arg Leu Ser Trp Gln Ala Pro Ser His Leu Thr
                85                  90                  95

Leu Gln Leu Asp Pro Val Ser Leu Asn His Ser Gly Ala Tyr Val Cys
            100                 105                 110

Trp Ala Ala Val Glu Ile Pro Glu Leu Glu Glu Ala Glu Gly Asn Ile
        115                 120                 125

Thr Arg Leu Phe Val Asp Pro Asp Asp Pro Thr Gln Asn Arg Asn Arg
    130                 135                 140

Ile Ala Ser Phe Pro Gly Phe Trp Val Leu Val Val Val Gly Gly Val
145                 150                 155                 160

Leu Ala Cys Tyr Ser Leu Leu Val Thr Val Ala Phe Ile Ile Phe Trp
                165                 170                 175

Val Arg Ser Lys Arg Ser Arg Leu Leu His Ser Asp Tyr Met Asn Met
            180                 185                 190

Thr Pro Arg Arg Pro Gly Pro Thr Arg Lys His Tyr Gln Pro Tyr Ala
        195                 200                 205
```

```
Pro Pro Arg Asp Phe Ala Ala Tyr Arg Ser Lys Arg Gly Arg Lys Lys
    210                 215                 220

Leu Leu Tyr Ile Phe Lys Gln Pro Phe Met Arg Pro Val Gln Thr Thr
225                 230                 235                 240

Gln Glu Glu Asp Gly Cys Ser Cys Arg Phe Pro Glu Glu Glu Glu Gly
                245                 250                 255

Gly Cys Glu Leu Arg Val Lys Phe Ser Arg Ser Ala Asp Ala Pro Ala
                260                 265                 270

Tyr Gln Gln Gly Gln Asn Gln Leu Tyr Asn Glu Leu Asn Leu Gly Arg
                275                 280                 285

Arg Glu Glu Tyr Asp Val Leu Asp Lys Arg Arg Gly Arg Asp Pro Glu
    290                 295                 300

Met Gly Gly Lys Pro Gln Arg Arg Lys Asn Pro Gln Glu Gly Leu Tyr
305                 310                 315                 320

Asn Glu Leu Gln Lys Asp Lys Met Ala Glu Ala Tyr Ser Glu Ile Gly
                325                 330                 335

Met Lys Gly Glu Arg Arg Arg Gly Lys Gly His Asp Gly Leu Tyr Gln
                340                 345                 350

Gly Leu Ser Thr Ala Thr Lys Asp Thr Tyr Asp Ala Leu His Met Gln
                355                 360                 365

Ala Leu Pro Pro Arg
    370
```

<210> SEQ ID NO 9
<211> LENGTH: 1212
<212> TYPE: DNA
<213> ORGANISM: Artificial Sequence
<220> FEATURE:
<223> OTHER INFORMATION: CD28H.CAR3

<400> SEQUENCE: 9

```
atggggtccc cgggcatggt gctgggcctc ctggtgcaga tctgggccct gcaagaagcc      60
tcaagcctga gcgtgcagca ggggcccaac ttgctgcagg tgaggcaggg cagtcaggcg     120
accctggtct gccaggtgga ccaggccaca gcctgggaac ggctccgtgt taagtggaca     180
aaggatgggg ccatcctgtg tcaaccgtac atcaccaacg gcagcctcag cctgggggtc     240
tgcgggcccc agggacggct ctcctggcag gcacccagcc atctcaccct gcagctggac     300
cctgtgagcc tcaaccacag cggggcgtac gtgtgctggg cggccgtaga gattcctgag     360
ttggaggagg ctgagggcaa cataacaagg ctctttgtgg acccagatga ccccacacag     420
aacagaaacc ggatcgcaag cttcccagga ccattttttt tctgctgctt catcgctgta     480
gccatgggaa tccgtttcat tattatggta acatggagga gaaagaggaa ggagaagcag     540
tcagagacca gtcccaagga attttgaca atttacgaag atgtcaagga tctgaaaacc     600
aggagaaatc acgagcagga gcagactttt cctggagggg ggagcaccat ctactctatg     660
atccagtccc agtcttctgc tcccacgtca caagaacctg catatacatt atattcatta     720
attcagcctt ccaggaagtc tggatccagg aagaggaacc acagcccttc cttcaatagc     780
actatctatg aagtgattgg aaagagtcaa cctaaagccc agaaccctgc tcgattgagc     840
cgcaaagagc tggagaactt tgatgtttat tccagagtga agttcagcag gagcgcagac     900 gccccgcgt accagcaggg ccagaaccag ctctataacg agctcaatct aggacgaaga     960
gaggagtacg atgttttgga caagagacgt ggccgggacc ctgagatggg gggaaagccg    1020
cagagaagga agaaccctca ggaaggcctg tacaatgaac tgcagaaaga taagatggcg    1080
```

```
gaggcctaca gtgagattgg gatgaaaggc gagcgccgga ggggcaaggg gcacgatggc      1140
ctttaccagg gtctcagtac agccaccaag gacacctacg acgcccttca catgcaggcc      1200
ctgccccctc gc                                                          1212

<210> SEQ ID NO 10
<211> LENGTH: 404
<212> TYPE: PRT
<213> ORGANISM: Artificial Sequence
<220> FEATURE:
<223> OTHER INFORMATION: CD28H.CAR3

<400> SEQUENCE: 10

Met Gly Ser Pro Gly Met Val Leu Gly Leu Leu Val Gln Ile Trp Ala
1               5                   10                  15

Leu Gln Glu Ala Ser Ser Leu Ser Val Gln Gln Gly Pro Asn Leu Leu
                20                  25                  30

Gln Val Arg Gln Gly Ser Gln Ala Thr Leu Val Cys Gln Val Asp Gln
            35                  40                  45

Ala Thr Ala Trp Glu Arg Leu Arg Val Lys Trp Thr Lys Asp Gly Ala
        50                  55                  60

Ile Leu Cys Gln Pro Tyr Ile Thr Asn Gly Ser Leu Ser Leu Gly Val
65                  70                  75                  80

Cys Gly Pro Gln Gly Arg Leu Ser Trp Gln Ala Pro Ser His Leu Thr
                85                  90                  95

Leu Gln Leu Asp Pro Val Ser Leu Asn His Ser Gly Ala Tyr Val Cys
                100                 105                 110

Trp Ala Ala Val Glu Ile Pro Glu Leu Glu Glu Ala Glu Gly Asn Ile
            115                 120                 125

Thr Arg Leu Phe Val Asp Pro Asp Asp Pro Thr Gln Asn Arg Asn Arg
        130                 135                 140

Ile Ala Ser Phe Pro Gly Pro Phe Phe Phe Cys Cys Phe Ile Ala Val
145                 150                 155                 160

Ala Met Gly Ile Arg Phe Ile Ile Met Val Thr Trp Arg Arg Lys Arg
                165                 170                 175

Lys Glu Lys Gln Ser Glu Thr Ser Pro Lys Glu Phe Leu Thr Ile Tyr
            180                 185                 190

Glu Asp Val Lys Asp Leu Lys Thr Arg Arg Asn His Glu Gln Glu Gln
            195                 200                 205

Thr Phe Pro Gly Gly Gly Ser Thr Ile Tyr Ser Met Ile Gln Ser Gln
        210                 215                 220

Ser Ser Ala Pro Thr Ser Gln Glu Pro Ala Tyr Thr Leu Tyr Ser Leu
225                 230                 235                 240

Ile Gln Pro Ser Arg Lys Ser Gly Ser Arg Lys Arg Asn His Ser Pro
                245                 250                 255

Ser Phe Asn Ser Thr Ile Tyr Glu Val Ile Gly Lys Ser Gln Pro Lys
                260                 265                 270

Ala Gln Asn Pro Ala Arg Leu Ser Arg Lys Glu Leu Glu Asn Phe Asp
            275                 280                 285

Val Tyr Ser Arg Val Lys Phe Ser Arg Ser Ala Asp Ala Pro Ala Tyr
        290                 295                 300

Gln Gln Gly Gln Asn Gln Leu Tyr Asn Glu Leu Asn Leu Gly Arg Arg
305                 310                 315                 320

Glu Glu Tyr Asp Val Leu Asp Lys Arg Arg Gly Arg Asp Pro Glu Met
                325                 330                 335
```

```
Gly Gly Lys Pro Gln Arg Arg Lys Asn Pro Gln Glu Gly Leu Tyr Asn
            340                 345             350

Glu Leu Gln Lys Asp Lys Met Ala Glu Ala Tyr Ser Glu Ile Gly Met
        355                 360                 365

Lys Gly Glu Arg Arg Arg Gly Lys Gly His Asp Gly Leu Tyr Gln Gly
    370                 375                 380

Leu Ser Thr Ala Thr Lys Asp Thr Tyr Asp Ala Leu His Met Gln Ala
385                 390                 395                 400

Leu Pro Pro Arg
```

```
<210> SEQ ID NO 11
<211> LENGTH: 2049
<212> TYPE: DNA
<213> ORGANISM: Artificial Sequence
<220> FEATURE:
<223> OTHER INFORMATION: CD19.CAR2

<400> SEQUENCE: 11
atggcgctcc ctgtcaccgc actgcttctt ccgctggcac tgctgctgca cgctgcacgg      60
cctgagcaaa aacttatctc tgaagaggac ctcgatatac agatgacgca gacaacgtca     120
agtctttccg ccagcttggg agaccgagtg actatatctt gtagagcaag ccaggatatt     180
tctaagtatc ttaactggta ccaacaaaag cccgatggaa cggttaagct gcttatatac     240
cataccagta gactccactc cggcgtacca tcacggtttt ctggcagtgg ctccgggacc     300
gactattctt tgacgatctc taatctcgaa caagaggata ttgcaacata cttttgtcag     360
caaggcaata ccttgccata cgtttgggg gcgggacaa aacttgagat aaccggcggc       420
ggtggttcag gcggtggcgg ttccggtggt gggggatcag aggttaagct tcaggaatcc     480
ggaccaggtt tggttgcccc cagccaatct ctcagcgtta catgcacggt ttcaggcgtc     540
agtctccccg attacggtgt aagttggatt cggcaacctc cgcgaaaggg tctggaatgg     600
ctgggggtta tttgggggag tgagacaact tattacaact ctgcacttaa gagtcggctt     660
accatcatca ggataattc aaaatcacaa gtattcctga agatgaactc attgcaaaca       720
gatgatacag ctatatacta ttgtgccaag cattactatt atggtggttc ttatgcaatg     780
gattactggg ggcaaggcac gtcagtgaca gtgagttcaa ccaccacccc tgcaccaaga     840
cctccaactc ctgccccaac tattgcaagt cagccacttt ctttgcgacc agaggcgtgc     900
cggccagcgg cgggggcgc agtgcacacg aggggggctgg acttcgcctg tgatttcctc      960
ttcgtgctgc tggggtggg aagcatgggt gtggctgcga tcgtgtgggg tgcctggttc      1020
tggggccgcc gcagctgcca gcaaagggac tcaggtaaca gcccaggaaa tgcattctac     1080
agcaacgtcc tataccggcc ccggggggcc ccaaagaaga gtgaggactg ctctggagag     1140
gggaaggacc agaggggcca gagcatttat tcaaccagtt ccctcaacc ggctccaaga       1200 caaccacatc tcgccagtcg gccttgtccg tcccctagac cctgccccag tcccaggccc     1260
ggccaccccg tctctatggt cagggtctct cctagaccaa gccccaccca gcagccgagg     1320
ccaaaagggt tccccaaagt gggagaggag tggaggagaa agaggaagga gaagcagtca     1380
gagaccagtc ccaaggaatt tttgacaatt tacgaagatg tcaaggatct gaaaaccagg     1440
agaaatcacg agcaggagca gacttttcct ggaggggga gcaccatcta ctctatgatc     1500
cagtcccagt cttctgctcc cacgtcacaa gaacctgcat atacattata ttcattaatt     1560
cagccttcca ggaagtctgg atccaggaag aggaaccaca gccttccctt caatagcact     1620
atctatgaag tgattggaaa gagtcaacct aaagcccaga accctgctcg attgagccgc     1680
```

-continued

```
aaagagctgg agaactttga tgtttattcc agagtgaagt tcagcaggag cgcagacgcc   1740
cccgcgtacc agcagggcca gaaccagctc tataacgagc tcaatctagg acgaagagag   1800
gagtacgatg ttttggacaa gagacgtggc cgggaccctg agatggggg aaagccgcag    1860 agaaggaaga accctcagga aggcctgtac aatgaactgc agaaagataa gatggcggag   1920
gcctacagtg agattgggat gaaaggcgag cgccggaggg gcaagggca cgatggcctt     1980 taccagggtc tcagtacagc caccaaggac acctacgacg cccttcacat gcaggccctg    2040
cccctcgc                                                            2049
```

<210> SEQ ID NO 12
<211> LENGTH: 683
<212> TYPE: PRT
<213> ORGANISM: Artificial Sequence
<220> FEATURE:
<223> OTHER INFORMATION: CD19.CAR2

<400> SEQUENCE: 12

```
Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
            20                  25                  30

Ile Gln Met Thr Gln Thr Thr Ser Ser Leu Ser Ala Ser Leu Gly Asp
        35                  40                  45

Arg Val Thr Ile Ser Cys Arg Ala Ser Gln Asp Ile Ser Lys Tyr Leu
    50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
            100                 105                 110

Asp Ile Ala Thr Tyr Phe Cys Gln Gln Gly Asn Thr Leu Pro Tyr Thr
        115                 120                 125

Phe Gly Gly Gly Thr Lys Leu Glu Ile Thr Gly Gly Gly Gly Ser Gly
    130                 135                 140

Gly Gly Gly Ser Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
                180                 185                 190

Pro Pro Arg Lys Gly Leu Glu Trp Leu Gly Val Ile Trp Gly Ser Glu
            195                 200                 205

Thr Thr Tyr Tyr Asn Ser Ala Leu Lys Ser Arg Leu Thr Ile Ile Lys
        210                 215                 220

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Tyr Gly Gly
                245                 250                 255

Ser Tyr Ala Met Asp Tyr Trp Gly Gln Gly Thr Ser Val Thr Val Ser
            260                 265                 270

Ser Thr Thr Thr Pro Ala Pro Arg Pro Pro Thr Pro Ala Pro Thr Ile
        275                 280                 285
```

```
Ala Ser Gln Pro Leu Ser Leu Arg Pro Glu Ala Cys Arg Pro Ala Ala
    290             295             300

Gly Gly Ala Val His Thr Arg Gly Leu Asp Phe Ala Cys Asp Phe Leu
305             310             315             320

Phe Val Leu Leu Gly Val Gly Ser Met Gly Val Ala Ala Ile Val Trp
            325             330             335

Gly Ala Trp Phe Trp Gly Arg Arg Ser Cys Gln Gln Arg Asp Ser Gly
            340             345             350

Asn Ser Pro Gly Asn Ala Phe Tyr Ser Asn Val Leu Tyr Arg Pro Arg
    355             360             365

Gly Ala Pro Lys Lys Ser Glu Asp Cys Ser Gly Glu Gly Lys Asp Gln
    370             375             380

Arg Gly Gln Ser Ile Tyr Ser Thr Ser Phe Pro Gln Pro Ala Pro Arg
385             390             395             400

Gln Pro His Leu Ala Ser Arg Pro Cys Pro Ser Pro Arg Pro Cys Pro
            405             410             415

Ser Pro Arg Pro Gly His Pro Val Ser Met Val Arg Val Ser Pro Arg
    420             425             430

Pro Ser Pro Thr Gln Gln Pro Arg Pro Lys Gly Phe Pro Lys Val Gly
    435             440             445

Glu Glu Trp Arg Arg Lys Arg Lys Glu Lys Gln Ser Glu Thr Ser Pro
    450             455             460

Lys Glu Phe Leu Thr Ile Tyr Glu Asp Val Lys Asp Leu Lys Thr Arg
465             470             475             480

Arg Asn His Glu Gln Glu Gln Thr Phe Pro Gly Gly Gly Ser Thr Ile
            485             490             495

Tyr Ser Met Ile Gln Ser Gln Ser Ser Ala Pro Thr Ser Gln Glu Pro
            500             505             510

Ala Tyr Thr Leu Tyr Ser Leu Ile Gln Pro Ser Arg Lys Ser Gly Ser
            515             520             525

Arg Lys Arg Asn His Ser Pro Ser Phe Asn Ser Thr Ile Tyr Glu Val
    530             535             540

Ile Gly Lys Ser Gln Pro Lys Ala Gln Asn Pro Ala Arg Leu Ser Arg
545             550             555             560

Lys Glu Leu Glu Asn Phe Asp Val Tyr Ser Arg Val Lys Phe Ser Arg
            565             570             575

Ser Ala Asp Ala Pro Ala Tyr Gln Gln Gly Gln Asn Gln Leu Tyr Asn
            580             585             590

Glu Leu Asn Leu Gly Arg Arg Glu Glu Tyr Asp Val Leu Asp Lys Arg
            595             600             605

Arg Gly Arg Asp Pro Glu Met Gly Gly Lys Pro Gln Arg Arg Lys Asn
    610             615             620

Pro Gln Glu Gly Leu Tyr Asn Glu Leu Gln Lys Asp Lys Met Ala Glu
625             630             635             640

Ala Tyr Ser Glu Ile Gly Met Lys Gly Glu Arg Arg Arg Gly Lys Gly
            645             650             655

His Asp Gly Leu Tyr Gln Gly Leu Ser Thr Ala Thr Lys Asp Thr Tyr
            660             665             670

Asp Ala Leu His Met Gln Ala Leu Pro Pro Arg
            675             680
```

<210> SEQ ID NO 13
<211> LENGTH: 1623
<212> TYPE: DNA

```
<213> ORGANISM: Artificial Sequence
<220> FEATURE:
<223> OTHER INFORMATION: CD19-T-CAR

<400> SEQUENCE: 13
atggcgctcc ctgtcaccgc actgcttctt ccgctggcac tgctgctgca cgctgcacgg      60
cctgagcaaa aacttatctc tgaagaggac ctcgatatac agatgacgca gacaacgtca     120
agtctttccg ccagcttggg agaccgagtg actatatctt gtagagcaag ccaggatatt     180
tctaagtatc ttaactggta ccaacaaaag cccgatggaa cggttaagct gcttatatac     240
cataccagta gactccactc cggcgtacca tcacggtttt ctggcagtgg ctccgggacc     300
gactattctt tgacgatctc taatctcgaa caagaggata ttgcaacata cttttgtcag     360
caaggcaata ccttgccata tacgtttggg ggcgggacaa aacttgagat aaccggcggc     420
ggtggttcag gcggtggcgg ttccggtggt gggggatcag aggttaagct tcaggaatcc     480
ggaccaggtt tggttgcccc cagccaatct ctcagcgtta catgcacggt ttcaggcgtc     540
agtctccccg attacggtgt aagttggatt cggcaacctc cgcgaaaggg tctggaatgg     600 ctggggggtta tttggggggag tgagacaact tattacaact ctgcacttaa gagtcggctt     660
accatcatca aggataattc aaaatcacaa gtattcctga agatgaactc attgcaaaca     720
gatgatacag ctatatacta ttgtgccaag cattactatt atggtggttc ttatgcaatg     780
gattactggg ggcaaggcac gtcagtgaca gtgagttcaa ccaccacccc tgcaccaaga     840
cctccaactc ctgccccaac tattgcaagt cagccacttt ctttgcgacc agaggcgtgc     900
cggccagcgg cggggggcgc agtgcacacg aggggggctgg acttcgcctg tgattttttgg     960 gtgctggtgg tggttggtgg agtcctggct tgctatagct tgctagtaac agtggccttt    1020
attattttct gggtgaggag taagaggagc aggctcctgc acagtgacta catgaacatg    1080
actccccgcc gccccgggcc cacccgcaag cattaccagc cctatgcccc accacgcgac    1140
ttcgcagcct atcgctccaa acggggcaga aagaaactcc tgtatatatt caaacaacca    1200
tttatgagac cagtacaaac tactcaagag gaagatggct gtagctgccg atttccagaa    1260
gaagaagaag gaggatgtga actgagagtg aagttcagca ggagcgcaga cgcccccgcg    1320
taccagcagg gccagaacca gctctataac gagctcaatc taggacgaag agaggagtac    1380 gatgtttttgg acaagagacg tggccgggac cctgagatgg ggggaaagcc gcagagaagg    1440
aagaaccctc aggaaggcct gtacaatgaa ctgcagaaag ataagatggc ggaggcctac    1500
agtgagattg ggatgaaagg cgagcgccgg aggggcaagg ggcacgatgg cctttaccag    1560
ggtctcagta cagccaccaa ggacacctac gacgcccttc acatgcaggc cctgccccct    1620
cgc                                                                  1623

<210> SEQ ID NO 14
<211> LENGTH: 541
<212> TYPE: PRT
<213> ORGANISM: Artificial Sequence
<220> FEATURE:
<223> OTHER INFORMATION: CD19.T-CAR

<400> SEQUENCE: 14

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
                20                  25                  30

Ile Gln Met Thr Gln Thr Thr Ser Ser Leu Ser Ala Ser Leu Gly Asp
```

-continued

```
             35                  40                  45
Arg Val Thr Ile Ser Cys Arg Ala Ser Gln Asp Ile Ser Lys Tyr Leu
    50                  55                  60
Asn Trp Tyr Gln Gln Lys Pro Asp Gly Thr Val Lys Leu Leu Ile Tyr
65                  70                  75                  80
His Thr Ser Arg Leu His Ser Gly Val Pro Ser Arg Phe Ser Gly Ser
                85                  90                  95
Gly Ser Gly Thr Asp Tyr Ser Leu Thr Ile Ser Asn Leu Glu Gln Glu
            100                 105                 110
Asp Ile Ala Thr Tyr Phe Cys Gln Gln Gly Asn Thr Leu Pro Tyr Thr
            115                 120                 125
Phe Gly Gly Gly Thr Lys Leu Glu Ile Thr Gly Gly Gly Ser Gly
    130                 135                 140
Gly Gly Gly Ser Gly Gly Gly Ser Glu Val Lys Leu Gln Glu Ser
145                 150                 155                 160
Gly Pro Gly Leu Val Ala Pro Ser Gln Ser Leu Ser Val Thr Cys Thr
            165                 170                 175
Val Ser Gly Val Ser Leu Pro Asp Tyr Gly Val Ser Trp Ile Arg Gln
            180                 185                 190
Pro Pro Arg Lys Gly Leu Glu Trp Leu Gly Val Ile Trp Gly Ser Glu
            195                 200                 205
Thr Thr Tyr Tyr Asn Ser Ala Leu Lys Ser Arg Leu Thr Ile Ile Lys
    210                 215                 220
Asp Asn Ser Lys Ser Gln Val Phe Leu Lys Met Asn Ser Leu Gln Thr
225                 230                 235                 240
Asp Asp Thr Ala Ile Tyr Tyr Cys Ala Lys His Tyr Tyr Tyr Gly Gly
            245                 250                 255
Ser Tyr Ala Met Asp Tyr Trp Gly Gln Gly Thr Ser Val Thr Val Ser
            260                 265                 270
Ser Thr Thr Thr Pro Ala Pro Arg Pro Pro Thr Pro Ala Pro Thr Ile
            275                 280                 285
Ala Ser Gln Pro Leu Ser Leu Arg Pro Glu Ala Cys Arg Pro Ala Ala
    290                 295                 300
Gly Gly Ala Val His Thr Arg Gly Leu Asp Phe Ala Cys Asp Phe Trp
305                 310                 315                 320
Val Leu Val Val Val Gly Gly Val Leu Ala Cys Tyr Ser Leu Leu Val
            325                 330                 335
Thr Val Ala Phe Ile Ile Phe Trp Val Arg Ser Lys Arg Ser Arg Leu
            340                 345                 350
Leu His Ser Asp Tyr Met Asn Met Thr Pro Arg Arg Pro Gly Pro Thr
            355                 360                 365
Arg Lys His Tyr Gln Pro Tyr Ala Pro Pro Arg Asp Phe Ala Ala Tyr
    370                 375                 380
Arg Ser Lys Arg Gly Arg Lys Lys Leu Leu Tyr Ile Phe Lys Gln Pro
385                 390                 395                 400
Phe Met Arg Pro Val Gln Thr Thr Gln Glu Glu Asp Gly Cys Ser Cys
            405                 410                 415
Arg Phe Pro Glu Glu Glu Glu Gly Gly Cys Glu Leu Arg Val Lys Phe
            420                 425                 430
Ser Arg Ser Ala Asp Ala Pro Ala Tyr Gln Gln Gly Gln Asn Gln Leu
            435                 440                 445
Tyr Asn Glu Leu Asn Leu Gly Arg Arg Glu Glu Tyr Asp Val Leu Asp
    450                 455                 460
```

```
Lys Arg Arg Gly Arg Asp Pro Glu Met Gly Gly Lys Pro Gln Arg Arg
465                 470                 475                 480

Lys Asn Pro Gln Glu Gly Leu Tyr Asn Glu Leu Gln Lys Asp Lys Met
                485                 490                 495

Ala Glu Ala Tyr Ser Glu Ile Gly Met Lys Gly Glu Arg Arg Arg Gly
            500                 505                 510

Lys Gly His Asp Gly Leu Tyr Gln Gly Leu Ser Thr Ala Thr Lys Asp
        515                 520                 525

Thr Tyr Asp Ala Leu His Met Gln Ala Leu Pro Pro Arg
    530                 535                 540
```

```
<210> SEQ ID NO 15
<211> LENGTH: 1689
<212> TYPE: DNA
<213> ORGANISM: Artificial Sequence
<220> FEATURE:
<223> OTHER INFORMATION: CD19.CAR4

<400> SEQUENCE: 15
atggcgctcc ctgtcaccgc actgcttctt ccgctggcac tgctgctgca cgctgcacgg     60
cctgagcaaa aacttatctc tgaagaggac ctcgatatac agatgacgca gacaacgtca    120
agtctttccg ccagcttggg agaccgagtg actatatctt gtagagcaag ccaggatatt    180
tctaagtatc ttaactggta ccaacaaaag cccgatggaa cggttaagct gcttatatac    240
cataccagta gactccactc cggcgtacca tcacggtttt ctggcagtgg ctccgggacc    300
gactattctt tgacgatctc taatctcgaa caagaggata ttgcaacata cttttgtcag    360
caaggcaata ccttgccata cgtttgggg ggcgggacaa aacttgagat aaccggcggc    420
ggtggttcag gcggtggcgg ttccggtggt ggggatcag aggttaagct tcaggaatcc    480
ggaccaggtt tggttgcccc cagccaatct ctcagcgtta catgcacggt ttcaggcgtc    540
agtctccccg attacggtgt aagttggatt cggcaacctc cgcgaaaggg tctggaatgg    600 ctggggggtta tttgggggag tgagacaact tattacaact ctgcacttaa gagtcggctt    660
accatcatca aggataattc aaaatcacaa gtattcctga agatgaactc attgcaaaca    720
gatgatacag ctatatacta ttgtgccaag cattactatt atggtggttc ttatgcaatg    780
gattactggg gcaaggcac gtcagtgaca gtgagttcaa ccaccacccc tgcaccaaga    840
cctccaactc ctgccccaac tattgcaagt cagccacttt ctttgcgacc agaggcgtgc    900
cggccagcgg cggggggcgc agtgcacacg aggggctgg acttcgcctg tgatttcctc    960
ttcgtgctgc tggggtggg aagcatgggt gtggctgcga tcgtgtgggg tgcctggttc   1020
tggggccgcc gcagctgcca gcaaagggac tcaggtaaca gcccaggaaa tgcattctac   1080
agcaacgtcc ataccggcc ccgggggccc caaagaaga gtgaggactg ctctggagag   1140
gggaaggacc agagggcca gagcatttat tcaaccagtt tccctcaacc ggctccaaga   1200
caaccacatc tcgccagtcg gccttgtccg tcccctagac cctgccccag tcccaggccc   1260
ggccaccccg tctctatggt cagggtctct cctagaccaa gccccaccca gcagccgagg   1320
ccaaaagggt tccccaaagt gggagaggag agagtgaagt tcagcaggag cgcagacgcc   1380
cccgcgtacc agcagggcca gaaccagctc tataacgagc tcaatctagg acgaagagag   1440
gagtacgatg ttttggacaa gacgtggc cgggaccctg agatgggggg aaagccgcag   1500
agaaggaaga accctcagga aggcctgtac aatgaactgc agaaagataa gatggcggag   1560
gcctacagtg agattgggat gaaaggcgag cgccggaggg gcaaggggca cgatggcctt   1620
```
taccagggtc tcagtacagc caccaaggac acctacgacg cccttcacat gcaggccctg    1680
ccccctcgc    1689

<210> SEQ ID NO 16
<211> LENGTH: 563
<212> TYPE: PRT
<213> ORGANISM: Artificial Sequence
<220> FEATURE:
<223> OTHER INFORMATION: CD19.CAR4

<400> SEQUENCE: 16

Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
                20                  25                  30

Ile Gln Met Thr Gln Thr Thr Ser Ser Leu Ser Ala Ser Leu Gly Asp
            35                  40                  45

Arg Val Thr Ile Ser Cys Arg Ala Ser Gln Asp Ile Ser Lys Tyr Leu
        50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
                100                 105                 110

Asp Ile Ala Thr Tyr Phe Cys Gln Gln Gly Asn Thr Leu Pro Tyr Thr
            115                 120                 125

Phe Gly Gly Gly Thr Lys Leu Glu Ile Thr Gly Gly Gly Gly Ser Gly
        130                 135                 140

Gly Gly Gly Ser Gly Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
                180                 185                 190

Pro Pro Arg Lys Gly Leu Glu Trp Leu Gly Val Ile Trp Gly Ser Glu
            195                 200                 205

Thr Thr Tyr Tyr Asn Ser Ala Leu Lys Ser Arg Leu Thr Ile Ile Lys
        210                 215                 220

Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Tyr Gly Gly
                245                 250                 255

Ser Tyr Ala Met Asp Tyr Trp Gly Gln Gly Thr Ser Val Thr Val Ser
                260                 265                 270

Ser Thr Thr Thr Pro Ala Pro Arg Pro Pro Thr Pro Ala Pro Thr Ile
            275                 280                 285

Ala Ser Gln Pro Leu Ser Leu Arg Pro Glu Ala Cys Arg Pro Ala Ala
        290                 295                 300

Gly Gly Ala Val His Thr Arg Gly Leu Asp Phe Ala Cys Asp Phe Leu
305                 310                 315                 320

Phe Val Leu Leu Gly Val Gly Ser Met Gly Val Ala Ala Ile Val Trp
                325                 330                 335

Gly Ala Trp Phe Trp Gly Arg Arg Ser Cys Gln Gln Arg Asp Ser Gly

-continued

```
              340               345               350
Asn Ser Pro Gly Asn Ala Phe Tyr Ser Asn Val Leu Tyr Arg Pro Arg
          355               360               365

Gly Ala Pro Lys Lys Ser Glu Asp Cys Ser Gly Glu Gly Lys Asp Gln
          370               375               380

Arg Gly Gln Ser Ile Tyr Ser Thr Ser Phe Pro Gln Pro Ala Pro Arg
385               390               395               400

Gln Pro His Leu Ala Ser Arg Pro Cys Pro Ser Pro Arg Pro Cys Pro
              405               410               415

Ser Pro Arg Pro Gly His Pro Val Ser Met Val Arg Val Ser Pro Arg
              420               425               430

Pro Ser Pro Thr Gln Gln Pro Arg Pro Lys Gly Phe Pro Lys Val Gly
          435               440               445

Glu Glu Arg Val Lys Phe Ser Arg Ser Ala Asp Ala Pro Ala Tyr Gln
          450               455               460

Gln Gly Gln Asn Gln Leu Tyr Asn Glu Leu Asn Leu Gly Arg Arg Glu
465               470               475               480

Glu Tyr Asp Val Leu Asp Lys Arg Arg Gly Arg Asp Pro Glu Met Gly
              485               490               495

Gly Lys Pro Gln Arg Arg Lys Asn Pro Gln Glu Gly Leu Tyr Asn Glu
          500               505               510

Leu Gln Lys Asp Lys Met Ala Glu Ala Tyr Ser Glu Ile Gly Met Lys
          515               520               525

Gly Glu Arg Arg Arg Gly Lys Gly His Asp Gly Leu Tyr Gln Gly Leu
          530               535               540

Ser Thr Ala Thr Lys Asp Thr Tyr Asp Ala Leu His Met Gln Ala Leu
545               550               555               560

Pro Pro Arg
```

<210> SEQ ID NO 17
<211> LENGTH: 1497
<212> TYPE: DNA
<213> ORGANISM: Artificial Sequence
<220> FEATURE:
<223> OTHER INFORMATION: CD19.CAR5

<400> SEQUENCE: 17

```
atggcgctcc ctgtcaccgc actgcttctt ccgctggcac tgctgctgca cgctgcacgg     60
cctgagcaaa aacttatctc tgaagaggac ctcgatatac agatgacgca gacaacgtca    120
agtctttccg ccagcttggg agaccgagtg actatatctt gtagagcaag ccaggatatt    180
tctaagtatc ttaactggta ccaacaaaag cccgatggaa cggttaagct gcttatatac    240
cataccagta gactccactc cggcgtacca tcacggtttt ctggcagtgg ctccgggacc    300
gactattctt tgacgatctc taatctcgaa caagaggata ttgcaacata cttttgtcag    360
caaggcaata ccttgccata tacgtttggg ggcgggacaa aacttgagat aaccggcggc    420
ggtggttcag gcggtggcgg ttccggtggt ggggatcag aggttaagct tcaggaatcc    480
ggaccaggtt tggttgcccc cagccaatct ctcagcgtta catgcacggt ttcaggcgtc    540
agtctccccg attacggtgt aagttggatt cggcaacctc cgcgaaaggg tctggaatgg    600 ctggggggtta tttgggggag tgagacaact tattacaact ctgcacttaa gagtcggctt    660
accatcatca aggataattc aaaatcacaa gtattcctga agatgaactc attgcaaaca    720
gatgatacag ctatatacta ttgtgccaag cattactatt atggtggttc ttatgcaatg    780
```

-continued

```
gattactggg ggcaaggcac gtcagtgaca gtgagttcaa ccaccacccc tgcaccaaga    840
cctccaactc ctgccccaac tattgcaagt cagccacttt ctttgcgacc agaggcgtgc    900
cggccagcgg cggggggcgc agtgcacacg aggggggctgg acttcgcctg tgattttttgg   960 gtgctggtgg tggttggtgg agtcctggct tgctatagct tgctagtaac agtggccttt   1020
attattttct gggtgaggag taagaggagc aggctcctgc acagtgacta catgaacatg   1080
actccccgcc gccccgggcc cacccgcaag cattaccagc cctatgcccc accacgcgac   1140
ttcgcagcct atcgctccag agtgaagttc agcaggagcg cagacgcccc cgcgtaccag   1200
cagggccaga accagctcta taacgagctc aatctaggac gaagagagga gtacgatgtt   1260
ttggacaaga cgtggccg ggaccctgag atggggggaa agccgcagag aaggaagaac    1320
cctcaggaag gcctgtacaa tgaactgcag aaagataaga tggcggaggc ctacagtgag   1380
attgggatga aaggcgagcg ccggaggggc aagggggcacg atggccttta ccagggtctc   1440
agtacagcca ccaaggacac ctacgacgcc cttcacatgc aggccctgcc ccctcgc      1497
```

<210> SEQ ID NO 18
<211> LENGTH: 499
<212> TYPE: PRT
<213> ORGANISM: Artificial Sequence
<220> FEATURE:
<223> OTHER INFORMATION: CD19.CAR5

<400> SEQUENCE: 18

```
Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
            20                  25                  30

Ile Gln Met Thr Gln Thr Thr Ser Ser Leu Ser Ala Ser Leu Gly Asp
        35                  40                  45

Arg Val Thr Ile Ser Cys Arg Ala Ser Gln Asp Ile Ser Lys Tyr Leu
    50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
            100                 105                 110

Asp Ile Ala Thr Tyr Phe Cys Gln Gln Gly Asn Thr Leu Pro Tyr Thr
        115                 120                 125

Phe Gly Gly Gly Thr Lys Leu Glu Ile Thr Gly Gly Gly Gly Ser Gly
    130                 135                 140

Gly Gly Gly Ser Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
            180                 185                 190

Pro Pro Arg Lys Gly Leu Glu Trp Leu Gly Val Ile Trp Gly Ser Glu
        195                 200                 205

Thr Thr Tyr Tyr Asn Ser Ala Leu Lys Ser Arg Leu Thr Ile Ile Lys
    210                 215                 220

Asp Asn Ser Lys Ser Gln Val Phe Leu Lys Met Asn Ser Leu Gln Thr
225                 230                 235                 240
```

```
Asp Asp Thr Ala Ile Tyr Tyr Cys Ala Lys His Tyr Tyr Tyr Gly Gly
            245                 250                 255

Ser Tyr Ala Met Asp Tyr Trp Gly Gln Gly Thr Ser Val Thr Val Ser
            260                 265                 270

Ser Thr Thr Thr Pro Ala Pro Arg Pro Pro Thr Pro Ala Pro Thr Ile
            275                 280                 285

Ala Ser Gln Pro Leu Ser Leu Arg Pro Glu Ala Cys Arg Pro Ala Ala
            290                 295                 300

Gly Gly Ala Val His Thr Arg Gly Leu Asp Phe Ala Cys Asp Phe Trp
305                 310                 315                 320

Val Leu Val Val Val Gly Gly Val Leu Ala Cys Tyr Ser Leu Leu Val
                    325                 330                 335

Thr Val Ala Phe Ile Ile Phe Trp Val Arg Ser Lys Arg Ser Arg Leu
            340                 345                 350

Leu His Ser Asp Tyr Met Asn Met Thr Pro Arg Arg Pro Gly Pro Thr
            355                 360                 365

Arg Lys His Tyr Gln Pro Tyr Ala Pro Pro Arg Asp Phe Ala Ala Tyr
            370                 375                 380

Arg Ser Arg Val Lys Phe Ser Arg Ser Ala Asp Ala Pro Ala Tyr Gln
385                 390                 395                 400

Gln Gly Gln Asn Gln Leu Tyr Asn Glu Leu Asn Leu Gly Arg Arg Glu
                    405                 410                 415

Glu Tyr Asp Val Leu Asp Lys Arg Arg Gly Arg Asp Pro Glu Met Gly
                    420                 425                 430

Gly Lys Pro Gln Arg Arg Lys Asn Pro Gln Glu Gly Leu Tyr Asn Glu
            435                 440                 445

Leu Gln Lys Asp Lys Met Ala Glu Ala Tyr Ser Glu Ile Gly Met Lys
            450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                    485                 490                 495

Pro Pro Arg
```

<210> SEQ ID NO 19
<211> LENGTH: 1356
<212> TYPE: DNA
<213> ORGANISM: Artificial Sequence
<220> FEATURE:
<223> OTHER INFORMATION: CD19.CAR6

<400> SEQUENCE: 19

```
atggcgctcc ctgtcaccgc actgcttctt ccgctggcac tgctgctgca cgctgcacgg      60
cctgagcaaa aacttatctc tgaagaggac ctcgatatac agatgacgca gacaacgtca     120
agtctttccg ccagcttggg agaccgagtg actatatctt gtagagcaag ccaggatatt     180
tctaagtatc ttaactggta ccaacaaaag cccgatggaa cggttaagct gcttatatac     240
cataccagta gactccactc cggcgtacca tcacggtttt ctggcagtgg ctccgggacc     300
gactattctt tgacgatctc taatctcgaa caagaggata ttgcaacata cttttgtcag     360
caaggcaata ccttgccata cgtttgggg gcgggacaa aacttgagat aaccggcggc     420
ggtggttcag gcggtggcgg ttccggtggt gggggatcag aggttaagct tcaggaatcc     480
ggaccaggtt tggttgcccc cagccaatct ctcagcgtta catgcacggt ttcaggcgtc     540
agtctccccg attacggtgt aagttggatt cggcaacctc cgcgaaaggg tctggaatgg     600
```

-continued

```
ctggggggtta tttgggggag tgagacaact tattacaact ctgcacttaa gagtcggctt     660
accatcatca aggataattc aaaatcacaa gtattcctga agatgaactc attgcaaaca     720
gatgatacag ctatatacta ttgtgccaag cattactatt atggtggttc ttatgcaatg     780
gattactggg ggcaaggcac gtcagtgaca gtgagttcaa ccaccacccc tgcaccaaga     840
cctccaactc ctgccccaac tattgcaagt cagccacttt ctttgcgacc agaggcgtgc     900
cggccagcgg cggggggcgc agtgcacacg aggggggctgg acttcgcctg tgatttcctc     960
ttcgtgctgc tggggggtggg aagcatgggt gtggctgcga tcgtgtgggg tgcctggaga    1020
gtgaagttca gcaggagcgc agacgcccccc gcgtaccagc agggccagaa ccagctctat    1080
aacgagctca atctaggacg aagagaggag tacgatgttt tggacaagag acgtggccgg    1140
gaccctgaga tggggggaaa gccgcagaga aggaagaacc ctcaggaagg cctgtacaat    1200
gaactgcaga aagataagat ggcggaggcc tacagtgaga ttgggatgaa aggcgagcgc    1260 cggagggggca aggggcacga tggcctttac cagggtctca gtacagccac caaggacacc    1320
tacgacgccc ttcacatgca ggccctgccc cctcgc                              1356
```

<210> SEQ ID NO 20
<211> LENGTH: 452
<212> TYPE: PRT
<213> ORGANISM: Artificial Sequence
<220> FEATURE:
<223> OTHER INFORMATION: CD19.CAR6

<400> SEQUENCE: 20

```
Met Ala Leu Pro Val Thr Ala Leu Leu Leu Pro Leu Ala Leu Leu Leu
1               5                   10                  15

His Ala Ala Arg Pro Glu Gln Lys Leu Ile Ser Glu Glu Asp Leu Asp
            20                  25                  30

Ile Gln Met Thr Gln Thr Thr Ser Ser Leu Ser Ala Ser Leu Gly Asp
        35                  40                  45

Arg Val Thr Ile Ser Cys Arg Ala Ser Gln Asp Ile Ser Lys Tyr Leu
    50                  55                  60

Asn Trp Tyr Gln Gln Lys Pro Asp Gly Thr Val Lys Leu Leu Ile Tyr
65                  70                  75                  80

His Thr Ser Arg Leu His Ser Gly Val Pro Ser Arg Phe Ser Gly Ser
                85                  90                  95

Gly Ser Gly Thr Asp Tyr Ser Leu Thr Ile Ser Asn Leu Glu Gln Glu
            100                 105                 110

Asp Ile Ala Thr Tyr Phe Cys Gln Gln Gly Asn Thr Leu Pro Tyr Thr
        115                 120                 125

Phe Gly Gly Gly Thr Lys Leu Glu Ile Thr Gly Gly Gly Gly Ser Gly
    130                 135                 140

Gly Gly Gly Ser Gly Gly Gly Gly Ser Glu Val Lys Leu Gln Glu Ser
145                 150                 155                 160

Gly Pro Gly Leu Val Ala Pro Ser Gln Ser Leu Ser Val Thr Cys Thr
                165                 170                 175

Val Ser Gly Val Ser Leu Pro Asp Tyr Gly Val Ser Trp Ile Arg Gln
            180                 185                 190

Pro Pro Arg Lys Gly Leu Glu Trp Leu Gly Val Ile Trp Gly Ser Glu
        195                 200                 205

Thr Thr Tyr Tyr Asn Ser Ala Leu Lys Ser Arg Leu Thr Ile Ile Lys
    210                 215                 220
```

```
Asp Asn Ser Lys Ser Gln Val Phe Leu Lys Met Asn Ser Leu Gln Thr
225                 230                 235                 240

Asp Asp Thr Ala Ile Tyr Tyr Cys Ala Lys His Tyr Tyr Tyr Gly Gly
                245                 250                 255

Ser Tyr Ala Met Asp Tyr Trp Gly Gln Gly Thr Ser Val Thr Val Ser
                260                 265                 270

Ser Thr Thr Thr Pro Ala Pro Arg Pro Pro Thr Pro Ala Pro Thr Ile
            275                 280                 285

Ala Ser Gln Pro Leu Ser Leu Arg Pro Glu Ala Cys Arg Pro Ala Ala
        290                 295                 300

Gly Gly Ala Val His Thr Arg Gly Leu Asp Phe Ala Cys Asp Phe Leu
305                 310                 315                 320

Phe Val Leu Leu Gly Val Gly Ser Met Gly Val Ala Ala Ile Val Trp
                325                 330                 335

Gly Ala Trp Arg Val Lys Phe Ser Arg Ser Ala Asp Ala Pro Ala Tyr
                340                 345                 350

Gln Gln Gly Gln Asn Gln Leu Tyr Asn Glu Leu Asn Leu Gly Arg Arg
        355                 360                 365

Glu Glu Tyr Asp Val Leu Asp Lys Arg Arg Gly Arg Asp Pro Glu Met
        370                 375                 380

Gly Gly Lys Pro Gln Arg Arg Lys Asn Pro Gln Glu Gly Leu Tyr Asn
385                 390                 395                 400

Glu Leu Gln Lys Asp Lys Met Ala Glu Ala Tyr Ser Glu Ile Gly Met
                405                 410                 415

Lys Gly Glu Arg Arg Arg Gly Lys Gly His Asp Gly Leu Tyr Gln Gly
                420                 425                 430

Leu Ser Thr Ala Thr Lys Asp Thr Tyr Asp Ala Leu His Met Gln Ala
            435                 440                 445

Leu Pro Pro Arg
        450

<210> SEQ ID NO 21
<211> LENGTH: 254
<212> TYPE: PRT
<213> ORGANISM: Homo sapiens

<400> SEQUENCE: 21

Met Trp Gln Leu Leu Leu Pro Thr Ala Leu Leu Leu Leu Val Ser Ala
1                 5                 10                 15

Gly Met Arg Thr Glu Asp Leu Pro Lys Ala Val Val Phe Leu Glu Pro
                20                 25                 30

Gln Trp Tyr Arg Val Leu Glu Lys Asp Ser Val Thr Leu Lys Cys Gln
            35                 40                 45

Gly Ala Tyr Ser Pro Glu Asp Asn Ser Thr Gln Trp Phe His Asn Glu
        50                 55                 60

Ser Leu Ile Ser Ser Gln Ala Ser Ser Tyr Phe Ile Asp Ala Ala Thr
65                 70                 75                 80

Val Asp Asp Ser Gly Glu Tyr Arg Cys Gln Thr Asn Leu Ser Thr Leu
                85                 90                 95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
        130                 135                 140
```

```
Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Phe
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 22
<211> LENGTH: 304
<212> TYPE: PRT
<213> ORGANISM: Homo sapiens

<400> SEQUENCE: 22

Met Ser Ser Thr Leu Pro Ala Leu Leu Cys Val Gly Leu Cys Leu Ser
1               5                   10                  15

Gln Arg Ile Ser Ala Gln Gln Thr Leu Pro Lys Pro Phe Ile Trp
                20                  25                  30

Ala Glu Pro His Phe Met Val Pro Lys Glu Lys Gln Val Thr Ile Cys
            35                  40                  45

Cys Gln Gly Asn Tyr Gly Ala Val Glu Tyr Gln Leu His Phe Glu Gly
        50                  55                  60

Ser Leu Phe Ala Val Asp Arg Pro Lys Pro Pro Glu Arg Ile Asn Lys
65                  70                  75                  80

Val Lys Phe Tyr Ile Pro Asp Met Asn Ser Arg Met Ala Gly Gln Tyr
                85                  90                  95

Ser Cys Ile Tyr Arg Val Gly Glu Leu Trp Ser Glu Pro Ser Asn Leu
                100                 105                 110

Leu Asp Leu Val Val Thr Glu Met Tyr Asp Thr Pro Thr Leu Ser Val
            115                 120                 125

His Pro Gly Pro Glu Val Ile Ser Gly Glu Lys Val Thr Phe Tyr Cys
        130                 135                 140

Arg Leu Asp Thr Ala Thr Ser Met Phe Leu Leu Leu Lys Glu Gly Arg
145                 150                 155                 160

Ser Ser His Val Gln Arg Gly Tyr Gly Lys Val Gln Ala Glu Phe Pro
                165                 170                 175

Leu Gly Pro Val Thr Thr Ala His Arg Gly Thr Tyr Arg Cys Phe Gly
            180                 185                 190

Ser Tyr Asn Asn His Ala Trp Ser Phe Pro Ser Glu Pro Val Lys Leu
            195                 200                 205

Leu Val Thr Gly Asp Ile Glu Asn Thr Ser Leu Ala Pro Glu Asp Pro
        210                 215                 220

Thr Phe Pro Ala Asp Thr Trp Gly Thr Tyr Leu Leu Thr Thr Glu Thr
225                 230                 235                 240

Gly Leu Gln Lys Asp His Ala Leu Trp Asp His Thr Ala Gln Asn Leu
                245                 250                 255

Leu Arg Met Gly Leu Ala Phe Leu Val Leu Val Ala Leu Val Trp Phe
```

```
              260                265                270
Leu Val Glu Asp Trp Leu Ser Arg Lys Arg Thr Arg Glu Arg Ala Ser
         275                280                285
Arg Ala Ser Thr Trp Glu Gly Arg Arg Arg Leu Asn Thr Gln Thr Leu
    290                295                300
```

```
<210> SEQ ID NO 23
<211> LENGTH: 201
<212> TYPE: PRT
<213> ORGANISM: Homo sapiens

<400> SEQUENCE: 23

Met Ala Trp Met Leu Leu Leu Ile Leu Ile Met Val His Pro Gly Ser
1                5                  10                 15
Cys Ala Leu Trp Val Ser Gln Pro Pro Glu Ile Arg Thr Leu Glu Gly
             20                25                30
Ser Ser Ala Phe Leu Pro Cys Ser Phe Asn Ala Ser Gln Gly Arg Leu
         35                40                45
Ala Ile Gly Ser Val Thr Trp Phe Arg Asp Glu Val Val Pro Gly Lys
    50                55                60
Glu Val Arg Asn Gly Thr Pro Glu Phe Arg Gly Arg Leu Ala Pro Leu
65                70                75                80
Ala Ser Ser Arg Phe Leu His Asp His Gln Ala Glu Leu His Ile Arg
             85                90                95
Asp Val Arg Gly His Asp Ala Ser Ile Tyr Val Cys Arg Val Glu Val
            100                105                110
Leu Gly Leu Gly Val Gly Thr Gly Asn Gly Thr Arg Leu Val Val Glu
         115                120                125
Lys Glu His Pro Gln Leu Gly Ala Gly Thr Val Leu Leu Leu Arg Ala
    130                135                140
Gly Phe Tyr Ala Val Ser Phe Leu Ser Val Ala Val Gly Ser Thr Val
145                150                155                160
Tyr Tyr Gln Gly Lys Cys Leu Thr Trp Lys Gly Pro Arg Arg Gln Leu
             165                170                175
Pro Ala Val Val Pro Ala Pro Leu Pro Pro Cys Gly Ser Ser Ala
             180                185                190
His Leu Leu Pro Pro Val Pro Gly Gly
         195                200
```

```
<210> SEQ ID NO 24
<211> LENGTH: 276
<212> TYPE: PRT
<213> ORGANISM: Homo sapiens

<400> SEQUENCE: 24

Met Ala Trp Arg Ala Leu His Pro Leu Leu Leu Leu Leu Leu Leu Phe
1                5                  10                 15
Pro Gly Ser Gln Ala Gln Ser Lys Ala Gln Val Leu Gln Ser Val Ala
             20                25                30
Gly Gln Thr Leu Thr Val Arg Cys Gln Tyr Pro Pro Thr Gly Ser Leu
         35                40                45
Tyr Glu Lys Lys Gly Trp Cys Lys Glu Ala Ser Ala Leu Val Cys Ile
    50                55                60
Arg Leu Val Thr Ser Ser Lys Pro Arg Thr Met Ala Trp Thr Ser Arg
65                70                75                80
Phe Thr Ile Trp Asp Asp Pro Asp Ala Gly Phe Phe Thr Val Thr Met
```

-continued

```
                 85              90              95

Thr Asp Leu Arg Glu Glu Asp Ser Gly His Tyr Trp Cys Arg Ile Tyr
        100             105             110

Arg Pro Ser Asp Asn Ser Val Ser Lys Ser Val Arg Phe Tyr Leu Val
        115             120             125

Val Ser Pro Ala Ser Ala Ser Thr Gln Thr Ser Trp Thr Pro Arg Asp
        130             135             140

Leu Val Ser Ser Gln Thr Gln Thr Gln Ser Cys Val Pro Pro Thr Ala
145             150             155             160

Gly Ala Arg Gln Ala Pro Glu Ser Pro Ser Thr Ile Pro Val Pro Ser
                165             170             175

Gln Pro Gln Asn Ser Thr Leu Arg Pro Gly Pro Ala Ala Pro Ile Ala
                180             185             190

Leu Val Pro Val Phe Cys Gly Leu Leu Val Ala Lys Ser Leu Val Leu
                195             200             205

Ser Ala Leu Leu Val Trp Trp Gly Asp Ile Trp Trp Lys Thr Met Met
        210             215             220

Glu Leu Arg Ser Leu Asp Thr Gln Lys Ala Thr Cys His Leu Gln Gln
225             230             235             240

Val Thr Asp Leu Pro Trp Thr Ser Val Ser Ser Pro Val Glu Arg Glu
                245             250             255

Ile Leu Tyr His Thr Val Ala Arg Thr Lys Ile Ser Asp Asp Asp Asp
                260             265             270

Glu His Thr Leu
        275

<210> SEQ ID NO 25
<211> LENGTH: 304
<212> TYPE: PRT
<213> ORGANISM: Homo sapiens

<400> SEQUENCE: 25

Met Ser Leu Met Val Ile Ile Met Ala Cys Val Gly Phe Phe Leu Leu
1               5               10              15

Gln Gly Ala Trp Pro Gln Glu Gly Val His Arg Lys Pro Ser Phe Leu
                20              25              30

Ala Leu Pro Gly His Leu Val Lys Ser Glu Glu Thr Val Ile Leu Gln
        35              40              45

Cys Trp Ser Asp Val Met Phe Glu His Phe Leu Leu His Arg Glu Gly
        50              55              60

Lys Phe Asn Asn Thr Leu His Leu Ile Gly Glu His His Asp Gly Val
65              70              75              80

Ser Lys Ala Asn Phe Ser Ile Gly Pro Met Met Pro Val Leu Ala Gly
                85              90              95

Thr Tyr Arg Cys Tyr Gly Ser Val Pro His Ser Pro Tyr Gln Leu Ser
        100             105             110

Ala Pro Ser Asp Pro Leu Asp Met Val Ile Ile Gly Leu Tyr Glu Lys
        115             120             125

Pro Ser Leu Ser Ala Gln Pro Gly Pro Thr Val Gln Ala Gly Glu Asn
        130             135             140

Val Thr Leu Ser Cys Ser Ser Arg Ser Ser Tyr Asp Met Tyr His Leu
145             150             155             160

Ser Arg Glu Gly Glu Ala His Glu Arg Arg Leu Pro Ala Val Arg Ser
                165             170             175
```

-continued

```
Ile Asn Gly Thr Phe Gln Ala Asp Phe Pro Leu Gly Pro Ala Thr His
            180             185                 190

Gly Gly Thr Tyr Arg Cys Phe Gly Ser Phe Arg Asp Ala Pro Tyr Glu
        195             200                 205

Trp Ser Asn Ser Ser Asp Pro Leu Leu Val Ser Val Thr Gly Asn Pro
    210             215                 220

Ser Asn Ser Trp Pro Ser Pro Thr Glu Pro Ser Ser Lys Thr Gly Asn
225             230                 235                 240

Pro Arg His Leu His Val Leu Ile Gly Thr Ser Val Val Lys Ile Pro
            245                 250                 255

Phe Thr Ile Leu Leu Phe Phe Leu Leu His Arg Trp Cys Ser Asp Lys
            260             265                 270

Lys Asn Ala Ala Val Met Asp Gln Glu Pro Ala Gly Asn Arg Thr Val
        275             280                 285

Asn Ser Glu Asp Ser Asp Glu Gln Asp His Gln Glu Val Ser Tyr Ala
    290             295                 300
```